United States Patent
Ranum et al.

(10) Patent No.: US 12,392,786 B2
(45) Date of Patent: Aug. 19, 2025

(54) METHODS FOR DIAGNOSING HUNTINGTON'S DISEASE

(71) Applicant: University of Florida Research Foundation, Incorporated, Gainesville, FL (US)

(72) Inventors: Laura Ranum, Gainesville, FL (US); Monica Banez Coronel, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 66 days.

(21) Appl. No.: 18/297,883

(22) Filed: Apr. 10, 2023

(65) Prior Publication Data

US 2023/0288434 A1    Sep. 14, 2023

Related U.S. Application Data

(63) Continuation of application No. 16/695,717, filed on Nov. 26, 2019, now abandoned, which is a continuation of application No. 15/577,995, filed as application No. PCT/US2016/034738 on May 27, 2016, now Pat. No. 10,509,045.

(60) Provisional application No. 62/168,695, filed on May 29, 2015.

(51) Int. Cl.
  *G01N 33/68* (2006.01)
  *C07K 16/18* (2006.01)
  *C12N 15/113* (2010.01)

(52) U.S. Cl.
  CPC ......... *G01N 33/6896* (2013.01); *C07K 16/18* (2013.01); *C12N 15/113* (2013.01); *C12N 2310/11* (2013.01); *G01N 2333/46* (2013.01); *G01N 2800/2835* (2013.01)

(58) Field of Classification Search
  CPC .......... G01N 33/6896; G01N 2333/46; G01N 2800/2835; C07K 16/18; C12N 15/113; C12N 2310/11
  See application file for complete search history.

(56) References Cited

U.S. PATENT DOCUMENTS

| | | |
|---|---|---|
| 5,011,912 A | 4/1991 | Hopp et al. |
| 6,204,008 B1 | 3/2001 | Borneman et al. |
| 6,326,151 B1 | 12/2001 | Katze et al. |
| 6,342,581 B1 | 1/2002 | Rosen et al. |
| 7,008,796 B2 | 3/2006 | Wohlstadter et al. |
| 7,481,997 B1 | 1/2009 | Hardy |
| 8,993,633 B2 | 3/2015 | Megeney et al. |
| 9,448,232 B2 | 9/2016 | Petrucelli et al. |
| 10,295,547 B2 | 5/2019 | Ranum et al. |
| 10,509,045 B2 | 12/2019 | Ranum et al. |
| 10,663,475 B2 | 5/2020 | Ranum et al. |
| 10,940,161 B2 | 3/2021 | Ranum et al. |
| 11,034,974 B2 | 6/2021 | Ling et al. |
| 11,345,911 B2 | 5/2022 | Ranum et al. |
| 11,903,910 B2 | 2/2024 | Ranum et al. |
| 12,025,622 B2* | 7/2024 | Ranum ............... C12Q 1/6883 |
| 2002/0165355 A1 | 11/2002 | Meheus et al. |
| 2003/0233675 A1 | 12/2003 | Cao et al. |
| 2005/0042657 A1 | 2/2005 | Weese-Mayer et al. |
| 2006/0068434 A1 | 3/2006 | Stoerker |
| 2007/0004729 A1 | 1/2007 | Timmer et al. |
| 2007/0014810 A1 | 1/2007 | Baker et al. |
| 2007/0036760 A1 | 2/2007 | Wilson et al. |
| 2007/0093426 A1 | 4/2007 | Wormser |
| 2008/0188457 A1 | 8/2008 | Barlow et al. |
| 2008/0227699 A1 | 9/2008 | Chiba et al. |
| 2008/0248099 A1 | 10/2008 | Ishii |
| 2009/0074721 A1 | 3/2009 | Kim et al. |
| 2009/0143418 A1 | 6/2009 | Dixon et al. |
| 2009/0148866 A1 | 6/2009 | Datwyler et al. |
| 2009/0312395 A1 | 12/2009 | El-Tanani et al. |
| 2010/0298280 A1 | 11/2010 | Kioschis-Schneider et al. |
| 2012/0076785 A1 | 3/2012 | Nikolaev et al. |
| 2012/0094299 A1* | 4/2012 | Ranum ................ C12N 9/12 435/7.1 |
| 2012/0220534 A1 | 8/2012 | Levin et al. |
| 2013/0085169 A1 | 4/2013 | Baghdoyan et al. |
| 2013/0115603 A9 | 5/2013 | Ranum et al. |
| 2014/0100282 A1 | 4/2014 | Wong |
| 2014/0336133 A1 | 11/2014 | Miller et al. |
| 2015/0361166 A1 | 12/2015 | Edbauer et al. |
| 2016/0025747 A1 | 1/2016 | Ranum et al. |
| 2016/0096800 A1 | 4/2016 | Walter et al. |
| 2016/0346297 A1 | 12/2016 | Sheehan |

(Continued)

FOREIGN PATENT DOCUMENTS

| | | |
|---|---|---|
| EP | 2837390 A1 | 2/2015 |
| EP | 2948471 A1 | 12/2015 |

(Continued)

OTHER PUBLICATIONS

Extended European Search Report, mailed Sep. 30, 2016, in connection with Application No. EP 14776090.4.
International Search Report and Written Opinion, mailed Aug. 22, 2014, in connection with Application No. PCT/US2014/022670.
International Preliminary Report on Patentability, mailed Sep. 24, 2015, in connection with Application No. PCT/US2014/022670.
International Search Report and Written Opinion, mailed Sep. 21, 2016, in connection with Application No. PCT/US2016/034738.
International Preliminary Report on Patentability, mailed Dec. 14, 2017, in connection with Application No. PCT/US2016/034738.

(Continued)

*Primary Examiner* — Olga N Chernyshev
(74) *Attorney, Agent, or Firm* — Wolf, Greenfield & Sacks, P.C.

(57) ABSTRACT

The disclosure provides methods for the diagnosis of Huntington's disease. In some embodiments, the method comprises detecting one or more repeat associated non-ATG (RAN) proteins in a biological sample.

19 Claims, 47 Drawing Sheets

Specification includes a Sequence Listing.

(56) References Cited

U.S. PATENT DOCUMENTS

| | | | |
|---|---|---|---|
| 2018/0292416 | A1 | 10/2018 | Ranum et al. |
| 2019/0142858 | A1 | 5/2019 | Ranum et al. |
| 2019/0153445 | A1 | 5/2019 | Seow et al. |
| 2019/0285652 | A1 | 9/2019 | Ranum et al. |
| 2020/0140846 | A1 | 5/2020 | Ranum et al. |
| 2020/0206255 | A9 | 7/2020 | Ranum et al. |
| 2020/0232925 | A1 | 7/2020 | Ranum et al. |
| 2020/0241013 | A1 | 7/2020 | Ranum et al. |
| 2020/0268691 | A1 | 8/2020 | Ranum et al. |
| 2020/0341012 | A1 | 10/2020 | Ranum et al. |
| 2021/0236535 | A1 | 8/2021 | Ranum et al. |
| 2021/0285970 | A1 | 9/2021 | Ranum et al. |
| 2022/0373559 | A1 | 11/2022 | Ranum et al. |
| 2023/0002753 | A1 | 1/2023 | Ranum et al. |
| 2023/0218730 | A1 | 7/2023 | Ranum et al. |
| 2024/0069039 | A1 | 2/2024 | Ranum et al. |
| 2024/0269093 | A1 | 8/2024 | Ranum et al. |

FOREIGN PATENT DOCUMENTS

| | | | |
|---|---|---|---|
| EP | 3440100 | A1 | 2/2019 |
| JP | 2004-518437 | A | 6/2004 |
| JP | 2004-520803 | A | 7/2004 |
| JP | 2007-507223 | A | 3/2007 |
| JP | 2012-501193 | A | 1/2012 |
| JP | 2016-515208 | A | 5/2016 |
| JP | 2016-180665 | A | 10/2016 |
| JP | 2017-019773 | A | 1/2017 |
| JP | 2017-205118 | A | 11/2017 |
| JP | 2019-515894 | A | 6/2019 |
| WO | WO 2001/75067 | A2 | 10/2001 |
| WO | WO 2001/081581 | A2 | 11/2001 |
| WO | WO 2002/040672 | A2 | 5/2002 |
| WO | WO 2002/062945 | A2 | 8/2002 |
| WO | WO 2005/033321 | A2 | 4/2005 |
| WO | WO 2006/083800 | A2 | 8/2006 |
| WO | WO 2009/144480 | A1 | 12/2009 |
| WO | WO 2010/115033 | A2 | 10/2010 |
| WO | WO 2010/132982 | A1 | 11/2010 |
| WO | WO 2011/052906 | A2 | 5/2011 |
| WO | WO 2013/030588 | A1 | 3/2013 |
| WO | WO 2013/061163 | A2 | 5/2013 |
| WO | WO 2013/172537 | A1 | 11/2013 |
| WO | WO 2014/114303 | A1 | 7/2014 |
| WO | WO 2014/114660 | A1 | 7/2014 |
| WO | WO 2014/116865 | A1 | 7/2014 |
| WO | WO 2014/159247 | A1 | 10/2014 |
| WO | WO 2016/025692 | A1 | 2/2016 |
| WO | WO 2017/055612 | A1 | 4/2017 |
| WO | WO 2017/176813 | A1 | 10/2017 |
| WO | WO 2018/035408 | A1 | 2/2018 |
| WO | WO 2018/195110 | A1 | 10/2018 |
| WO | WO 2019/060918 | A1 | 3/2019 |
| WO | WO 2019/067587 | A1 | 4/2019 |
| WO | WO 2021/007110 | A1 | 1/2021 |
| WO | WO 2021/055880 | A1 | 3/2021 |

OTHER PUBLICATIONS

Supplementary Partial European Search Report, mailed Oct. 18, 2019, in connection with Application No. EP 17779695.0.
Extended European Search Report, mailed Jan. 7, 2020, in connection with Application No. EP 17779695.0.
International Search Report and Written Opinion, mailed Jul. 7, 2017, in connection with Application No. PCT/US2017/026020.
International Preliminary Report on Patentability, mailed Oct. 18, 2018, in connection with Application No. PCT/US2017/026020.
Extended European Search Report, mailed Dec. 17, 2020, in connection with Application No. EP 18786964.9.
International Search Report and Written Opinion, mailed Jul. 27, 2018, in connection with Application No. PCT/US2018/028015.
International Preliminary Report on Patentability, mailed Oct. 31, 2019, in connection with Application No. PCT/US2018/028015.
Extended European Search Report, mailed Nov. 26, 2021, in connection with Application No. EP 18860923.4.
International Search Report and Written Opinion, mailed Jan. 15, 2019, in connection with Application No. PCT/US2018/052913.
International Preliminary Report on Patentability, mailed Apr. 9, 2020, in connection with Application No. PCT/US2018/052913.
Extended European Search Report, mailed Jun. 11, 2021, in connection with Application No. EP 18859783.5.
International Search Report and Written Opinion, mailed Dec. 6, 2018, in connection with Application No. PCT/US2018/052745.
International Preliminary Report on Patentability, mailed Apr. 9, 2020, in connection with Application No. PCT/US2018/052745.
Extended European Search Report, mailed Oct. 4, 2023, in connection with application No. EP 20865149.7.
Invitation to Pay Additional Fees, mailed Nov. 30, 2020, in connection with Application No. PCT/US2020/051671.
International Search Report and Written Opinion, mailed Feb. 9, 2021, in connection with Application No. PCT/US2020/051671.
International Preliminary Report on Patentability, mailed Mar. 31, 2022, in connection with Application No. PCT/US2020/051671.
Extended European Search Report, mailed Aug. 25, 2023, in connection with Application No. EP 20869039.6.
International Search Report and Written Opinion, mailed Dec. 31, 2020, in connection with Application No. PCT/US2020/051670.
International Preliminary Report on Patentability, mailed Apr. 7, 2022, in connection with Application No. PCT/US2020/051670.
Extended European Search Report, mailed Oct. 4, 2023, in connection with application No. EP 20874343.5.
Invitation to Pay Additional Fees, mailed Feb. 19, 2021, in connection with Application No. PCT/US2020/054976.
International Search Report and Written Opinion, mailed Apr. 23, 2021, in connection with Application No. PCT/US2020/054976.
International Preliminary Report on Patentability, mailed Apr. 21, 2022, in connection with Application No. PCT/US2020/054976.
Invitation to Pay Additional Fees, mailed Mar. 30, 2023, in connection with Application No. PCT/US2022/051530.
International Search Report and Written Opinion, mailed May 25, 2023, in connection with Application No. PCT/US2022/051530.
International Preliminary Report on Patentability, mailed Jun. 13, 2024, in connection with Application No. PCT/US2022/051530.
International Search Report and Written Opinion, mailed Jul. 19, 2023, in connection with Application No. PCT/US2023/063328.
International Preliminary Report on Patentability, mailed Sep. 12, 2024, in connection with Application No. PCT/US2023/063328.
[No Author Listed] CRC group Top> L. K. Housing> Query, after sampling and sampling, was conducted, kept still in whole blood ; CRC CORPORATION, Jun. 30, 2013. https://web.archive.org/web/20130630024235/http://www.crc-group.co.jp/crc/q_and_a/149.html.
[No Author Listed] EBNA1—Epstein-Barr nuclear antigen 1—Epstein-Barr virus (strain GD1) (HHV-4)—EBNA1 gene & protein, 2018 Jan. 2018. Retrieved from the internet under https://www.uniprot.org/uniprot/Q3KSS4 on Sep. 12, 2018. 6 pages.
[No Author Listed], Abstracts. Medizinische Genetik, Berufsverband Nedizinische Genetik, Muchen, DE. Medgen. Mar. 4, 2016; 28(1):84-232. DOI: 10.1007/s11825-016-0083-5.
Ash et al., Unconventional translation of C9ORF72 GGGGCC expansion generates insoluble polypeptides specific to c9FTD/ALS. Neuron. Feb. 20, 2013;77(4):639-46. doi: 10.1016/j.neuron.2013.02.004. Epub Feb. 12, 2013.
Ashizawa et al., GGCCTG repeats put a hex on Purkinje cells and motor neurons in SCA36. Neurology. Jul. 24, 2012;79(4):302-3. doi: 10.1212/WNL.0b013e31826043d9. Epub Jun. 27, 2012.
Asokan et al., The AAV vector toolkit: poised at the clinical crossroads. Mol Ther. Apr. 2012;20(4):699-708. doi: 10.1038/mt.2011.287. Epub Jan. 24, 2012.
Ayhan et al., SCA8 RAN polySer protein preferentially accumulates in white matter regions and is regulated by eIF3F. EMBO J. Oct. 1, 2018;37(19). pii: e99023. doi: 10.15252/embj.201899023. Epub Sep. 11, 2018.

(56) References Cited

OTHER PUBLICATIONS

Baboonian et al., Cross reaction of antibodies to a glycine/alanine repeat sequence of Epstein-Barr virus nuclear antigen-1 with collagen, cytokeratin, and actin. Ann Rheum Dis. Nov. 1991;50(11):772-5.

Bae et al., Antibody-aided clearance of extracellular α-synuclein prevents cell-to-cell aggregate transmission. J Neurosci. Sep. 26, 2012;32(39):13454-69.

Bando et al., Double-strand RNA dependent protein kinase (PKR) is involved in the extrastriatal degeneration in Parkinson's disease and Huntington's disease. Neurochem Int. Jan. 2005;46(1):11-8. doi: 10.1016/j.neuint.2004.07.005.

Bañez-Coronel et al., A pathogenic mechanism in Huntington's disease involves small CAG-repeated RNAs with neurotoxic activity. PLoS Genet. 2012;8(2):e1002481. doi: 10.1371/journal.pgen.1002481. Epub Feb. 23, 2012.

Bañez-Coronel et al., RAN Translation in Huntington Disease. Neuron. Nov. 18, 2015;88(4):667-77. doi: 10.1016/j.neuron.2015.10.038.

Bañez-Coronel et al., Repeat-associated non-AUG (RAN) translation: insights from pathology. Lab Invest. Jul. 2019;99(7):929-942. doi: 10.1038/s41374-019-0241-x. Epub Mar. 27, 2019.

Bañez-Coronel et al., Sense and antisense RAN proteins in the CAG•CTG polyglutamine spinocerebellar ataxias. International Congress for Ataxia Research. Abstract ID 271. Nov. 1-4, 2022. 1 page.

Barzilai et al., Metformin as a Tool to Target Aging. Cell Metab. Jun. 14, 2016;23(6):1060-1065. doi: 10.1016/j.cmet.2016.05.011.

Batra et al., Partners in crime: bidirectional transcription in unstable microsatellite disease. Hum Mol Genet. Apr. 15, 2010;19(R1):R77-82. doi: 10.1093/hmg/ddq132. Epub Apr. 4, 2010.

Benkirane et al., Oncogenic potential of TAR RNA binding protein TRBP and its regulatory interaction with RNA-dependent protein kinase PKR. EMBO J. Feb. 3, 1997;16(3):611-24. doi: 10.1093/emboj/16.3.611.

Brooks et al., Spinal and bulbar muscular atrophy: a trinucleotide-repeat expansion neurodegenerative disease. Trends Neurosci. Oct. 1995;18(10):459-61. doi: 10.1016/0166-2236(95)94497-s.

Carroll et al., Potent and selective antisense oligonucleotides targeting single-nucleotide polymorphisms in the Huntington disease gene / allele-specific silencing of mutant huntingtin. Mol Ther. Dec. 2011;19(12):2178-85. doi: 10.1038/mt.2011.201. Epub Oct. 4, 2011.

Castelli et al., Mechanisms of repeat-associated non-AUG translation in neurological microsatellite expansion disorders. Biochem Soc Trans. Apr. 30, 2021;49(2):775-792. doi: 10.1042/BST20200690.

Chen et al., Antidiabetic drug metformin (Glucophage$^R$) increases biogenesis of Alzheimer's amyloid peptides via up-regulating BACE1 transcription. Proc Natl Acad Sci U S A. Mar. 10, 2009;106(10):3907-12. doi: 10.1073/pnas.0807991106. Epub Feb. 23, 2009.

Chen et al., Functional genomics in *Drosophila* models of human disease. Briefings in Functional Genomics. Aug. 22, 2012;11(5):405-415.

Cheng et al., C9ORF72 GGGGCC repeat-associated non-AUG translation is upregulated by stress through eIF2α phosphorylation. Nat Commun. Jan. 4, 2018;9(1):51. doi: 10.1038/s41467-017-02495-z.

Cleary et al., New developments in RAN translation: insights from multiple diseases. Curr Opin Genet Dev. Jun. 2017;44:125-134. doi: 10.1016/j.gde.2017.03.006. Epub Mar. 30, 2017. Author Manuscript, 18 pages.

Cleary et al., Repeat associated non-ATG (RAN) translation: new starts in microsatellite expansion disorders. Curr Opin Genet Dev. Jun. 2014;26:6-15. doi: 10.1016/j.gde.2014.03.002. Epub May 22, 2014. Author Manuscript, 20 pages.

Cleary et al., Repeat-associated non-ATG (RAN) translation in neurological disease. Hum Mol Genet. Oct. 15, 2013;22(R1):R45-51. doi: 10.1093/hmg/ddt371. Epub Aug. 4, 2013.

Davidkin et al., Persistence of anti-mumps virus antibodies after a two-dose MMR vaccination. A nine-year follow-up. Vaccine. Nov. 1995;13(16):1617-22. doi: 10.1016/0264-410x(95)00064-8.

Donnelly et al., RNA toxicity from the ALS/FTD C9ORF72 expansion is mitigated by antisense intervention. Neuron. Oct. 16, 2013;80(2):415-28. doi: 10.1016/j.neuron.2013.10.015.

Duan et al., Generation of polyclonal antiserum for the detection of methylarginine proteins. J Immunol Methods. Mar. 30, 2007;320(1-2):132-42. Epub Feb. 6, 2007.

Duellman et al., Antigen-binding properties of monoclonal antibodies reactive with EBNA1 and use in immunoaffinity chromatography. PLoS One. 2009;4(2):e4614. doi: 10.1371/journal.pone.0004614. Epub Feb. 26, 2009.

Foretz et al., Metformin: from mechanisms of action to therapies. Cell Metab. Dec. 2, 2014;20(6):953-66. doi: 10.1016/j.cmet.2014.09.018. Epub Oct. 30, 2014.

Gantois et al., Metformin ameliorates core deficits in a mouse model of fragile X syndrome. Nat Med. Jun. 2017;23(6):674-677. doi: 10.1038/nm.4335. Epub May 15, 2017.

Gkogkas et al., Pharmacogenetic inhibition of eIF4E-dependent Mmp9 mRNA translation reverses fragile X syndrome-like phenotypes. Cell Rep. Dec. 11, 2014;9(5):1742-1755. doi: 10.1016/j.celrep.2014.10.064. Epub Nov. 26, 2014.

Gómez-Tortosa et al., C9ORF72 hexanucleotide expansions of 20-22 repeats are associated with frontotemporal deterioration. Neurology. Jan. 22, 2013;80(4):366-70. doi: 10.1212/WNL.0b013e31827f08ea. Epub Jan. 2, 2013.

Gray et al., Comparability of serum prostate-specific antigen measurement between the Roche Diagnostics Elecsys 2010 and the Abbott Architect i2000. Ann Clin Biochem. May 2004;41(Pt 3):207-12. doi: 10.1258/000456304323019578.

Green et al., RAN translation at C9orf72-associated repeat expansions is selectively enhanced by the integrated stress response. Nat Commun. Dec. 8, 2017;8(1):2005. doi: 10.1038/s41467-017-02200-0.

Guerra et al., Human gene profiling in response to the active protein kinase, interferon-induced serine/threonine protein kinase (PKR), in infected cells. Involvement of the transcription factor ATF-3 in PKR-induced apoptosis. J Biol Chem. Jul. 7, 2006;281(27):18734-45. doi: 10.1074/jbc.M511983200. Epub Apr. 13, 2006.

Hock et al., Antibodies against beta-amyloid slow cognitive decline in Alzheimer's disease. Neuron. May 22, 2003;38(4):547-54.

Jawaid et al., ALS disease onset may occur later in patients with pre-morbid diabetes mellitus. Eur J Neurol. May 2010;17(5):733-9. doi: 10.1111/j.1468-1331.2009.02923.x. Epub Jan. 13, 2010.

Jin et al., Metformin Protects Cells from Mutant Huntingtin Toxicity Through Activation of AMPK and Modulation of Mitochondrial Dynamics. Neuromolecular Med. Dec. 2016;18(4):581-592. doi: 10.1007/s12017-016-8412-z. Epub May 25, 2016. Author Manuscript, 19 pages.

Kearse et al., CGG Repeat-Associated Non-AUG Translation Utilizes a Cap-Dependent Scanning Mechanism of Initiation to Produce Toxic Proteins. Mol Cell. Apr. 21, 2016;62(2):314-322. doi: 10.1016/j.molcel.2016.02.034. Epub Mar. 31, 2016.

Kioumourtzoglou et al., Diabetes Mellitus, Obesity, and Diagnosis of Amyotrophic Lateral Sclerosis: A Population-Based Study. JAMA Neurol. Aug. 2015;72(8):905-11. doi: 10.1001/jamaneurol.2015.0910. Author Manuscript, 15 pages.

Koide et al., Unstable expansion of CAG repeat in hereditary dentatorubral-pallidoluysian atrophy (DRPLA). Nat Genet. Jan. 1994;6(1):9-13. doi: 10.1038/ng0194-9.

Koob et al., An untranslated CTG expansion causes a novel form of spinocerebellar ataxia (SCA8). Nat Genet. Apr. 1999;21(4):379-84. doi: 10.1038/7710.

Leitman et al., ER stress-induced eIF2-alpha phosphorylation underlies sensitivity of striatal neurons to pathogenic huntingtin. PLoS One. Mar. 3, 2014;9(3):e90803. doi: 10.1371/journal.pone.0090803.

Liu et al., C9orf72 BAC Mouse Model with Motor Deficits and Neurodegenerative Features of ALS/FTD. Neuron. May 4, 2016;90(3):521-34. doi: 10.1016/j.neuron.2016.04.005. Epub Apr. 21, 2016.

Ma et al., Metformin therapy in a transgenic mouse model of Huntington's disease. Neurosci Lett. Jan. 10, 2007;411(2):98-103. doi: 10.1016/j.neulet.2006.10.039. Epub Nov. 15, 2006.

(56) References Cited

OTHER PUBLICATIONS

Memmott et al., Metformin prevents tobacco carcinogen—induced lung tumorigenesis. Cancer Prev Res (Phila). Sep. 2010;3(9):1066-76. doi: 10.1158/1940-6207.CAPR-10-0055. Epub Sep. 1, 2010.
Mirkin, Expandable DNA repeats and human disease. Nature. Jun. 21, 2007;447(7147):932-40. doi: 10.1038/nature05977.
Moon et al., Neuronal Regulation of eIF2α Function in Health and Neurological Disorders. Trends Mol Med. Jun. 2018;24(6):575-589. doi: 10.1016/j.molmed.2018.04.001. Epub Apr. 30, 2018.
Mori et al., The C9orf72 GGGGCC repeat is translated into aggregating dipeptide-repeat proteins in FTLD/ALS. Science. Mar. 15, 2013;339(6125):1335-8. doi: 10.1126/science.1232927. Epub Feb. 7, 2013. Supplementary information included.
Nguyen et al., Repeat-Associated Non-ATG Translation: Molecular Mechanisms and Contribution to Neurological Disease. Annu Rev Neurosci. Jul. 8, 2019;42:227-247. doi: 10.1146/annurev-neuro-070918-050405. Epub Mar. 25, 2019. Author Manuscript, 24 pages.
Pakos-Zebrucka et al., The integrated stress response. EMBO Rep. Oct. 2016;17(10):1374-1395. doi: 10.15252/embr.201642195. Epub Sep. 14, 2016.
Park et al., TAR RNA-binding protein is an inhibitor of the interferon-induced protein kinase PKR. Proc Natl Acad Sci U S A. May 24, 1994;91(11):4713-7. doi: 10.1073/pnas.91.11.4713.
Peel et al., Double-stranded RNA-dependent protein kinase, PKR, binds preferentially to Huntington's disease (HD) transcripts and is activated in HD tissue. Hum Mol Genet. Jul. 15, 2001;10(15):1531-8. doi: 10.1093/hmg/10.15.1531.
Perez et al., CCG•CGG interruptions in high-penetrance SCA8 families increase RAN translation and protein toxicity. EMBO Mol Med. Nov. 8, 2021;13(11):e14095. doi: 10.15252/emmm.202114095. Epub Oct. 11, 2021.
Satoh et al., Dystrophic neurites express C9orf72 in Alzheimer's disease brains. Alzheimers Res Ther. Aug. 16, 2012;4(4):33. doi: 10.1186/alzrt136. 13 pages.
Sha et al., Treatment implications of C9ORF72. Alzheimer's Res Ther. Nov. 27, 2012;4(6):46. doi: 10.1186/alzrt149. eCollection 2012.
Shoesmith et al., Amyotrophic lateral sclerosis: update for family physicians. Can Fam Physician. Dec. 2006;52(12):1563-9.
Sonenberg et al., Regulation of translation initiation in eukaryotes: mechanisms and biological targets. Cell. Feb. 20, 2009;136(4):731-45. doi: 10.1016/j.cell.2009.01.042.
Soragni et al., Repeat-Associated Non-ATG (RAN) Translation in Fuchs' Endothelial Corneal Dystrophy. Invest Ophthalmol Vis Sci. Apr. 1, 2018;59(5):1888-1896. doi: 10.1167/iovs.17-23265.
Taylor et al., Decoding ALS: from genes to mechanism. Nature. Nov. 10, 2016;539(7628):197-206. doi: 10.1038/nature20413. Author Manuscript, 28 pages.
Tian et al., Expanded CUG repeat RNAs form hairpins that activate the double-stranded RNA-dependent protein kinase PKR. RNA. Jan. 2000;6(1):79-87. doi: 10.1017/s1355838200991544.
Todd et al., CGG repeat-associated translation mediates neurodegeneration in fragile X tremor ataxia syndrome. Neuron. May 8, 2013;78(3):440-55. doi: 10.1016/j.neuron.2013.03.026. Epub Apr. 18, 2013. Erratum in: Neuron. Jul. 24, 2013;79(2):402.
Todd et al., Insights into the pathogenic mechanisms of Chromosome 9 open reading frame 72 (C9orf72) repeat expansions. J Neurochem. Aug. 2016;138 Suppl 1:145-62. doi: 10.1111/jnc.13623. Epub Jun. 15, 2016.
Trouth et al., Myasthenia gravis: a review. Autoimmune Dis. ;2012:874680. doi: 10.1155/2012/874680. Epub Oct. 31, 2012.
Tsuji, S., Dentatorubral-pallidoluysian atrophy. Handb Clin Neurol. 2012; 103:587-94. doi: 10.1016/B978-0-444-51892-7.00041-3.
Vaughn et al., Inhibition of PKR protects against tunicamycin-induced apoptosis in neuroblastoma cells. Gene. Feb. 15, 2014;536(1):90-6. doi: 10.1016/j.gene.2013.11.074. Epub Dec. 14, 2013.
Vishwakarma et al., Current molecular insight to reveal the dynamics of CAG repeating units in spinocerebellar ataxia. Intractable Rare Dis Res. May 2018;7(2):79-86. doi: 10.5582/irdr.2018.01039.
Wang et al., Comparative Analysis of VOCs in Exhaled Breath of Amyotrophic Lateral Sclerosis and Cervical Spondylotic Myelopathy Patients. Sci Rep. 2016;6:26120. Published May 23, 2016. doi:10.1038/srep26120.
Welnowska et al., Translation of viral mRNA without active eIF2: the case of picornaviruses. PLoS One. 2011;6(7):e22230. doi: 10.1371/journal.pone.0022230. Epub Jul. 14, 2011.
Wieben et al., Amplification-free long-read sequencing of TCF4 expanded trinucleotide repeats in Fuchs Endothelial Corneal Dystrophy. PLoS One. Jul. 5, 2019;14(7):e0219446. doi: 10.1371/journal.pone.0219446.
William et al., Old friends on new paths: metformin as an early phase treatment in Huntington's Disease?, Medizinische Genetik, 28, pp. 215-216, Mar. 4, 2016 (Mar. 4, 2016) (Abstract).
Wojciechowska et al., RAN translation and frameshifting as translational challenges at simple repeats of human neurodegenerative disorders. Nucleic Acids Res. Oct. 29, 2014;42(19):11849-64. doi: 10.1093/nar/gku794. Epub Sep. 12, 2014.
Xiao et al., Isoform-specific antibodies reveal distinct subcellular localizations of C9orf72 in amyotrophic lateral sclerosis. Ann Neurol. Oct. 2015;78(4):568-83. doi: 10.1002/ana.24469. Epub Aug. 29, 2015.
Yanagisawa et al., Protein Binding of a DRPLA Family Through Arginine-Glutamic Acid Dipeptide repeats is Enhanced by Extended polyglutamine. Human Molecular Genetics. 2000;9(9):1433-1442.
Yu et al., Developing therapeutic antibodies for neurodegenerative disease. Neurotherapeutics. Jul. 2013;10(3):459-72. doi: 10.1007/s13311-013-0187-4.
Zhang et al., Aggregation-prone c9FTD/ALS poly(GA) RAN-translated proteins cause neurotoxicity by inducing ER stress. Acta Neuropathol. 2014;128:505-24.
Zhou et al., Antibodies inhibit transmission and aggregation of C9orf72 poly-GA dipeptide repeat proteins. EMBO Mol Med. May 2017;9(5):687-702. doi: 10.15252/emmm.201607054.
Zhu et al., Suppression of PKR promotes network excitability and enhanced cognition by interferon-γ-mediated disinhibition. Cell. Dec. 9, 2011;147(6):1384-96. doi: 10.1016/j.cell.2011.11.029.
Zu et al., Metformin inhibits RAN translation through PKR pathway and mitigates disease in C9orf72 ALS/FTD mice. Proc Natl Acad Sci U S A. Aug. 4, 2020;117(31):18591-18599. doi: 10.1073/pnas.2005748117. Epub Jul. 20, 2020. Supplementary Materials, 33 pages.
Zu et al., Non-ATG-initiated translation directed by microsatellite expansions. Proc Natl Acad Sci U S A. Jan. 4, 2011;108(1):260-5. doi: 10.1073/pnas.1013343108. Epub Dec. 20, 2010.
Zu et al., RAN proteins and RNA foci from antisense transcripts in C9ORF72 ALS and frontotemporal dementia. Proc Natl Acad Sci U S A. Dec. 17, 2013;110(51):E4968-77. doi: 10.1073/pnas.1315438110. Epub Nov. 18, 2013.
Zu et al., RAN Translation Regulated by Muscleblind Proteins in Myotonic Dystrophy Type 2. Neuron. Sep. 13, 2017;95(6):1292-1305.e5. doi: 10.1016/j.neuron.2017.08.039.

\* cited by examiner

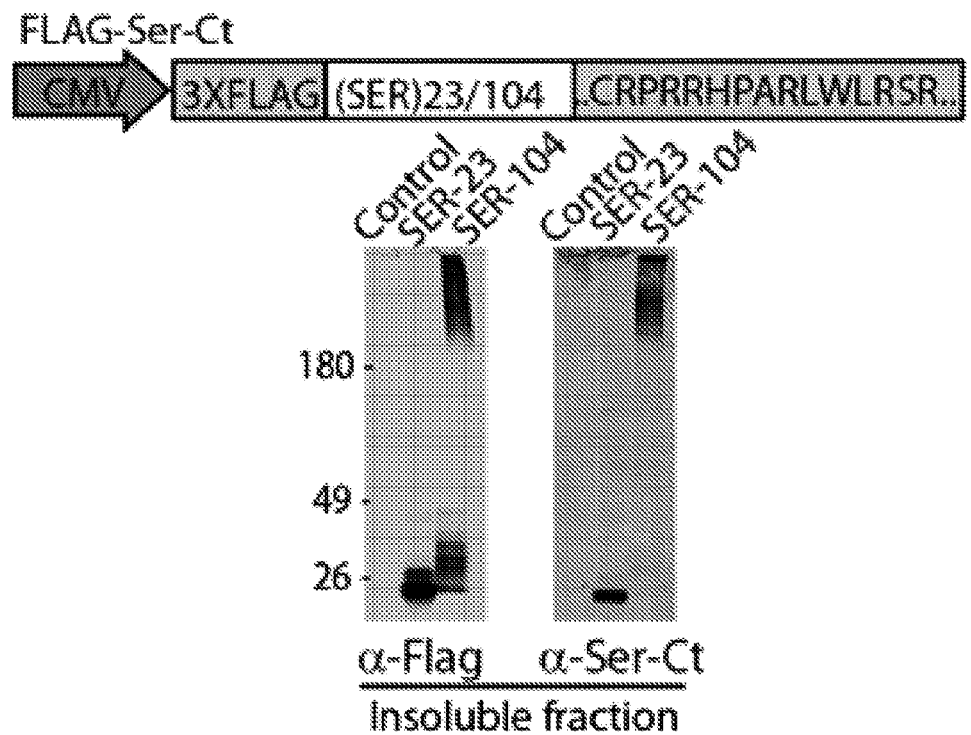
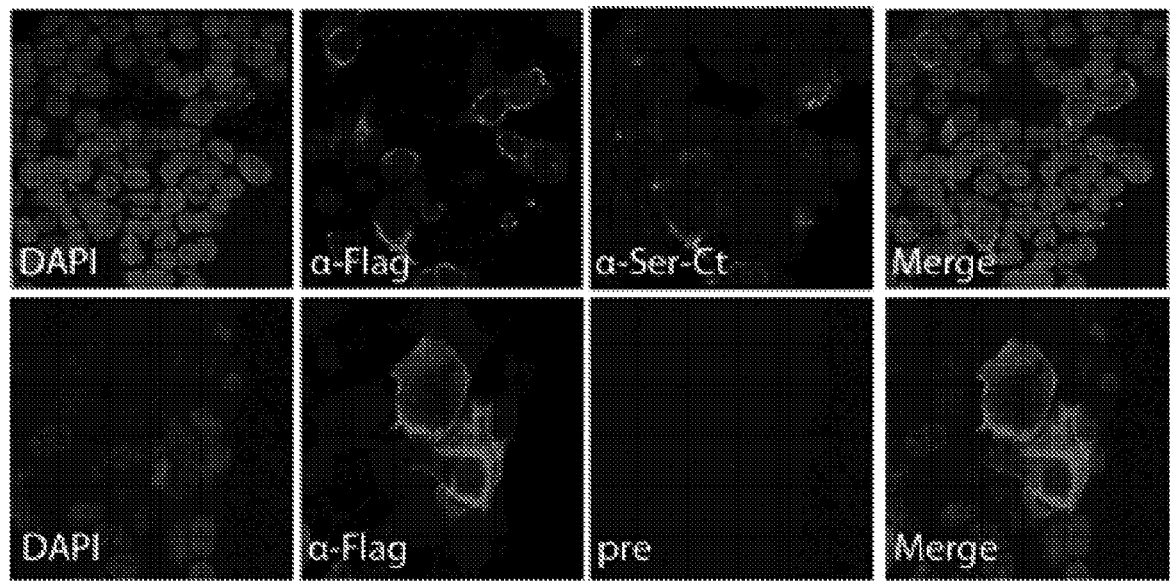
FIG. 8B

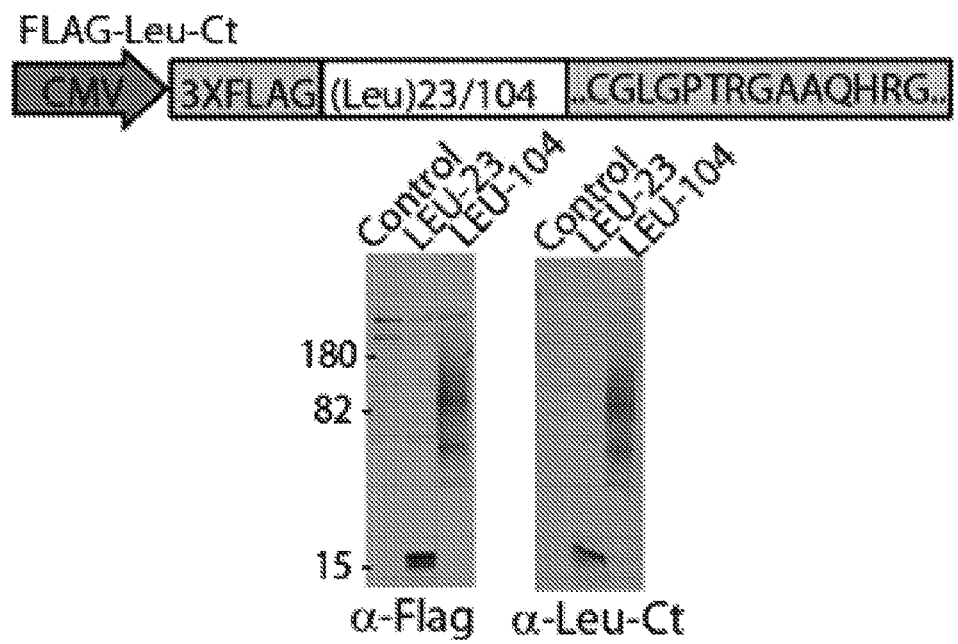
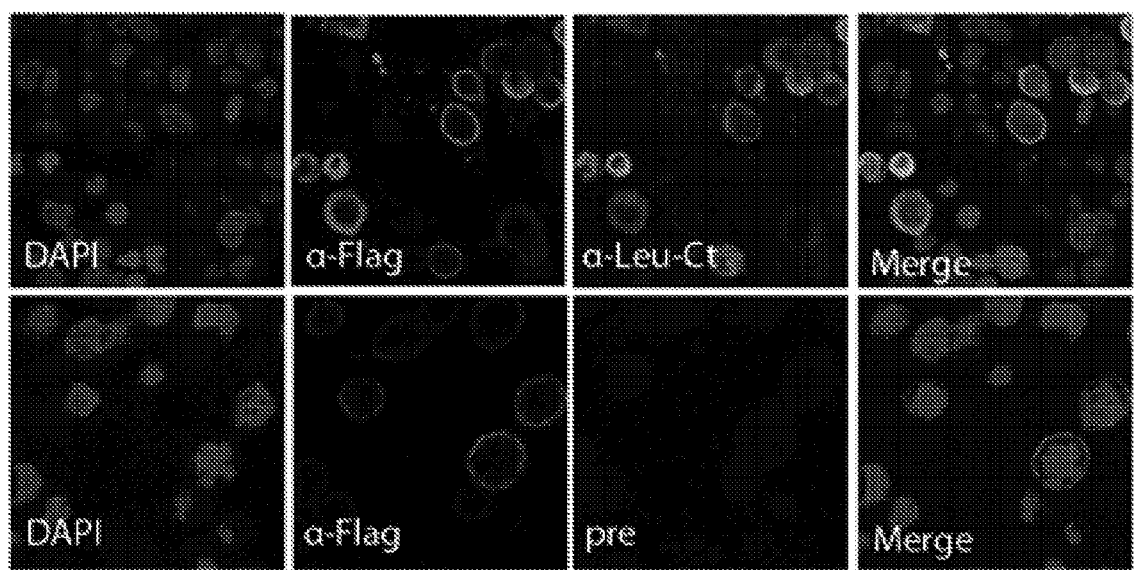
FIG. 8C

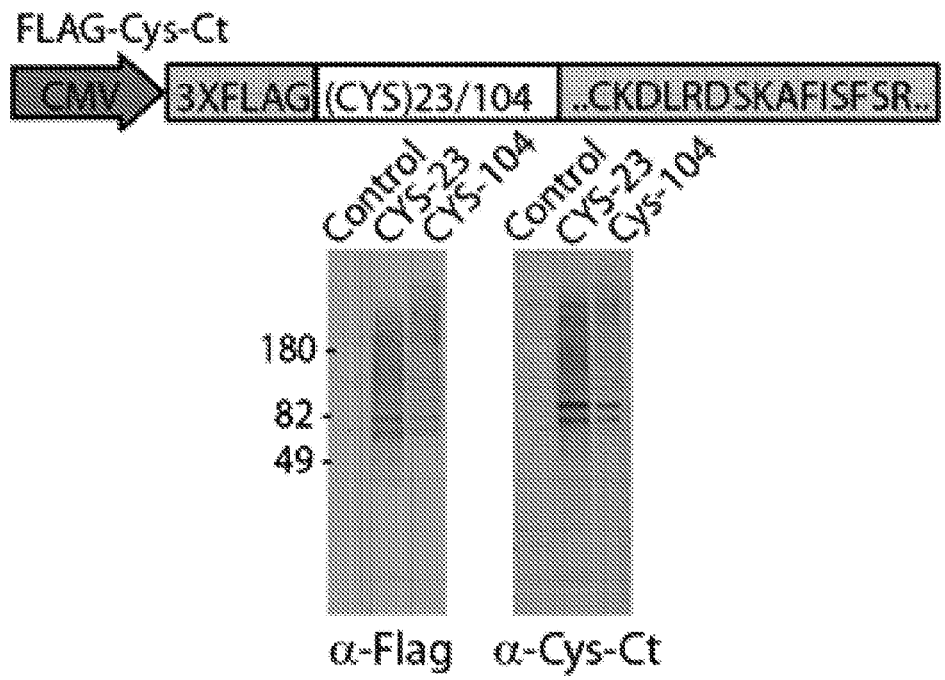
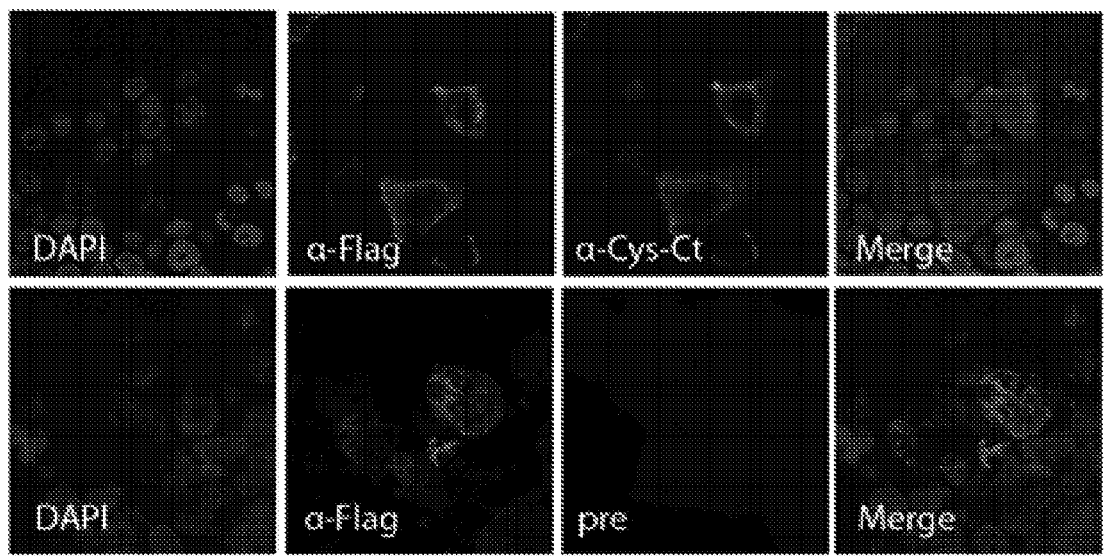
FIG. 8D

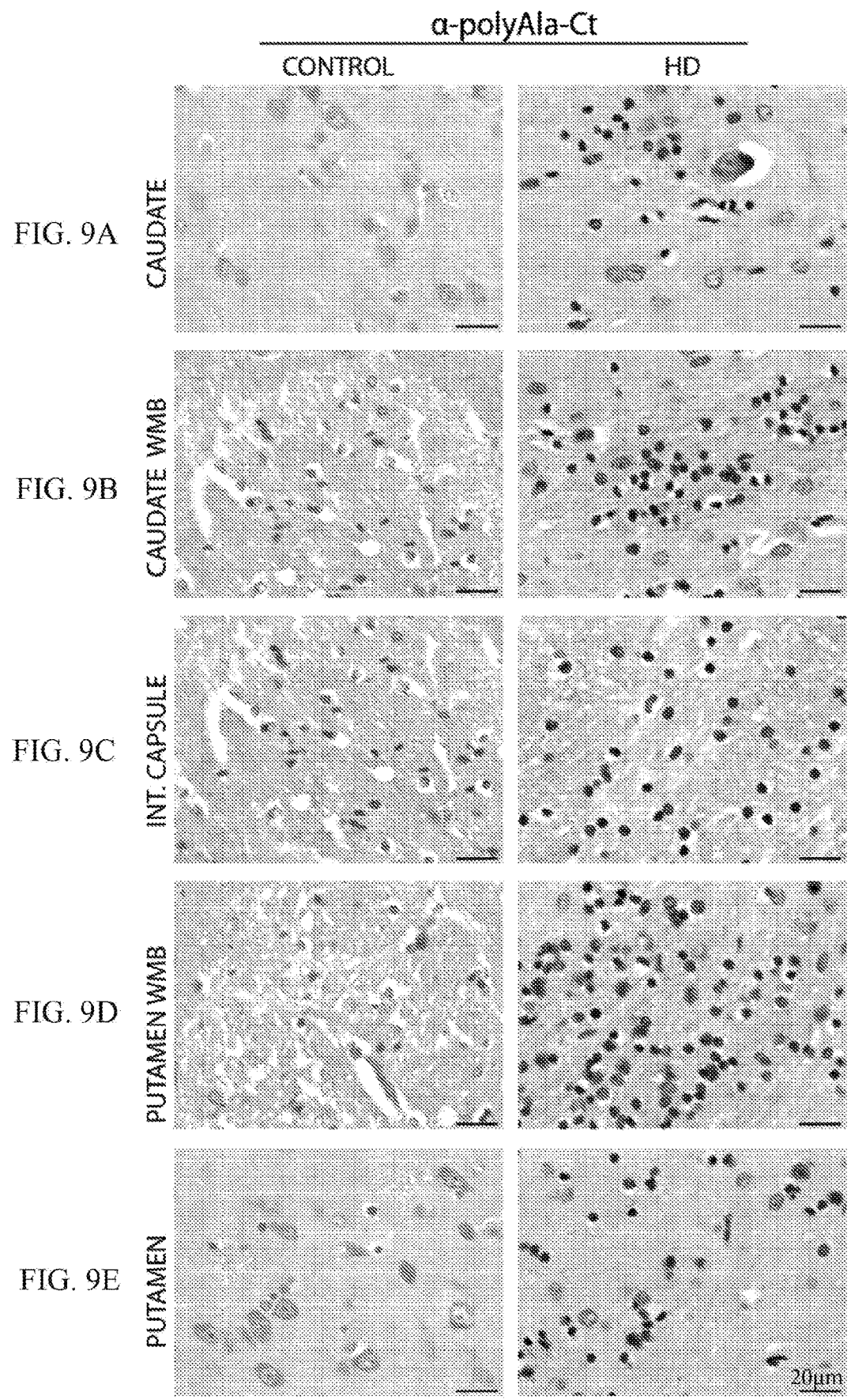

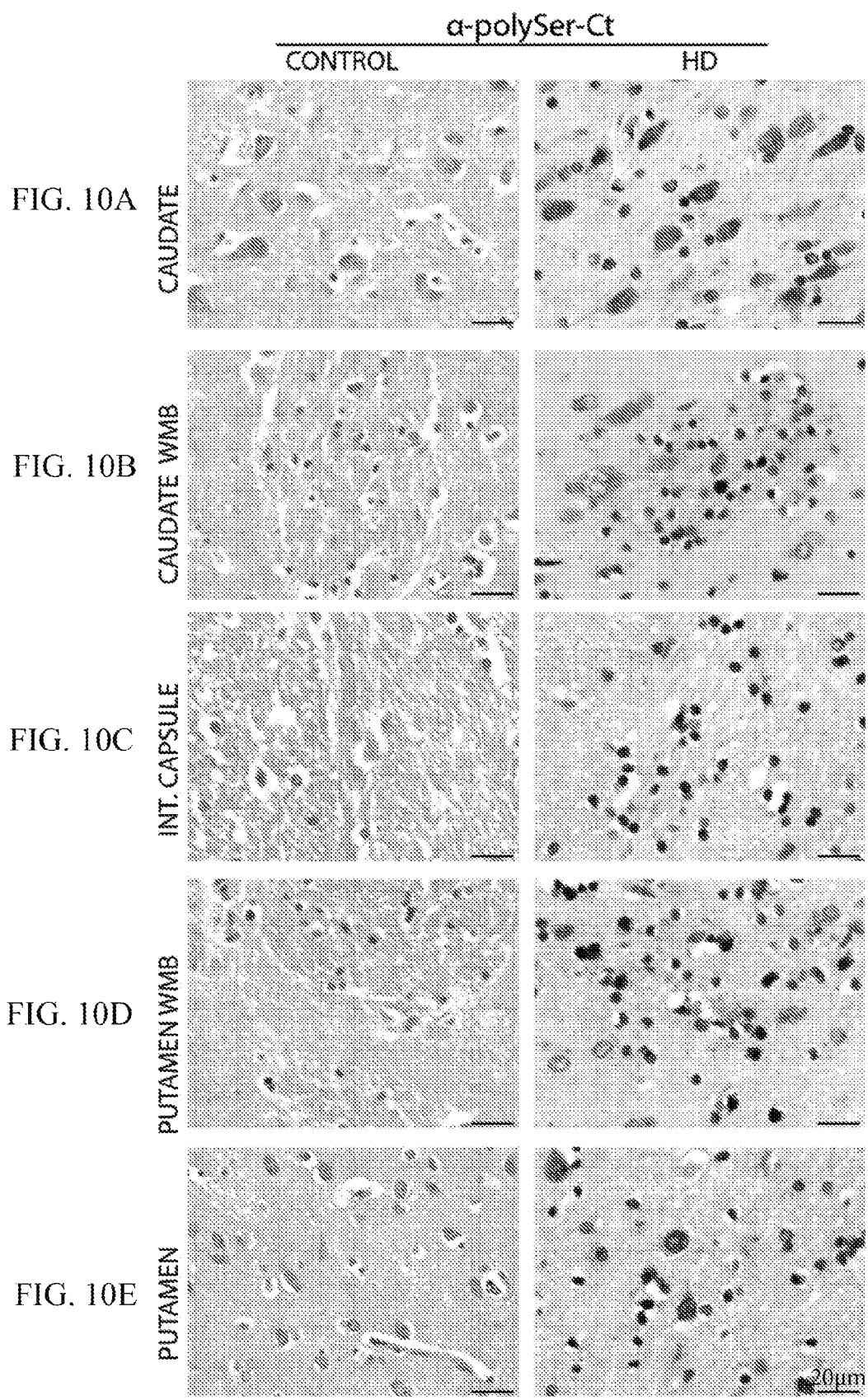

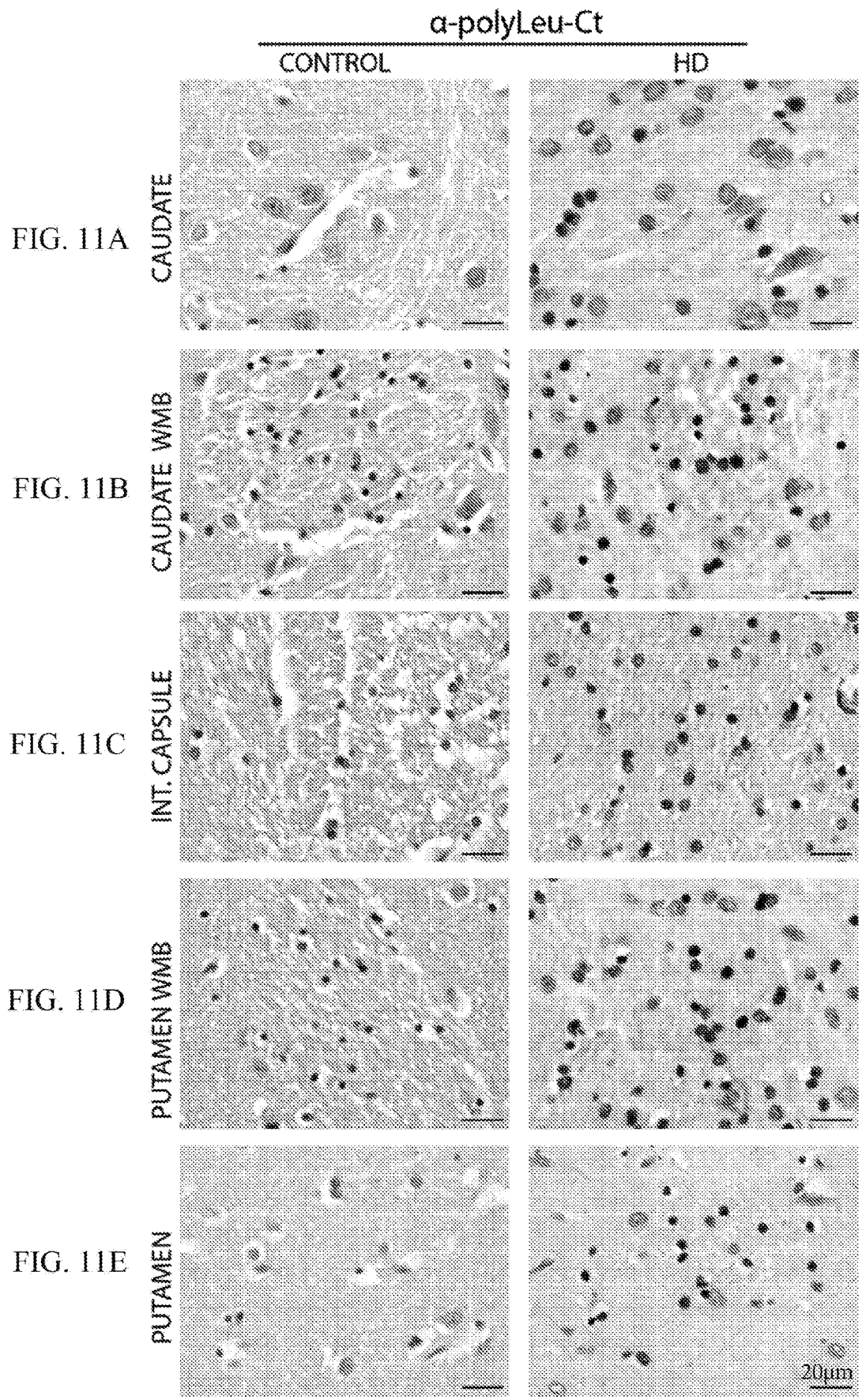

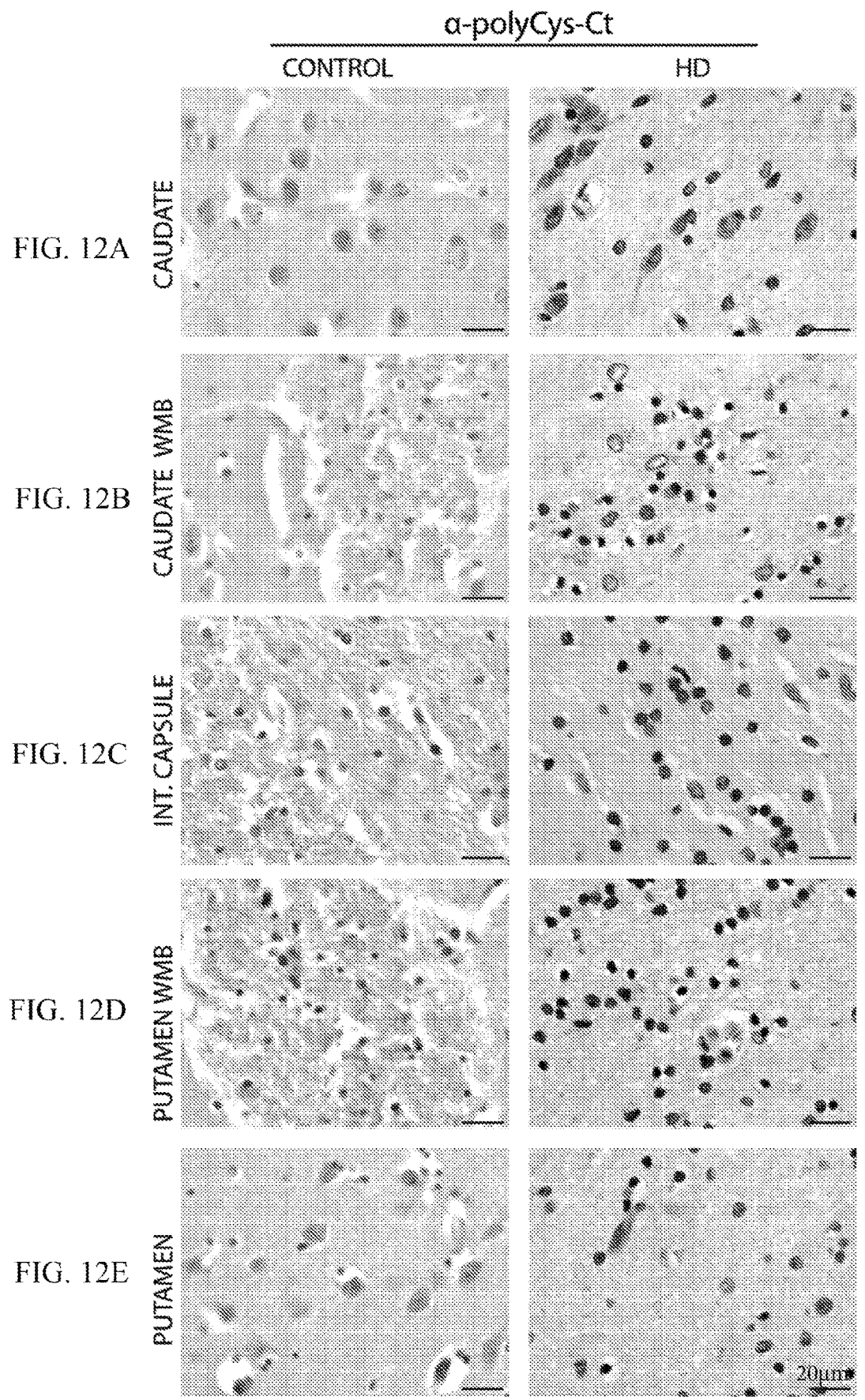

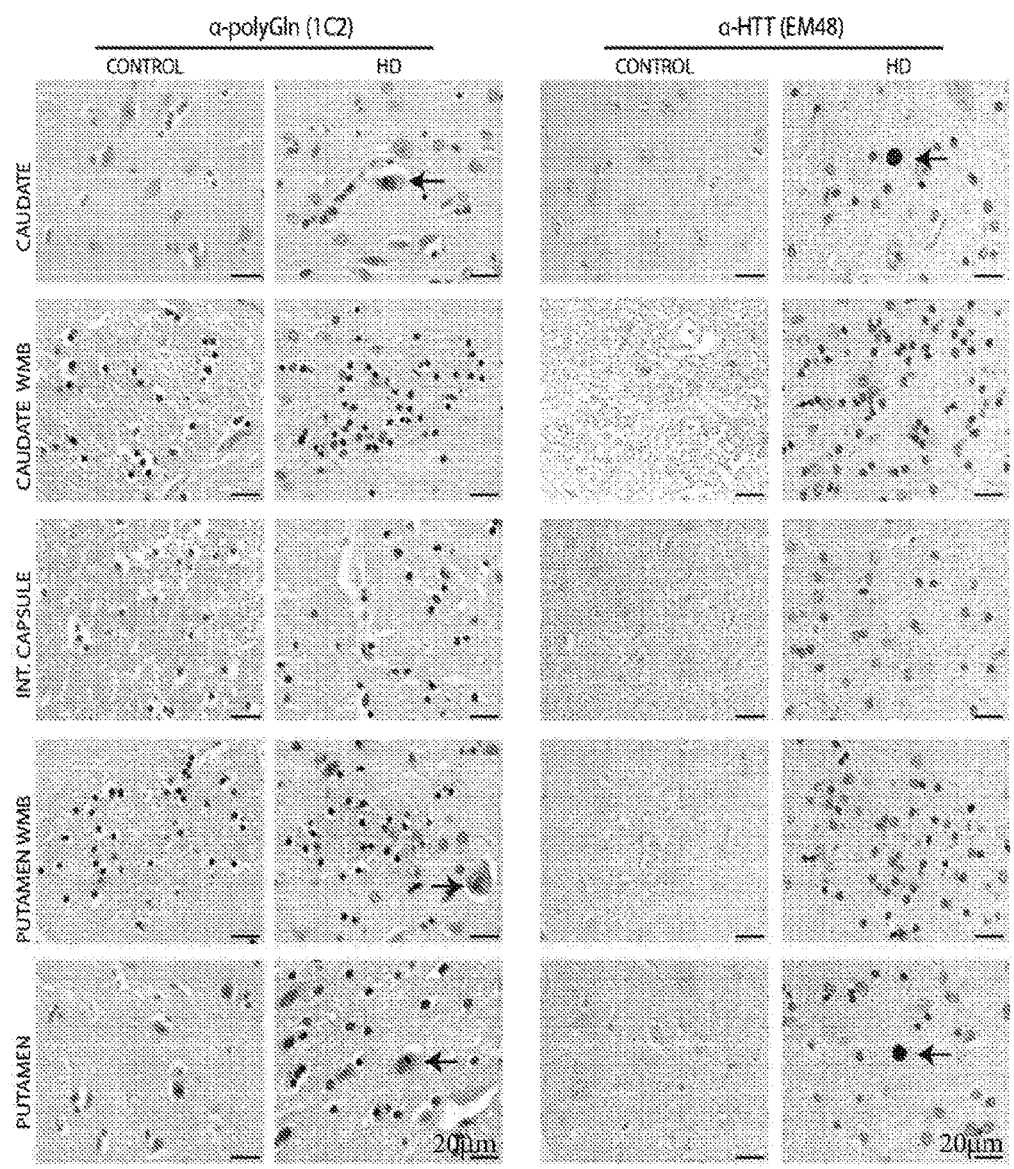

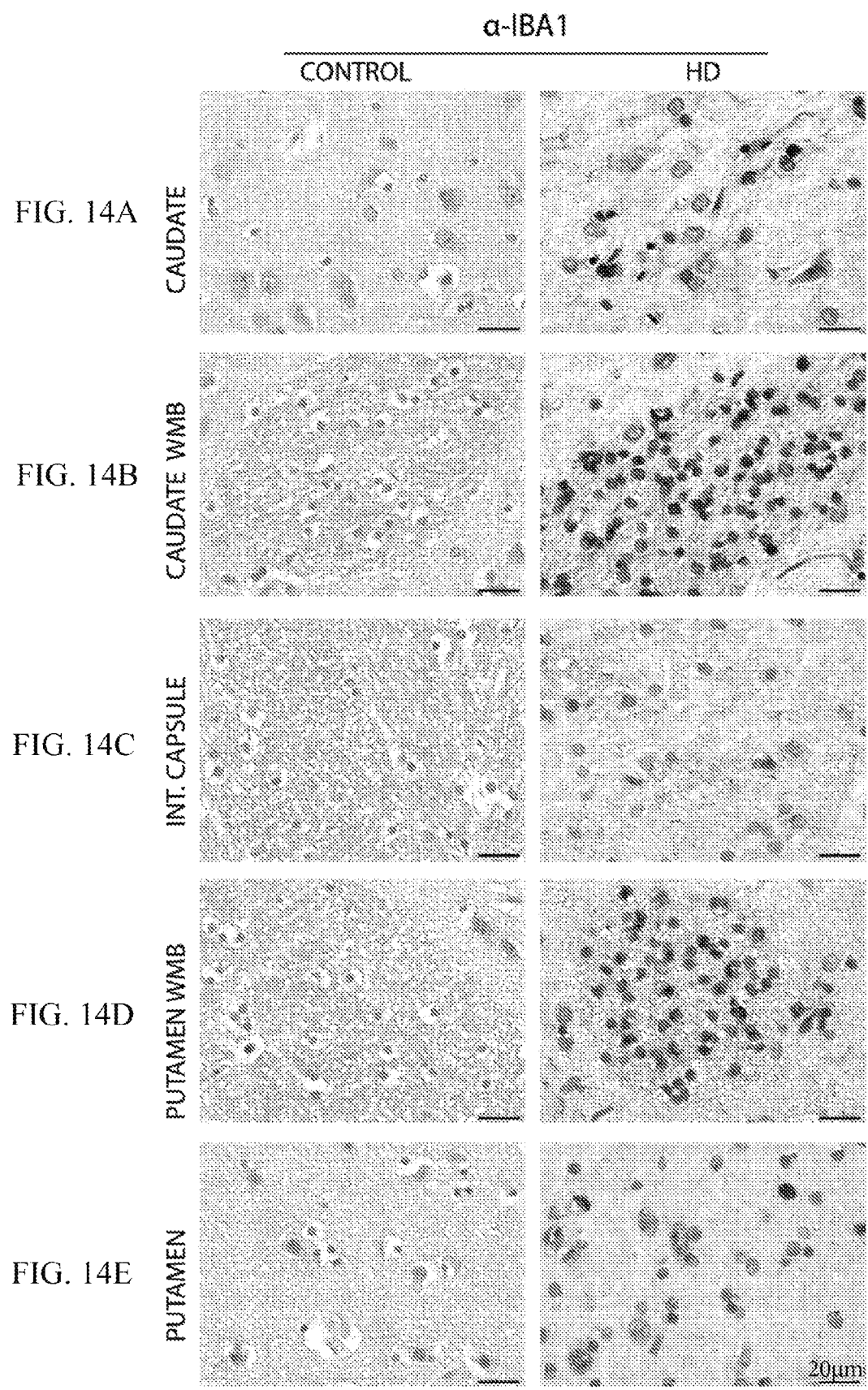

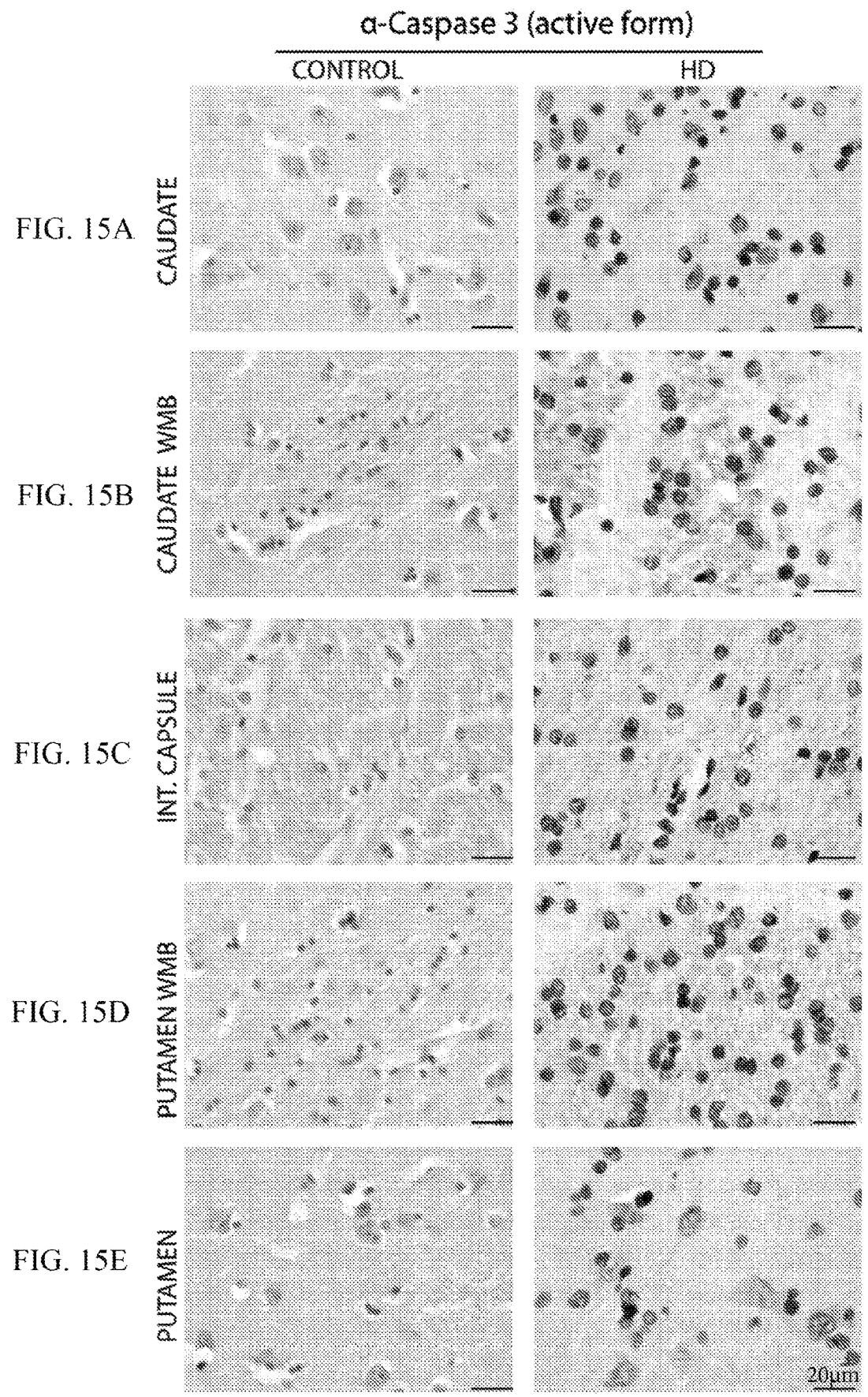

α-polyAla in Frontal Cortex
FIG. 16A GM — CONTROL
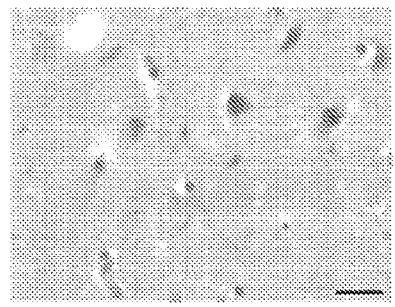
FIG. 16B HD
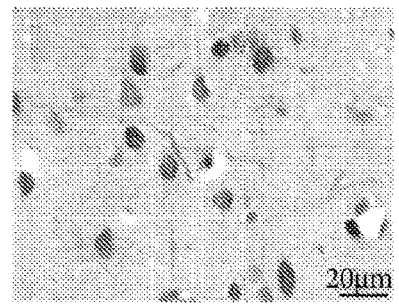
FIG. 16C WM
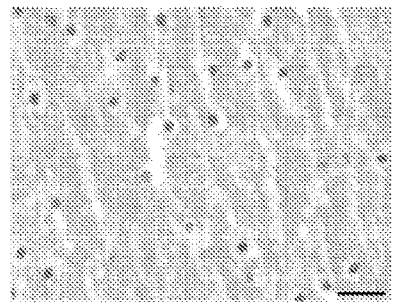
FIG. 16D
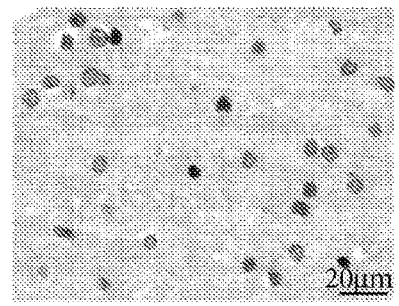
α-polyAla in Cerebellum
FIG. 16E GCL PCL ML — CONTROL
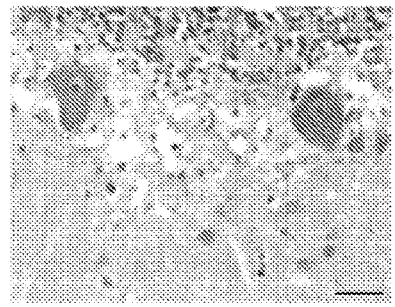
FIG. 16F HD
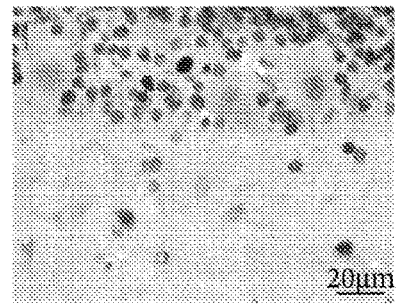
FIG. 16G WM
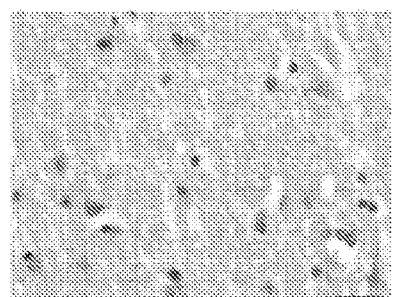
FIG. 16H
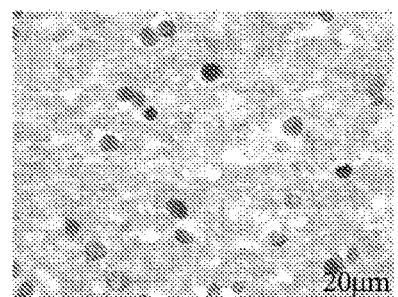

α-polySer in Frontal Cortex
| CONTROL | HD |
FIG. 17A
GM
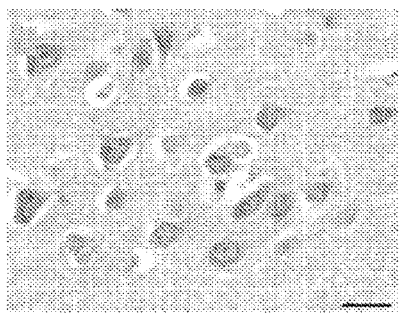 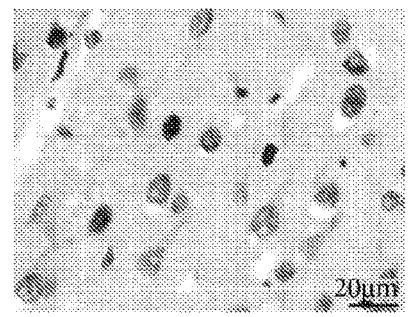
FIG. 17B
FIG. 17C
WM
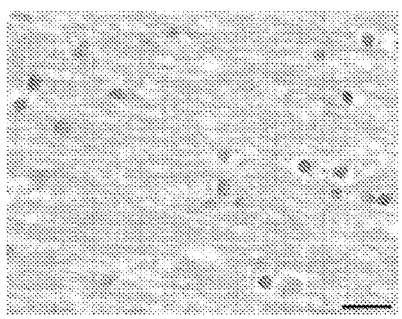 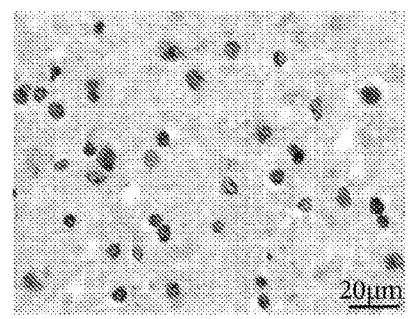
FIG. 17D
α-polySer in Cerebellum
| CONTROL | HD |
GCL
PCL
FIG. 17E
ML
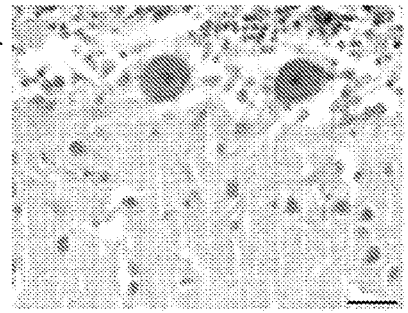 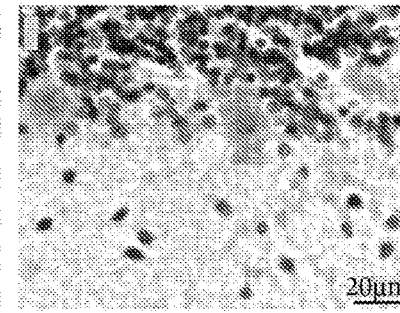
FIG. 17F
FIG. 17G
WM
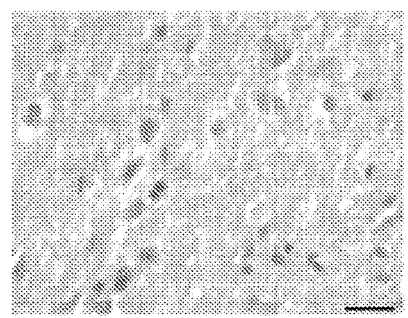 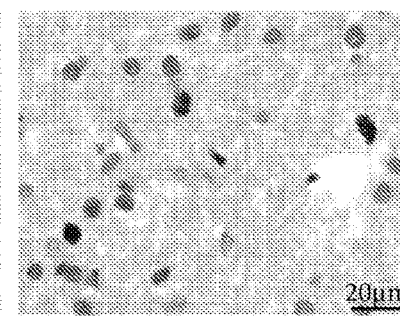
FIG. 17H α-polyLeu in Frontal Cortex
FIG. 18A 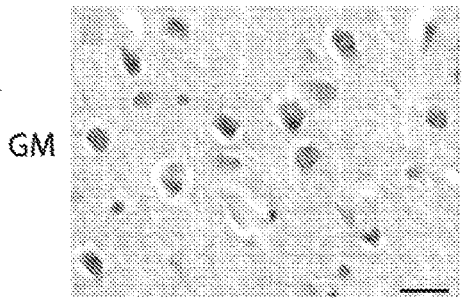 FIG. 18B
GM
FIG. 18C 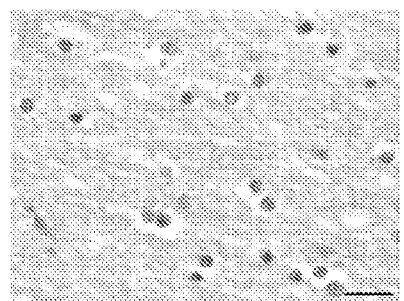 FIG. 18D
WM
FIG. 18E   FIG. 18F   FIG. 18G   FIG. 18H
α-polyLeu in Cerebellum
FIG. 18I 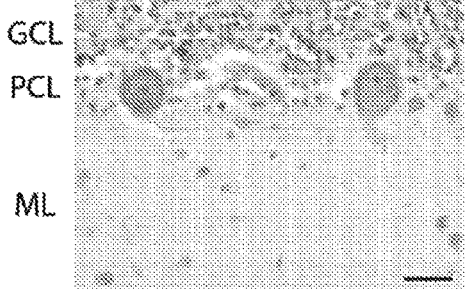 FIG. 18J
GCL
PCL
ML
FIG. 18K 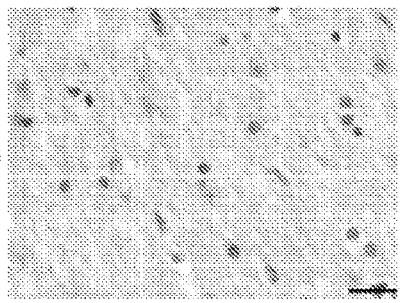 FIG. 18L
WM α-polyCys in Frontal Cortex
CONTROL | HD
FIG. 19A
GM
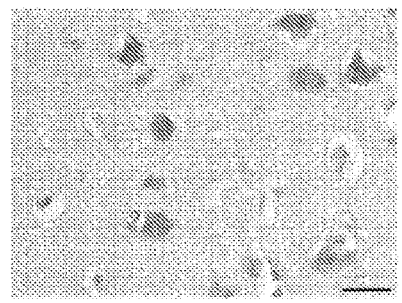 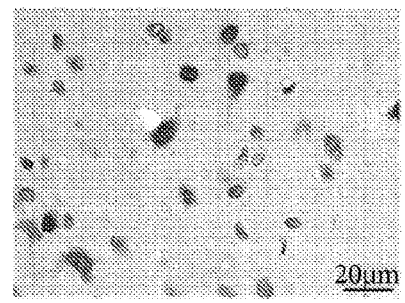
FIG. 19B
FIG. 19C
WM
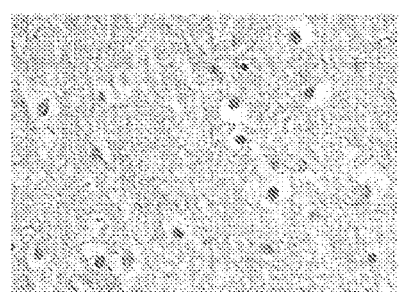 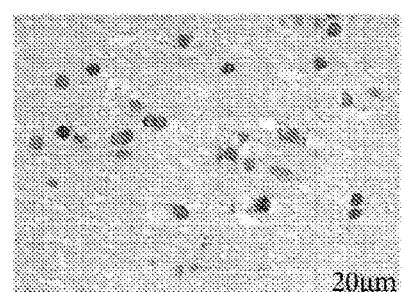
FIG. 19D
α-polyCys in Cerebellum
CONTROL | HD
GCL
PCL
FIG. 19E
ML
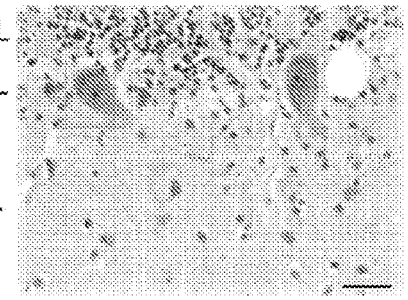 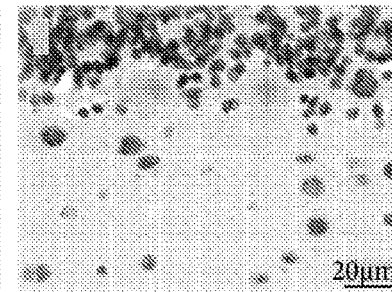
FIG. 19F
FIG. 19G
WM
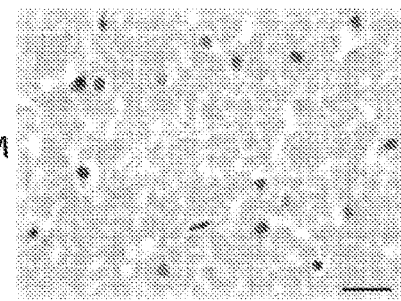 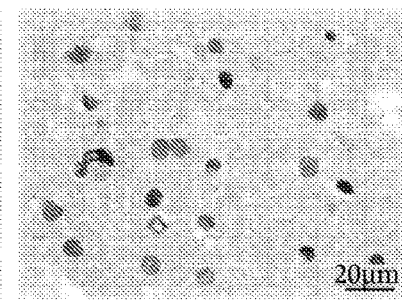
FIG. 19H α-polyGln (1C2) in Frontal Cortex
CONTROL | HD
FIG. 20A
GM
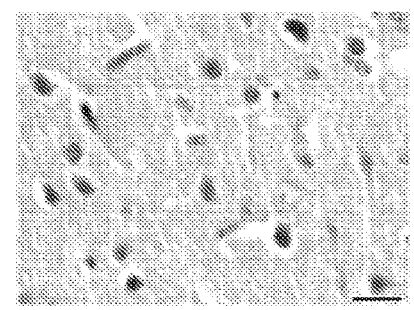 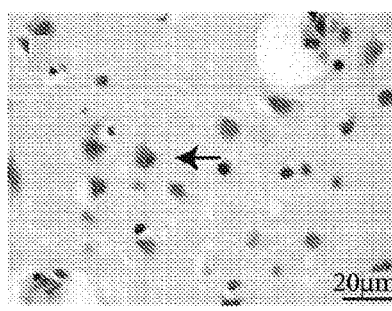
FIG. 20B
FIG. 20C
WM
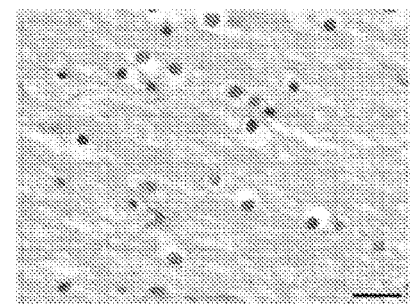 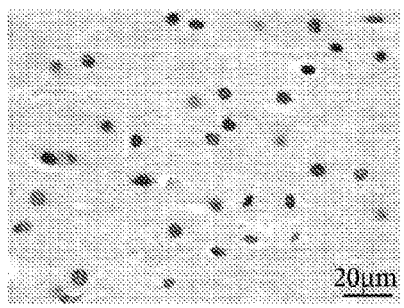
FIG. 20D
α-polyGln in (1C2) Cerebellum
CONTROL | HD
GCL
PCL
FIG. 20E
ML
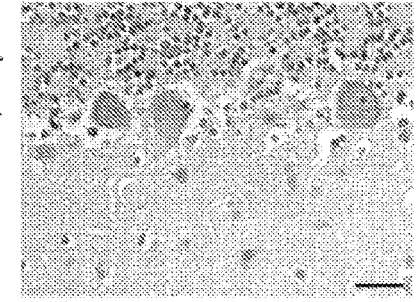 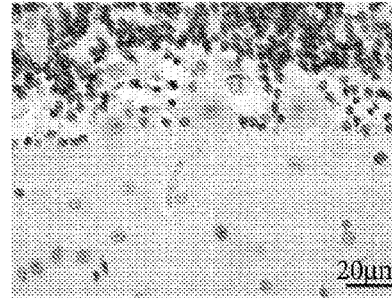
FIG. 20F
FIG. 20G
WM
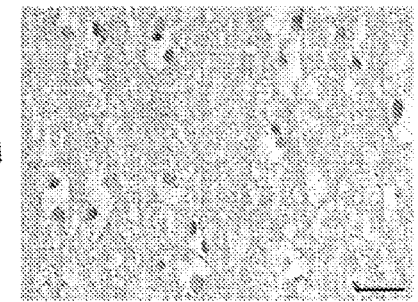 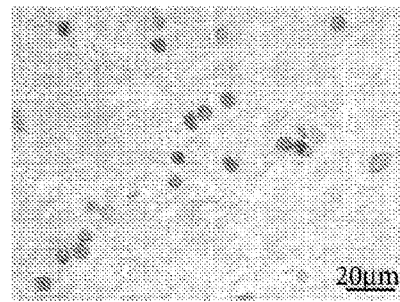
FIG. 20H

α-polySer in cerebellar regions

α-polyCys in cerebellar regions

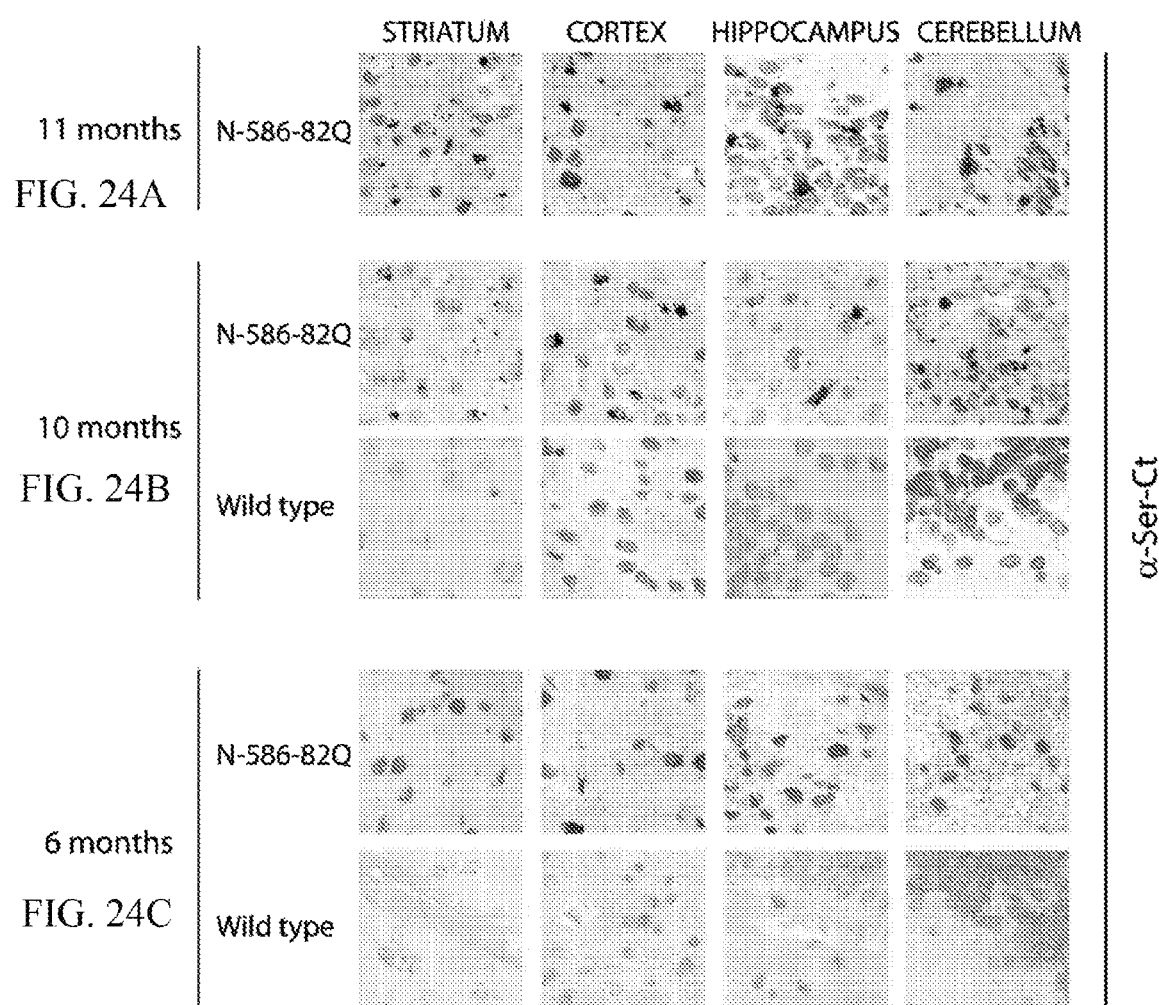

SEQUENCE LISTING

```
Sequence total quantity: 37
SEQ ID NO: 1            moltype = AA  length = 14
FEATURE                 Location/Qualifiers
REGION                  1..14
                        note = Synthetic Polypeptide
source                  1..14
                        mol_type = protein
                        organism = synthetic construct
SEQUENCE: 1
APAAAPAATR PGCG                                                           14

SEQ ID NO: 2            moltype = AA  length = 14
FEATURE                 Location/Qualifiers
REGION                  1..14
                        note = Synthetic Polypeptide
source                  1..14
                        mol_type = protein
                        organism = synthetic construct
SEQUENCE: 2
RPRRHPARLW LRSR                                                           14

SEQ ID NO: 3            moltype = AA  length = 7
FEATURE                 Location/Qualifiers
REGION                  1..7
                        note = Synthetic Polypeptide
source                  1..7
                        mol_type = protein
                        organism = synthetic construct
SEQUENCE: 3
QLPQPPP                                                                    7

SEQ ID NO: 4            moltype = AA  length = 7
FEATURE                 Location/Qualifiers
REGION                  1..7
                        note = Synthetic Polypeptide
source                  1..7
                        mol_type = protein
                        organism = synthetic construct
SEQUENCE: 4
QLPQPPP                                                                    7

SEQ ID NO: 5            moltype = AA  length = 13
FEATURE                 Location/Qualifiers
REGION                  1..13
                        note = Synthetic Polypeptide
source                  1..13
                        mol_type = protein
                        organism = synthetic construct
SEQUENCE: 5
GLGPTRGAAQ HRG                                                            13
```

```
SEQ ID NO: 6              moltype = AA   length = 17
FEATURE                   Location/Qualifiers
REGION                    1..17
                          note = Synthetic Polypeptide
source                    1..17
                          mol_type = protein
                          organism = synthetic construct
SEQUENCE: 6
WKDLRDSKAF ISFSRVA                                                        17

SEQ ID NO: 7              moltype = AA   length = 13
FEATURE                   Location/Qualifiers
REGION                    1..13
                          note = Synthetic Polypeptide
source                    1..13
                          mol_type = protein
                          organism = synthetic construct
SEQUENCE: 7
CAPAAAPAAT RPG                                                            13

SEQ ID NO: 8              moltype = AA   length = 15
FEATURE                   Location/Qualifiers
REGION                    1..15
                          note = Synthetic Polypeptide
source                    1..15
                          mol_type = protein
                          organism = synthetic construct
SEQUENCE: 8
CRPRRHPARL WLRSR                                                          15

SEQ ID NO: 9              moltype = AA   length = 14
FEATURE                   Location/Qualifiers
REGION                    1..14
                          note = Synthetic Polypeptide
source                    1..14
                          mol_type = protein
                          organism = synthetic construct
SEQUENCE: 9
CGLGPTRGAA QHRG                                                           14

SEQ ID NO: 10             moltype = AA   length = 15
FEATURE                   Location/Qualifiers
REGION                    1..15
                          note = Synthetic Polypeptide
source                    1..15
                          mol_type = protein
                          organism = synthetic construct
SEQUENCE: 10
CKDLRDSKAF ISFSR                                                          15

SEQ ID NO: 11             moltype = AA   length = 20
FEATURE                   Location/Qualifiers
REGION                    1..20
                          note = Synthetic Polypeptide
source                    1..20
                          mol_type = protein
                          organism = synthetic construct
SEQUENCE: 11
AAAAAAAAAA AAAAAAAAAA                                                     20

SEQ ID NO: 12             moltype = AA   length = 18
FEATURE                   Location/Qualifiers
REGION                    1..18
                          note = Synthetic Polypeptide
source                    1..18
                          mol_type = protein
                          organism = synthetic construct
SEQUENCE: 12
LLLLLLLLLL LLLLLLLL                                                       18

SEQ ID NO: 13             moltype = AA   length = 20
FEATURE                   Location/Qualifiers
REGION                    1..20
                          note = Synthetic Polypeptide
source                    1..20
                          mol_type = protein
                          organism = synthetic construct
SEQUENCE: 13
```

```
SSSSSSSSSS SSSSSSSSSS                                                  20

SEQ ID NO: 14           moltype = AA  length = 20
FEATURE                 Location/Qualifiers
REGION                  1..20
                        note = Synthetic Polypeptide
source                  1..20
                        mol_type = protein
                        organism = synthetic construct
SEQUENCE: 14
CCCCCCCCCC CCCCCCCCCC                                                  20

SEQ ID NO: 15           moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 15
ggaagatcta acctcctcag cttcctcagc                                       30

SEQ ID NO: 16           moltype = DNA  length = 29
FEATURE                 Location/Qualifiers
misc_feature            1..29
                        note = Synthetic Polynucleotide
source                  1..29
                        mol_type = other DNA
                        organism = synthetic construct
SEQUENCE: 16
cgcggatcct gctgggtcac tctgtctct                                        29

SEQ ID NO: 17           moltype = DNA  length = 31
FEATURE                 Location/Qualifiers
misc_feature            1..31
                        note = Synthetic Polynucleotide
source                  1..31
                        mol_type = other DNA
                        organism = synthetic construct
SEQUENCE: 17
acgcgtcgac gtggaaggac ttgagggact c                                     31

SEQ ID NO: 18           moltype = DNA  length = 29
FEATURE                 Location/Qualifiers
misc_feature            1..29
                        note = Synthetic Polynucleotide
source                  1..29
                        mol_type = other DNA
                        organism = synthetic construct
SEQUENCE: 18
cgcggatccc cgctcaggtt ctgcttttta                                       29

SEQ ID NO: 19           moltype = AA  length = 12
FEATURE                 Location/Qualifiers
REGION                  1..12
                        note = Synthetic Polypeptide
source                  1..12
                        mol_type = protein
                        organism = synthetic construct
SEQUENCE: 19
APAAPAATR PG                                                           12

SEQ ID NO: 20           moltype = AA  length = 14
FEATURE                 Location/Qualifiers
REGION                  1..14
                        note = Synthetic Polypeptide
source                  1..14
                        mol_type = protein
                        organism = synthetic construct
SEQUENCE: 20
RPRRHPARLW LRSR                                                        14

SEQ ID NO: 21           moltype = AA  length = 14
FEATURE                 Location/Qualifiers
REGION                  1..14
                        note = Synthetic Polypeptide
source                  1..14
                        mol_type = protein
                        organism = synthetic construct
```

```
SEQUENCE: 21
KDLRDSKAFI SFSR                                                       14

SEQ ID NO: 22           moltype = AA  length = 13
FEATURE                 Location/Qualifiers
REGION                  1..13
                        note = Synthetic Polypeptide
source                  1..13
                        mol_type = protein
                        organism = synthetic construct
SEQUENCE: 22
GLGPTRGAAQ HRG                                                        13

SEQ ID NO: 23           moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 23
acctcctcag cttcctcagc                                                 20

SEQ ID NO: 24           moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 24
gctgggtcac tctgtctctg                                                 20

SEQ ID NO: 25           moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 25
ctggaacggt gaaggtgaca                                                 20

SEQ ID NO: 26           moltype = DNA  length = 19
FEATURE                 Location/Qualifiers
misc_feature            1..19
                        note = Synthetic Polynucleotide
source                  1..19
                        mol_type = other DNA
                        organism = synthetic construct
SEQUENCE: 26
gggagaggac tgggccatt                                                  19

SEQ ID NO: 27           moltype = DNA  length = 243
FEATURE                 Location/Qualifiers
misc_feature            1..243
                        note = Synthetic
misc_difference         72..243
                        note = may be absent
source                  1..243
                        mol_type = other DNA
                        organism = synthetic construct
SEQUENCE: 27
cagcagcagc agcagcagca gcagcagcag cagcagcagc agcagcagca gcagcagcag     60
cagcagcagc agcagcagca gcagcagcag cagcagcagc agcagcagca gcagcagcag    120
cagcagcagc agcagcagca gcagcagcag cagcagcagc agcagcagca gcagcagcag    180
cagcagcagc agcagcagca gcagcagcag cagcagcagc agcagcagca gcagcagcag    240
cag                                                                  243

SEQ ID NO: 28           moltype = DNA  length = 273
FEATURE                 Location/Qualifiers
misc_feature            1..273
                        note = Synthetic
misc_difference         243..273
                        note = may be absent
source                  1..273
                        mol_type = other DNA
                        organism = synthetic construct
SEQUENCE: 28
```

-continued

```
caacaacaac aacaacaaca acaacaacaa caacaacaac aacaacaaca acaacaacaa    60
caacaacaac aacaacaaca acaacaacaa caacaacaac aacaacaaca acaacaacaa   120
caacaacaac aacaacaaca acaacaacaa caacaacaac aacaacaaca acaacaacaa   180
caacaacaac aacaacaaca acaacaacaa caacaacaac aacaacaaca acaacaacaa   240
caacaacaac aacaacaaca acaacaacaa caa                                273

SEQ ID NO: 29          moltype = DNA   length = 318
FEATURE                Location/Qualifiers
misc_feature           1..318
                       note = Synthetic
source                 1..318
                       mol_type = other DNA
                       organism = synthetic construct
SEQUENCE: 29
gcagcagcag cagcagcagc agcagcagca gcagcagcag cagcagcagc agcagcagca    60
gcagcagcag cagcagcagc agcagcagca gcagcagcag cagcagcagc agcagcagca   120
gcagcagcag cagcagcagc agcagcagca gcagcagcag cagcagcagc agcagcagca   180
gcagcagcag cagcagcagc agcagcagca gcagcagcag cagcagcagc agcagcagca   240
gcagcagcag cagcagcagc agcagcagca gcagcagcag cagcagcagc agcagcagca   300
gcagcagcag cagcagca                                                 318

SEQ ID NO: 30          moltype = DNA   length = 276
FEATURE                Location/Qualifiers
misc_feature           1..276
                       note = Synthetic
source                 1..276
                       mol_type = other DNA
                       organism = synthetic construct
SEQUENCE: 30
tcctcttcct cttcctcttc ctcttcctct tcctcttcct cttcctcttc ctcttcctct    60
tcctcttcct cttcctcttc ctcttcctct tcctcttcct cttcctcttc ctcttcctct   120
tcctcttcct cttcctcttc ctcttcctct tcctcttcct cttcctcttc ctcttcctct   180
tcctcttcct cttcctcttc ctcttcctct tcctcttcct cttcctcttc ctcttcctct   240
tcctcttcct cttcctcttc ctcttcctct tcctct                             276

SEQ ID NO: 31          moltype = DNA   length = 276
FEATURE                Location/Qualifiers
misc_feature           1..276
                       note = Synthetic
source                 1..276
                       mol_type = other DNA
                       organism = synthetic construct
SEQUENCE: 31
cttctccttc tccttctcct tctccttctc cttctccttc tccttctcct tctccttctc    60
cttctccttc tccttctcct tctccttctc cttctccttc tccttctcct tctccttctc   120
cttctccttc tccttctcct tctccttctc cttctccttc tccttctcct tctccttctc   180
cttctccttc tccttctcct tctccttctc cttctccttc tccttctcct tctccttctc   240
cttctccttc tccttctcct tctccttctc cttctc                             276

SEQ ID NO: 32          moltype = DNA   length = 273
FEATURE                Location/Qualifiers
misc_feature           1..273
                       note = Synthetic
source                 1..273
                       mol_type = other DNA
                       organism = synthetic construct
SEQUENCE: 32
tgttgttgtt gttgttgttg ttgttgttgt tgttgttgtt gttgttgttg ttgttgttgt    60
tgttgttgtt gttgttgttg ttgttgttgt tgttgttgtt gttgttgttg ttgttgttgt   120
tgttgttgtt gttgttgttg ttgttgttgt tgttgttgtt gttgttgttg ttgttgttgt   180
tgttgttgtt gttgttgttg ttgttgttgt tgttgttgtt gttgttgttg ttgttgttgt   240
tgttgttgtt gttgttgttg ttgttgttgt tgt                                273

SEQ ID NO: 33          moltype = AA   length = 91
FEATURE                Location/Qualifiers
REGION                 1..91
                       note = Synthetic
source                 1..91
                       mol_type = protein
                       organism = synthetic construct
SEQUENCE: 33
QQQQQQQQQQ QQQQQQQQQQ QQQQQQQQQQ QQQQQQQQQQ QQQQQQQQQQ QQQQQQQQQQ    60
QQQQQQQQQQ QQQQQQQQQQ QQQQQQQQQQ Q                                   91

SEQ ID NO: 34          moltype = AA   length = 105
FEATURE                Location/Qualifiers
REGION                 1..105
                       note = Synthetic
VARIANT                23..105
```

```
                        note = may be absent
source                  1..105
                        mol_type = protein
                        organism = synthetic construct
SEQUENCE: 34
AAAAAAAAAA AAAAAAAAAA AAAAAAAAAA AAAAAAAAAA AAAAAAAAAA AAAAAAAAAA    60
AAAAAAAAAA AAAAAAAAAA AAAAAAAAAA AAAAAAAAAA AAAAA                    105

SEQ ID NO: 35           moltype = AA  length = 105
FEATURE                 Location/Qualifiers
REGION                  1..105
                        note = Synthetic
VARIANT                 24..105
                        note = may be absent
source                  1..105
                        mol_type = protein
                        organism = synthetic construct
SEQUENCE: 35
SSSSSSSSSS SSSSSSSSSS SSSSSSSSSS SSSSSSSSSS SSSSSSSSSS SSSSSSSSSS    60
SSSSSSSSSS SSSSSSSSSS SSSSSSSSSS SSSSSSSSSS SSSSS                    105

SEQ ID NO: 36           moltype = AA  length = 105
FEATURE                 Location/Qualifiers
REGION                  1..105
                        note = Synthetic
VARIANT                 24..105
                        note = may be absent
source                  1..105
                        mol_type = protein
                        organism = synthetic construct
SEQUENCE: 36
LLLLLLLLLL LLLLLLLLLL LLLLLLLLLL LLLLLLLLLL LLLLLLLLLL LLLLLLLLLL    60
LLLLLLLLLL LLLLLLLLLL LLLLLLLLLL LLLLLLLLLL LLLLL                    105

SEQ ID NO: 37           moltype = AA  length = 105
FEATURE                 Location/Qualifiers
REGION                  1..105
                        note = Synthetic
VARIANT                 24..105
                        note = may be absent
source                  1..105
                        mol_type = protein
                        organism = synthetic construct
SEQUENCE: 37
CCCCCCCCCC CCCCCCCCCC CCCCCCCCCC CCCCCCCCCC CCCCCCCCCC CCCCCCCCCC    60
CCCCCCCCCC CCCCCCCCCC CCCCCCCCCC CCCCCCCCCC CCCCC                    105
```

METHODS FOR DIAGNOSING HUNTINGTON'S DISEASE

RELATED APPLICATIONS

This Application is a Continuation of U.S. application Ser. No. 16/695,717, filed Nov. 26, 2019, entitled "METHODS FOR DIAGNOSING HUNTINGTON'S DISEASE", which is a Continuation of U.S. application Ser. No. 15/577,995, filed Nov. 29, 2017, entitled "METHODS FOR DIAGNOSING HUNTINGTON'S DISEASE", which is a national stage filing under 35 U.S.C. 371 of International Patent Application Serial No. PCT/US2016/034738, filed May 27, 2016, entitled "METHODS FOR DIAGNOSING HUNTINGTON'S DISEASE", which claims the benefit of 35 U.S.C. 119(e)) of U.S. provisional application Ser. No. 62/168,695, filed May 29, 2015, entitled "Methods for Diagnosing Huntington's Disease". The entire contents of these applications are incorporated herein by reference in their entirety.

REFERENCE TO AN ELECTRONIC SEQUENCE LISTING

The contents of the electronic sequence listing (U120270063US03-SUBSEQ-KZM.xml; Size: 51,742 bytes; and Date of Creation: May 8, 2023) is herein incorporated by reference in its entirety.

BACKGROUND

Huntington's Disease (HD) is a progressive neurodegenerative disease characterized by severe movement, cognitive, and behavioral changes caused by a CAG·CTG expansion in the Htt gene. Upon translation, this expansion mutation results in the production of huntingtin protein (HTT) with an expanded poly-Glutamine (polyGln, polyQ) repeat tract, which is toxic and contributes to disease pathology. While pre-symptomatic genetic testing for HD can identify the presence of disease-causing mutant Htt, a positive test does not necessarily indicate the initiation of the pathogenic process. Currently utilized HD therapies are limited to reduction of symptoms and do not provide a cure. Accordingly, novel compositions and methods for diagnosis and treatment of HD are needed.

SUMMARY

In some aspects, the disclosure relates to methods and compositions for the diagnosis and treatment of Huntington's disease. The disclosure is based, in part, on the discovery that four repeat associated non-ATG translation proteins (also referred to as RAN proteins)-polyAlanine, polySerine, polyLeucine, and polyCysteine (polyAla, polySer, polyLeu and polyCys, respectively)-accumulate in the brains of subjects having Huntington's disease and that these RAN proteins can be detected in a biological sample (e.g., blood, serum, or cerebrospinal fluid (CSF)) of a subject having or at risk of developing HD.

RAN proteins were known to be associated with HD. However, the presence of HD-associated RAN proteins in some samples (e.g., blood and CSF) has been uncertain or difficult to detect reproducibly. The present work shows that such RAN proteins are indeed present in certain samples (e.g., blood and CSF) obtained from subjects having HD or at risk for HD, but one or more antigen retrieval techniques are required to detect the RAN proteins in such samples reproducibly.

Accordingly, in some embodiments, the disclosure provides a method for diagnosing Huntington's disease, the method comprising: detecting in a biological sample obtained from a subject at least one RAN protein (e.g., after using one or more antigen retrieval techniques), wherein the RAN protein is not polyGln; diagnosing the subject as having Huntington's disease based upon the presence of the at least one RAN protein.

In some aspects, the disclosure provides a method for treating Huntington's disease in a subject, the method comprising: administering to a subject a therapeutic for the treatment of Huntington's disease, wherein the subject has been characterized as having Huntington's disease by the detection of at least one RAN protein in a biological sample obtained from the subject (e.g., after using one or more antigen retrieval techniques), wherein the RAN protein is not polyGln.

In some embodiments of methods described by the disclosure, the biological sample is blood or cerebrospinal fluid (CSF). In some embodiments, the RAN protein is poly-Alanine, poly-Leucine, poly-Serine, or poly-Cysteine.

In some embodiments of methods described by the disclosure, an antigen retrieval method is performed on the biological sample prior to the detecting. In some embodiments, the antigen retrieval method is heat-induced epitope retrieval (HIER). In some embodiments, the antigen retrieval method comprises protease-induced epitope retrieval (PIER). In some embodiments, the antigen retrieval method comprises heat-induced epitope retrieval (HIER) and protease-induced epitope retrieval (PIER). In some embodiments, an antigen retrieval method comprises formic acid treatment, pressure treatment, heat treatment, or any combination of the foregoing.

In some embodiments, the number of poly-amino acid repeats in the at least one RAN protein is greater than or equal to 35. In some embodiments, the number of poly-amino acid repeats in the at least one RAN protein is greater than or equal to 45. In some embodiments, the number of poly-amino acid repeats in the at least one RAN protein is greater than or equal to 50. In some embodiments, the number of poly-amino acid repeats in the at least one RAN protein is greater than or equal to 70.

In some embodiments of methods described by the disclosure, detecting of one or more RAN proteins is performed by immunoblot analysis, Western blot analysis, immunohistochemistry, or ELISA (e.g., after using one or more antigen retrieval techniques). In some embodiments, the Western blot analysis comprises contacting a sample (e.g., a biological sample) with an anti-RAN antibody. In some embodiments, the anti-RAN antibody targets poly-Alanine, poly-Leucine, poly-Serine, or poly-Cysteine. In some embodiments, the anti-RAN antibody targets the C-terminus of a RAN protein.

In some embodiments, methods described by the disclosure further comprise administering to the subject a therapeutic for the treatment of Huntington's disease. In some embodiments, the therapeutic is an antisense oligonucleotide. In some embodiments, the antisense oligonucleotide targets a HTT gene. In some embodiments, the antisense oligonucleotide inhibits translation of one or more RAN proteins. In some embodiments, the therapeutic is a DNA or RNA aptamer that targets a HTT gene. In some embodiments, the therapeutic is an anti-RAN antibody, for example an anti-RAN antibody that targets the C-terminus of a RAN protein.

In some embodiments, the disclosure provides a method for diagnosing Huntington's disease, the method comprising: a) obtaining a biological sample (e.g., blood, serum, CSF, etc.) from a subject (e.g., a human subject); b) contacting the biological sample with a set of anti-RAN antibodies (e.g., α-polyAla, α-polyLeu, α-polySer, α-polyCys, or a combination of two, three or four of the foregoing), optionally after using one or more antigen retrieval techniques; c) detecting the presence of one or more RAN proteins in the sample based on the binding of the anti-RAN antibodies to the one or more RAN proteins (e.g., by immunoblot, immunohistochemistry, ELISA, etc.); d) diagnosing the subject as having Huntington's disease based upon the presence of the at least one RAN protein in the biological sample.

In some embodiments, the disclosure provides a method for detecting Huntington's disease-associated RAN proteins, the method comprising: a) obtaining a biological sample (e.g., blood, serum, CSF, etc.) from a subject (e.g., a human subject); b) contacting the biological sample with a set of anti-RAN antibodies (e.g., α-polyAla, α-polyLeu, α-polySer, α-polyCys, or a combination of two, three or four of the foregoing), optionally using one or more antigen retrieval techniques; and, c) detecting the presence of one or more RAN proteins in the sample based on the binding of the anti-RAN antibodies to the one or more RAN proteins (e.g., by immunoblot, immunohistochemistry, ELISA, etc.).

BRIEF DESCRIPTION OF DRAWINGS

FIG. 1A shows a series of minigenes containing HTT exon 1 with expansion mutations. FIG. 1B shows an ATG initiation codon is not required for expression of the polyGln, polyAla or polySer expansion proteins. FIG. 1C shows a panel of polyclonal antibodies against the predicted C-terminal regions available for four of the five possible novel RAN proteins were generated; SEQ ID NO: 1-6 are depicted in FIG. 1C (top to bottom). FIG. 1D shows positive staining of striatum using four HD-RAN antibodies: α-Ala-Ct, α-Ser-Ct, α-Leu-Ct, α-Cys-Ct. FIG. 1E shows protein blot analyses of insoluble lysates from frontal cortex indicate that RAN proteins accumulate in HD but not control brains. Ct=C-terminal.

FIG. 2A shows control and HD brain showing striatal sub-regions with summary of staining. FIG. 2B shows quantification of IHC-positive cells for α-Gln, α-RAN, and IBA1 staining±SEM in caudate nucleus. FIGS. 2C-2I show IHC of striatal sub-sections from HD brains using (FIG. 2C) α-Gln antibody (1C2), (FIGS. 2D-2G) α-RAN antibodies, (FIG. 2H) α-IBA1 for microglia, and (FIG. 2I) α-active caspase-3 for cell death. FIG. 2J shows double staining for RAN protein cocktail using mixture of all four anti-RAN antibodies plus anti-IBA1 antibody to label microglia with quantitation (±SEM) of single-, double-labeled, and IBA1 cells that are in close proximity to RAN-positive cells. FIG. 2K shows double staining for RAN protein cocktail using mixture of all anti-RAN antibodies plus anti-caspase-3 antibody to label apoptotic cells with quantitation of the percent active Caspase-3-positive cells that are also positive for RAN proteins. Cau-WMB, caudate white matter bundles; Int-Cap, internal capsule; Put-WMB, putamen white matter bundles.

FIGS. 3A and 3B show IHC staining of control and HD gray and white matter of (FIG. 3A) frontal cortex and (FIG. 3B) cerebellum using α-RAN and α-Gln (1C2) antibodies show punctate nuclear and cytoplasmic staining with α-polyAla, α-polySer, α-polyLeu, and α-polyCys. GCL, granule cell layer; PCL, Purkinje-cell layer; ML, molecular layer. Staining of the cortex and cerebellum in adult-onset HD cases is variable. IHC images and quantification of percent positive cells represent typical positive regions. FIG. 3C shows IHC staining of indicated brain regions in N171-82Q and control mice using the α-polyAla, α-polySer. Red, positive staining; blue, nuclear counterstain.

FIG. 4A shows CAG and CAA HTT-exonl minigenes. FIG. 4B shows immunoblots and FIG. 4C shows immunofluorescence (IF) of HEK293Tcells after transfection with indicated constructs. FIG. 4D shows transfected minigenes (top) containing non hairpin-forming alternative codons in the repeat region for polyGln90 (CAA), polySer90 (TCC-TCT), polyLeu90 (CTT-CTC), and polyCys90 (TGT) constructs. Since non-hairpin forming codon substitutions encoding polyAla were not available, polyAla was expressed by a +ATG-GCA construct using a slightly longer repeat tract of 105 repeats. FIGS. 4E and 4F show LDH assays of SH-SYSY and T98 cells expressing polyGln and individual HD-RAN proteins 42 hr post-transfection. Values equal percent of cell death±SEM (n=5; *$p<0.05$, $p<0.01$, and *$p<0.001$).

FIG. 5A shows a schematic diagram summarizing features of adult-onset and juvenile HD pathology. FIG. 5B shows H&E staining in control, adult-onset, and juvenile-onset HD cases with cerebellar atrophy. FIG. 5C shows α-polyGln, α-polySer, α-polyCys and α-IBA1 staining in cerebellar layers. FIG. 5D shows quantitation of IHC-positive cells with 1C2 (polyGln) and α-polySer-Ct, α-polyCys-Ct, and α-IBA1 antibodies. WM, white matter; GCL, granule cell layer; PCL, Purkinje-cell layer; ML, molecular layer. Red, positive staining; blue, nuclear counterstain. Staining of cerebellum in adult-onset HD cases is variable. IHC images and quantification of percent positive cells represent typical positive regions.

FIG. 7A shows IF showing (+)ATG and RAN proteins expressed in cells transfected with 23 or 80 CAG or 80 CAA repeat constructs+/−ATG (Gln frame). PolyGln is expressed from all constructs with an ATG in the polyGln reading frame (23 & 80 CAGs and 80 CAAs). RAN-polyGln is also expressed with 80 CAG repeats from ATG(−) minigene. RAN PolyAla shows diffuse cytoplasmic staining, RAN polySer forms multiple cytoplasmic aggregates and ATG/RAN polyGln shows nuclear and cytoplasmic staining. The minigene with 80 CAA repeats expressed ATG-polyGln but not RAN proteins in the other two reading frames. FIG. 7B shows protein blots of HEK293T cells transfected with non-hairpin forming CAA constructs+/−ATG (Gln frame). Protein expression is detected in the polyGln reading frame with the +ATG CAA construct but not in alternative CAA reading frames (Asn or Thr). FIG. 7C shows immunoprecipitation of lysates from HEK293T cells transfected with HTTexon1 minigenes with a 5'V5 N-terminal tag in the glutamine frame and 3 C-terminal tags in each reading frame. IPs using antibodies against C-terminal epitope tags in the polyAla and polySer frames are not positive for the N-terminal V5-Tag in the polyGln frame.

FIGS. 8A-8D show validation of novel antibodies against C-terminal regions of putative HD-RAN polyAla, polySer, polyLeu and polyCys proteins. FIGS. 8A-8D show constructs used to express flag-tagged proteins with endogenous C-terminal regions, with sequences of peptides used to generate C-terminal antibodies indicated; SEQ ID NO: 7 is depicted in the FLAG-Ala-Ct construct, SEQ ID NO: 8 is depicted in the FLAG-Ser-Ct construct, SEQ ID NO:9 is depicted in the FLAG-Leu-Ct construct, SEQ ID NO: 10 is depicted in the FLAG-Cys-Ct construct. HEK293T lysates assayed by protein blot (left) show detection of recombinant proteins by α-Flag and HD-RAN antibodies. The polyAla and polyLeu expansion proteins run as high-MW smears and the polySer expansion runs at the top of the gel. Aberrant migration patterns suggest that the homopolymeric expansion proteins are insoluble and aggregation prone. IF was performed on cells transfected with Flag-Ala(104 repeats), Flag-Ser (23 repeats), Flag-Leu (104 repeats) and Flag-Cys (23 repeats) and shows co-localization of α-Flag and newly developed HD-RAN C-terminal antibodies, α-polyAla-Ct, α-polySer-Ct, α-polyLeu-Ct and α-polyCys-Ct.

FIGS. 9A-9E show RAN-polyAla staining in striatal brain regions. IHC shows α-polyAla positive cells inhuman HD caudate (FIG. 9A) and putamen (FIG. 9E). α-polyAla staining is particularly abundant in the white matter bundles of both caudate and putamen (FIG. 9B, FIG. 9D). Internal capsule (FIG. 9C) is negative for α-polyAla staining.

FIGS. 10A-10E show RAN-polySer staining in striatal brain regions. IHC shows α-polySer staining in caudate and putamen of the striatum and in the white matter bundles (FIG. 10A, FIG. 10B, FIG. 10D, FIG. 10E) of HD but not control autopsy samples. Staining is not found in the internal capsule (FIG. 10C). Poly-Ser localizes in both nucleus and cytoplasm.

FIGS. 11A-11E show RAN-PolyLeu nuclear staining in HD striatum. IHC shows α-polyLeu nuclear staining in caudate, putamen and white matter bundles in human HD but not control autopsy tissue (FIG. 11A, FIG. 11B, FIG. 11D, FIG. 11E). In contrast, similar staining was not found in the internal capsule (FIG. 11C).

FIGS. 12A-12E show RAN PolyCys staining in HD striatum. IHC shows α-polyCys staining in caudate, putamen and white matter bundles in human HD but not control autopsy tissue (FIG. 12A, FIG. 12B, FIG. 12D, FIG. 12E). Similar staining was not found in the internal capsule (FIG. 12C). α-polyCys staining was nuclear or cytoplasmic within tense punctate staining seen in some cells.

FIGS. 13A-13E show 1C2 staining shows nuclear and cytoplasmic polyGln aggregates in HD but not control caudate and putamen (FIG. 13A, FIG. 13E). Staining was negative in white matter bundles of the caudate and putamen (FIG. 13B, FIG. 13D) and internal capsule (FIG. 13C) at the experimental conditions tested. Comparable results were obtained using the EM48 antibody to detect HTT polyGln aggregates. Arrows highlight positive staining. 1C2 positive cell in sub-panel FIG. 13D is located outside the circular white matter bundle region.

FIGS. 14A-14E show IBA1-positive staining in HD striatum. IHC immunostaining for microglia/macrophages with α-IBA1 shows strong immunostaining, similar to HD-RAN antibody staining, with positive signal in HD but not control caudate, putamen and white-matter bundles (FIG. 14A, FIG. 14B, FIG. 14D, FIG. 14E). Staining was not detected in the internal capsule (FIG. 14C).

FIGS. 15A-15E show active Caspase 3 staining in RAN-positive regions of the HD striatum. IHC shows frequent active Caspase3 signal in caudate, putamen, and white matter bundles (FIG. 15A, FIG. 15B, FIG. 15D, FIG. 15E) of HD but not control striatum. Internal capsule also shows α-Caspase 3 positive cells (FIG. 15C).

FIGS. 16A-16H show PolyAla RAN proteins in HD frontal cortex and cerebellum. IHC staining shows positives-polyAla staining in grey and white matter of HD (FIG. 16B, FIG. 16D) but not control (FIG. 16A, FIG. 16C) frontal cortex. Similarly, α-polyAla staining was found in cerebellar granular cell layer, molecular layer and deep white-matter regions of the cerebellum in HD (FIG. 16F, FIG. 16H) but not control samples (FIG. 16E, FIG. 16G). GM=grey matter, WM=white matter, GCL=granule-cell layer, PCL=Purkinje-cell layer, ML=molecular layer.

FIGS. 17A-17H show PolySer RAN proteins in HD frontal cortex and cerebellum. Grey and white matter regions of the frontal cortex show positive α-polySer staining (FIG. 17B, FIG. 17D) in HD but not control (FIG. 17A, FIG. 17C) autopsy tissue. Cerebellar granular layer, molecular layer and white matter regions also show positive staining for α-polySer in HD (FIG. 17F, FIG. 17H) but not control (FIG. 17E, FIG. 17G) samples. GM=grey matter, WM=white matter, GCL=granule-cell layer, PCL=Purkinje-cell layer, ML=molecular layer.

FIGS. 18A-18L show PolyLeu RAN proteins in HD frontal cortex and cerebellum. Grey and white matter regions of HD (FIG. 18B, FIG. 18D, FIGS. 18E-18H) but not control (FIG. 18A, FIG. 18C) frontal cortex show positive nuclear and cytoplasmic IHC staining with α-polyLeu in HD. In the cerebellum, α-Leu-Ct staining is found in the granular and molecular layers (FIG. 18J) and white matter (FIG. 18L) in HD but not control (FIG. 18I, FIG. 18K) samples. Diffuse and punctate staining patterns are detected in both the cytoplasm and the nucleus in the frontal cortex (FIG. 18E-FIG. 18H). GM=grey-matter, WM=white matter, GCL=granule-cell layer, PCL=Purkinje-cell layer, ML=molecular layer.

FIGS. 19A-19H show PolyCys RAN proteins in HD frontal cortex and cerebellum. IHC staining shows polyCys positive cells in grey and white matter of HD (FIG. 19B, FIG. 19D) but not control (FIG. 19A, FIG. 19C) frontal cortex. (FIGS. 19E-19H show PolyCys staining shows nuclear accumulation in the cerebellar granular layer and cytoplasmic aggregation in the molecular layer of the cerebellum in HD samples. GM=grey matter, WM=white matter, GCL=granule-cell layer, PCL=Purkinje-cell layer, ML=molecular layer.

FIGS. 20A-20H show PolyGln positive staining in HD frontal cortex (FIGS. 20A-20D) and cerebellum (FIGS. 20E-20H). IHC staining shows polyGln (1C2)-positive neurons in grey matter of HD frontal cortex (top). Subcortical white matter was negative for polyGln in the cases analyzed. Cerebellar tissue didn't show polyGln aggregates at the experimental conditions tested (bottom). GM=grey matter, WM=white matter, GCL=granule-cell layer, PCL=Purkinje-cell layer, ML=molecular layer.

FIG. 21A shows IF (HEK293T cells) showing length dependent accumulation of CAG-encoded HD-RAN proteins in cells transfected with HTT-exon1 constructs. CAG-expanded constructs express polyGln, polyAla and polySer proteins+/−ATG initiation codon. ATG initiated CAA-expanded HTTexon1 constructs only express polyGln protein. FIG. 21 B shows percent cell death of HEK293T cells transfected with ATG initiated non-hairpin forming codon-substitution minigenes for HD polyGln, polySer, polyLeu, polyCys and ATG initiated GCA encoded polyAla. Bar graph shows relative cell toxicity 42 hours after transfection evaluated by LDH assay±SEM (n=5). FIG. 21C shows (top panels) immunoblots showing protein expression in SH-SY5Y, T98 and HeK293T cells transfected with indicated constructs. PolySer, polyLeu and polyCys codon substitution constructs express single proteins while the ATG(+)-polyAla GCA construct shows robust polyAla and lower levels of RAN polyGln and RAN polySer in HEK293T and T98 (indicated with *). FIG. 21C (bottom panels) shows qRT-PCR showing transcript levels±SEM (n=3) are comparable with no significant difference between constructs. FIGS. 21D-21F show percent death (±SEM) of SH-SY5Y (FIG. 21D), T98 (FIG. 21E) and HEK293T (FIG. 21F) cells after transfection w/constructs expressing individual HD proteins at indicated vector doses and times post transfection using LDH assays (n=5).

FIGS. 24A-24C show PolySer HD RAN protein accumulation increases with age and disease in HD transgenic N586-82Q mice. Immunohistochemistry showing RAN polySer staining in different brain regions of N586-82Q HD mice at 11 (FIG. 24A), 10 (FIG. 24B) and 6 (FIG. 24C) months of age. PolySer accumulation increases with age. No similar signal was detected in wild type littermates.

FIG. 27B shows immunofluorescence images showing an example of HD-poly Ser staining detected in HD lymphocytes but not controls.

DETAILED DESCRIPTION

Figure 1A:
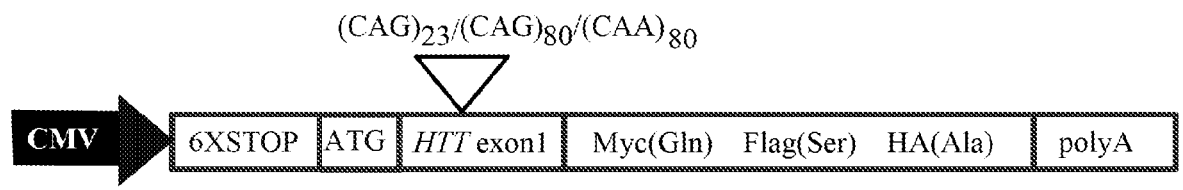
FIGS. 1A-1E show RAN translation can occur across the HTT open reading frame (ORF).
Figure 1B:
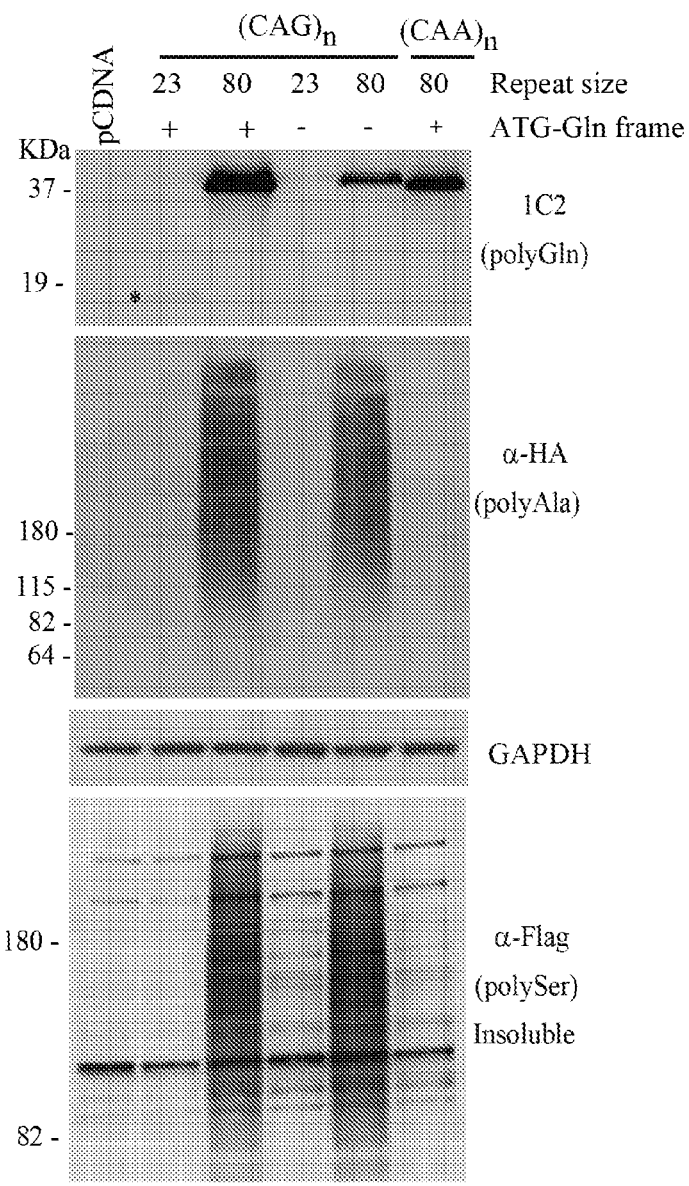

The disclosure provides methods and compositions for the diagnosis and treatment of Huntington's disease (HD).

In some aspects, the disclosure provides a method of diagnosing Huntington's disease, the method comprising: detecting in a biological sample obtained from a subject at least one RAN protein (e.g., after using one or more antigen retrieval techniques), wherein the RAN protein is not polyGln, and diagnosing the subject as having Huntington's disease based upon the presence of the at least one RAN protein.

The disclosure is based, in part, on the discovery that repeat-associated non-ATG (RAN) proteins other than poly-Glutamine (e.g., poly-Alanine, poly-Leucine, poly-Serine, poly-Cysteine) are expressed and are detectable in biological samples of subjects having or suspected of having Huntington's disease (HD) (e.g., after using one or more antigen retrieval techniques on the biological sample). Biological samples can be any specimen derived or obtained from a subject having or suspected of having HD. In some embodiments, the biological sample is blood, serum (e.g., plasma from which the clotting proteins have been removed) or cerebrospinal fluid. However, the skilled artisan will recognize other suitable biological samples, such as tissue (e.g., brain tissue, spinal tissue, etc.) and cells (e.g., brain cells, neuronal cells, skin cells, etc.).

A "subject having or suspected of having Huntington's disease" can be a subject that is known or determined to have more than 35 CAG repeats in the HTT gene, or a subject exhibiting signs and symptoms of HD, including but not limited to motor dysfunction (e.g., chorea), diminished executive functions (e.g., cognitive flexibility and abstract thinking), and/or neuropsychiatric manifestations (e.g., compulsive behavior, apathy, anxiety). A subject can be a mammal (e.g., human, mouse, rat, dog, cat, or pig). In some embodiments, the subject is a human.

Generally, the disease status of a subject having or suspected of having HD is classified by the number of CAG repeats present (e.g., detected) in a HTT gene of the subject. Typically, a HTT gene having less than 36 trinucleotide (CAG) repeats produces non-pathogenic cytoplasmic Huntingtin protein. A subject having between 36 and 39 trinucleotide repeats produces mutant Huntingtin protein that is shorter than fully pathogenic forms, and may or may not develop disease. A subject having more than 40 trinucleotide repeats is classified as having fully penetrant HD and will eventually develop HD, also referred to as adult-onset HD. In certain cases of fully penetrant HD characterized by large (>100) repeats, subject can develop juvenile-onset HD, also referred to as akinetic-rigid, or Westphal variant HD. In some embodiments, a subject has or is suspected of having adult-onset HD. In some embodiments, a subject has or is suspected of having juvenile-onset HD.

RAN Proteins

A "RAN protein (repeat-associated non-ATG translated protein)" is a bidirectionally transcribed polypeptide a polypeptide translated from mRNA sequence carrying a nucleotidic expansion in the absence of an AUG initiation codon. Generally, RAN proteins comprise expansion repeats of an amino acid, termed poly amino acid repeats. For example, "AAAAAAAAAAAAAAAAAAAA" (poly-Alanine) (SEQ ID NO: 11), "LLLLLLLLLLLLLLLLLLLL" (poly-Leucine) (SEQ ID NO: 12), "SSSSSSSSSSSSSSSSSSSS" (poly-Serine) (SEQ ID NO: 13), or "CCCCCCCCCCCCCCCCCCCC" (poly-Cysteine) (SEQ ID NO: 14) are poly amino acid repeats that are each 20 amino acid residues in length. RAN proteins can have a poly amino acid repeat of at least 25, at least 30, at least 40, at least 50, at least 60, at least 70, at least 80, at least 90, at least 100, or at least 200 amino acid residues in length. In some embodiments, a RAN protein has a poly amino acid repeat more than 200 amino acid residues in length.

In some aspects, the disclosure relates to the discovery that RAN protein (e.g., poly-Alanine, poly-Leucine, poly-Serine) aggregation patterns are length-dependent. For example, RAN proteins having poly amino acid repeats that are >20, >48, or >80 residues in length aggregate differently in the brain of a subject. Generally, the differential aggregation properties of RAN proteins having different lengths can be used to detect RAN proteins in a biological sample. Longer RAN proteins are found at higher levels in biological samples, such as blood, serum, or CSF. In some embodiments, RAN proteins having poly amino acid repeats >40, >50, >60, >70, or >80 amino acid residues in length are detectable in a biological sample by Western Blot.

In some embodiments, the presence or molecular weight of poly amino acid repeat proteins (e.g., RAN proteins) can be difficult to determine by Western blot. This disclosure is based, in part, on the discovery that RAN proteins having poly amino acid repeats above a threshold length are detectable (e.g., by Western blot). In some embodiments, if the presence of a RAN protein (e.g., poly-Alanine, poly-Serine, poly-Leucine, or poly-Cysteine) is detected (for example, with or without determining the length of the RAN protein) in a biological sample from a subject (e.g., by Western blot), the subject is identified as having a HTT poly amino acid repeat of at least 40, at least 50, at least 60, at least 70, or at least 80 residues in length.

Detection of RAN Proteins

In some embodiments, the tissue distribution of one or more RAN proteins can be used to diagnose a subject as having HD or to detect the presence or severity of HD in a subject.

The disclosure is based, in part, on the discovery that certain biological sample processing methods (e.g., antigen retrieval methods) enable the reproducible detection of one or more RAN proteins in a biological sample. In some embodiments of methods described by the disclosure, a sample (e.g., a biological sample) is treated by an antigen retrieval process to render the one or more antigens within the sample accessible to detection agents (e.g., antibodie(s)). As used herein, "antigen retrieval" (also referred to as epitope retrieval, or antigen unmasking) refers to a process in which a biological sample (e.g., blood, serum, CSF, etc.) are treated under conditions which expose antigens (e.g., epitopes) that were previously inaccessible to detection agents (e.g., antibodies, aptamers, and other binding molecules) prior to the process. Generally, antigen retrieval methods comprise steps including but not limited to heating, pressure treatment, enzymatic digestion, treatment with reducing agents, treatment with oxidizing agents, treatment with crosslinking agents, treatment with denaturing agents (e.g., detergents, ethanol, acids), or changes in pH, or any combination of the foregoing. Several antigen retrieval methods are known in the art, including but not limited to protease-induced epitope retrieval (PIER) and heat-induced epitope retrieval (HIER). In some embodiments, antigen retrieval procedures reduce the background and increase the sensitivity of detection techniques (e.g., immunohistochemistry (IHC), immuno-blot (such as Western Blot), ELISA, etc.).

For example, in some embodiments, antigen retrieval techniques increase reproducibility of detection of RAN proteins by reducing instances of false positives and allowing the detection of "positive" samples with low levels of our target protein that may not otherwise be identified as "positive". In some embodiments, an antigen retrieval process is performed on the biological sample prior to detection of one or more RAN proteins (e.g., detection by immuno-blot, such as Western blot, immunohistochemistry, ELISA, etc.).

In some embodiments, detection of RAN proteins in a biological sample is performed by Western blot. Western blots generally employ the use of a detection agent or probe to identify the presence of a protein or peptide. In some embodiments, detection of one or more RAN proteins is performed by immunoblot (e.g., dot blot, 2-D gel electrophoresis, etc.), immunohistochemistry (IHC), or ELISA. In some embodiments, the detection agent is an antibody. In some embodiments, the antibody is an anti-RAN protein antibody, such as anti-poly-Alanine, anti-poly-Serine, anti-poly-Leucine, or anti-poly-Cysteine (also referred to as α-polyAla, α-polySer, α-polyLeu, α-polyCys). Anti-RAN antibodies may target any portion of a RAN protein that does not comprise the poly amino acid repeat. In some embodiments, an anti-RAN antibody (e.g., α-polyAla, α-polySer, α-polyLeu, α-polyCys) targets the C-terminus of a RAN protein (e.g., the C-terminus of a RAN protein described in the Examples below). Examples of anti-RAN antibodies targeting the C-terminus of RAN protein are disclosed, for example, in U.S. Publication No. 2013/0115603, the entire content of which is incorporated herein by reference. In some embodiments a set (or combination) of anti-RAN antibodies (e.g., a combination of two or more anti-RAN antibodies selected from α-poly-Ala, α-poly-Ser, α-poly-Leu, and α-poly-Cys) is used to detect one or more RAN proteins in a biological sample.

In some embodiments, the detection agent is an aptamer (e.g., RNA aptamer, DNA aptamer, or peptide aptamer). In some embodiments, an aptamer specifically binds to a RAN protein (e.g., polyAla, polySer, polyLeu, polyCys).

An anti-RAN antibody can be a polyclonal antibody or a monoclonal antibody. Typically, polyclonal antibodies are produced by inoculation of a suitable mammal, such as a mouse, rabbit or goat. Larger mammals are often preferred as the amount of serum that can be collected is greater. An antigen is injected into the mammal. This induces the B-lymphocytes to produce IgG immunoglobulins specific for the antigen. This polyclonal IgG is purified from the mammal's serum. Monoclonal antibodies are generally produced by a single cell line (e.g., a hybridoma cell line). In some embodiments, an anti-RAN antibody is purified (e.g., isolated from serum).

Numerous methods may be used for obtaining anti-RAN antibodies. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody that specifically binds with a specified antigen. Any form of the specified antigen (e.g., a RAN protein) may be used as the immunogen, e.g., recombinant antigen, naturally occurring forms, any variants or fragments thereof. One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597WO92/18619; WO 91/17271; WO 92/20791; WO 92/15679; WO 93/01288; WO 92/01047; WO 92/09690; and WO 90/02809.

In addition to the use of display libraries, the specified antigen (e.g., one or more RAN proteins) can be used to immunize a non-human animal, e.g., a rodent, e.g., a mouse, hamster, or rat. In one embodiment, the non-human animal is a mouse.

In another embodiment, a monoclonal antibody is obtained from the non-human animal, and then modified, e.g., made chimeric, using recombinant DNA techniques known in the art. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

Antibodies can also be humanized by methods known in the art. For example, monoclonal antibodies with a desired binding specificity can be commercially humanized (Scotgene, Scotland; and Oxford Molecular, Palo Alto, Calif.). Fully humanized antibodies, such as those expressed in transgenic animals are within the scope of the invention (see, e.g., Green et al. (1994) Nature Genetics 7, 13; and U.S. Pat. Nos. 5,545,806 and 5,569,825).

For additional antibody production techniques, see Antibodies: A Laboratory Manual, Second Edition. Edited by Edward A. Greenfield, Dana-Farber Cancer Institute, ©2014. The present disclosure is not necessarily limited to any particular source, method of production, or other special characteristics of an antibody.

Therapeutic Methods

Methods of treating HD are also contemplated by the disclosure. In some embodiments, a subject having been diagnosed with HD by a method described by the disclosure is administered a therapeutic useful for treating HD. A therapeutic useful for treating HD can be a small molecule, protein, peptide, nucleic acid, or gene therapy vector (e.g., viral vector encoding a therapeutic protein). In some embodiments, the therapeutic is an antisense oligonucleotide. In general, antisense oligonucleotides block the translation of a target protein by hybridizing to an mRNA sequence encoding the target protein, thereby inhibiting protein synthesis by ribosomal machinery. In some embodiments, the antisense oligonucleotide targets the Huntington (HTT) gene. In some embodiments, the antisense oligonucleotide inhibits translation of one or more RAN proteins.

In some embodiments, the therapeutic is an antibody, such as an anti-RAN antibody. In some embodiments, the anti-RAN antibody targets the C-terminus of a RAN protein (e.g., polyAla, polySer, polyLeu, polyCys). In some embodiments, the therapeutic is a small molecule, such as tetrabenazine, haloperidol, chlorpromazine, risperidone, quetiapine, amantadine, levetiracetam, clonazepam, citalopram, fluoxetine, sertraline, olanzapine, alproate, carbamazepine, lamotrigine, cysteamine, PB T2, PDE10A inhibitor, pridopidine, and laquinimod.

In some embodiments, methods of detecting one or more RAN proteins in a biological sample are useful for monitoring the progress of HD treatment. For example, in some embodiments, biological samples are obtained from a subject prior to and after (e.g., 1 week, 2 weeks, 1 month, 6 months, or one year after) commencement of a HD therapeutic regimen and the amount of RAN proteins detected in the samples is compared. In some embodiments, if the level (e.g., amount) of RAN protein in the post-treatment sample is reduced compared to the pre-treatment level (e.g., amount) of RAN protein, the therapeutic regimen is successful. In some embodiments, the level of RAN proteins in biological samples (e.g., 1, 2, 3, 4, 5, 6, 7, 8, 9, 10, or more samples) of a subject are continuously monitored during a HD therapeutic regimen (e.g., measured on 1, 2, 3, 4, 5, 6, 7, 8, 9, 10, or more separate occasions).

The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Example 1: RAN Translation in Huntington's Disease

Huntington disease (HD) is a progressive neurodegenerative disorder characterized by severe movement, cognitive and behavioral changes caused by a CAG·CTG expansion in the HTT gene. Upon translation, this expansion results in mutant huntingtin protein (HTT) with an expanded polyGln repeat tract. HD is one of nine neurologic diseases caused by CAG expansion mutations that encode broadly expressed proteins containing expanded polyGln tracts. While there is substantial evidence that mutant HTT and other polyGln expansion proteins are toxic and contribute to disease, the differential vulnerability of specific brain regions is not yet understood. This example describes the detection of four RAN proteins (poly-Alanine, poly-Leucine, poly-Serine, and poly-Cysteine) in biological samples obtained from subjects having Huntington's disease.

RAN Proteins Accumulate in Cells Expressing Mutant HTT and in Human HD Brains

To test if RAN translation can occur across the HTT ORF in transfected cells, a series of minigenes containing HTT exon 1 with expansion mutations were generated (FIG. 1A). Immunoblots and immunofluorescence (IF) performed on transiently transfected HEK293T cells demonstrate that RAN translation occurs across a $CAG_{Ex}p$ located in an ATG-initiated ORF of an HTT-exon 1 minigene and produces polyAla and polySer RAN proteins. Additionally, constructs lacking the ATG demonstrate that an ATG initiation codon is not required for expression of the polyGln, polyAla or polySer expansion proteins (FIG. 1B, FIG. 7A-7C). Furthermore, polyAla and polySer are expressed at similar levels with and without an ATG initiation codon, indicating that frameshifting from an AUG initiated polyGln reading frame is not required for polyAla or polySer expression in these $CAG_{Ex}p$ HTT exon1 minigenes. In contrast, $(CAG)_{23}$ and non-hairpin forming $(CAA)_{80}$ constructs produce ATG-initiated polyGln but not RAN polyAla or polySer proteins. In summary, these data show that HTT exon-1 $(CAG)_{80}$ transcripts can express RAN proteins in all three reading frames in transfected cells.

Figure 7A:
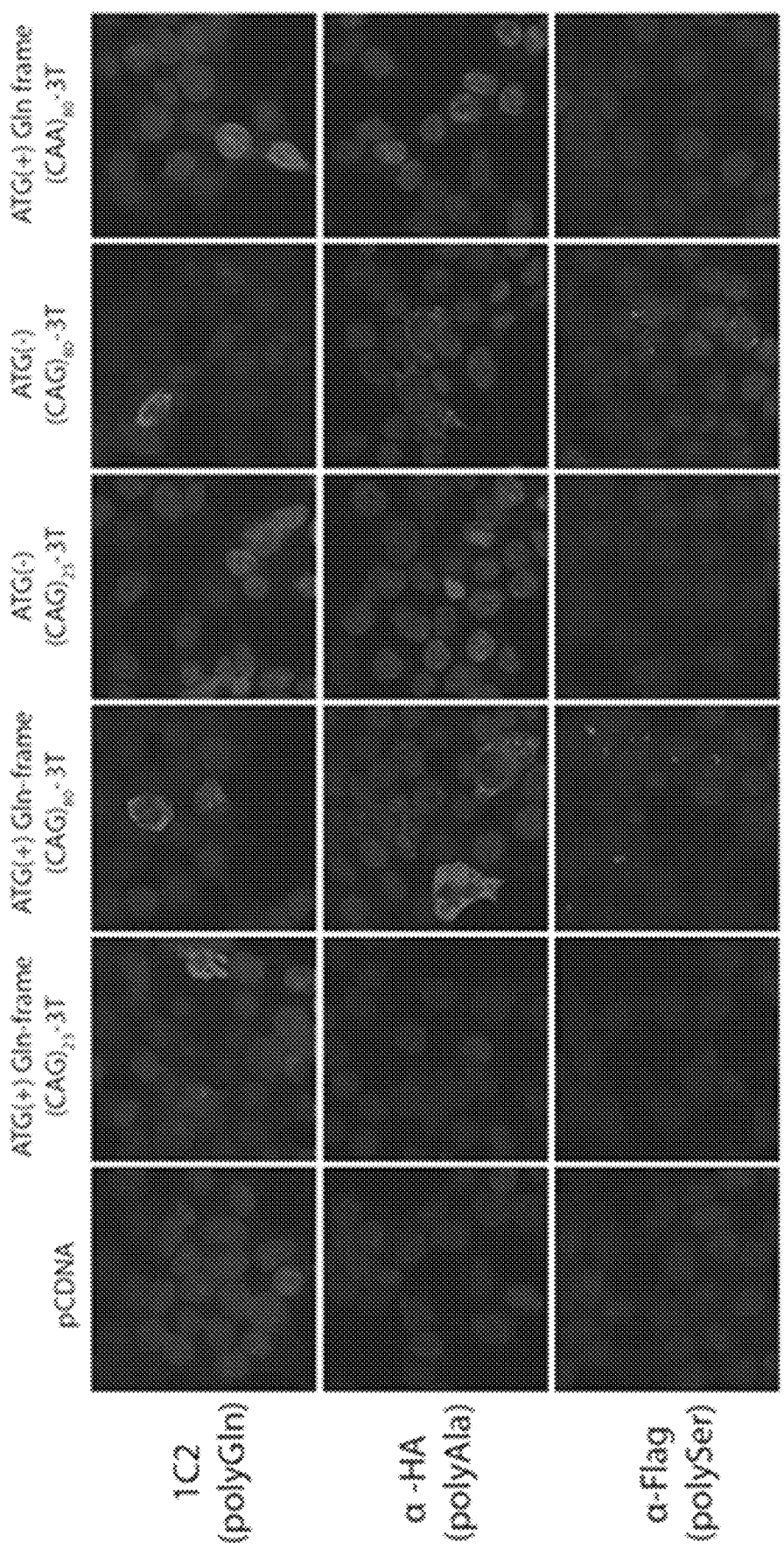
FIGS. 7A-7C show RAN translation in cells transfected with HTTexon1 minigenes.
Figure 7B:
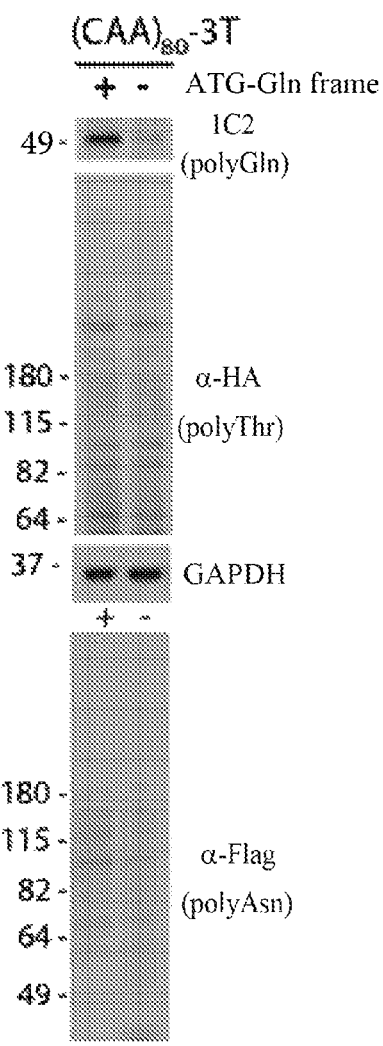
Figure 7C:
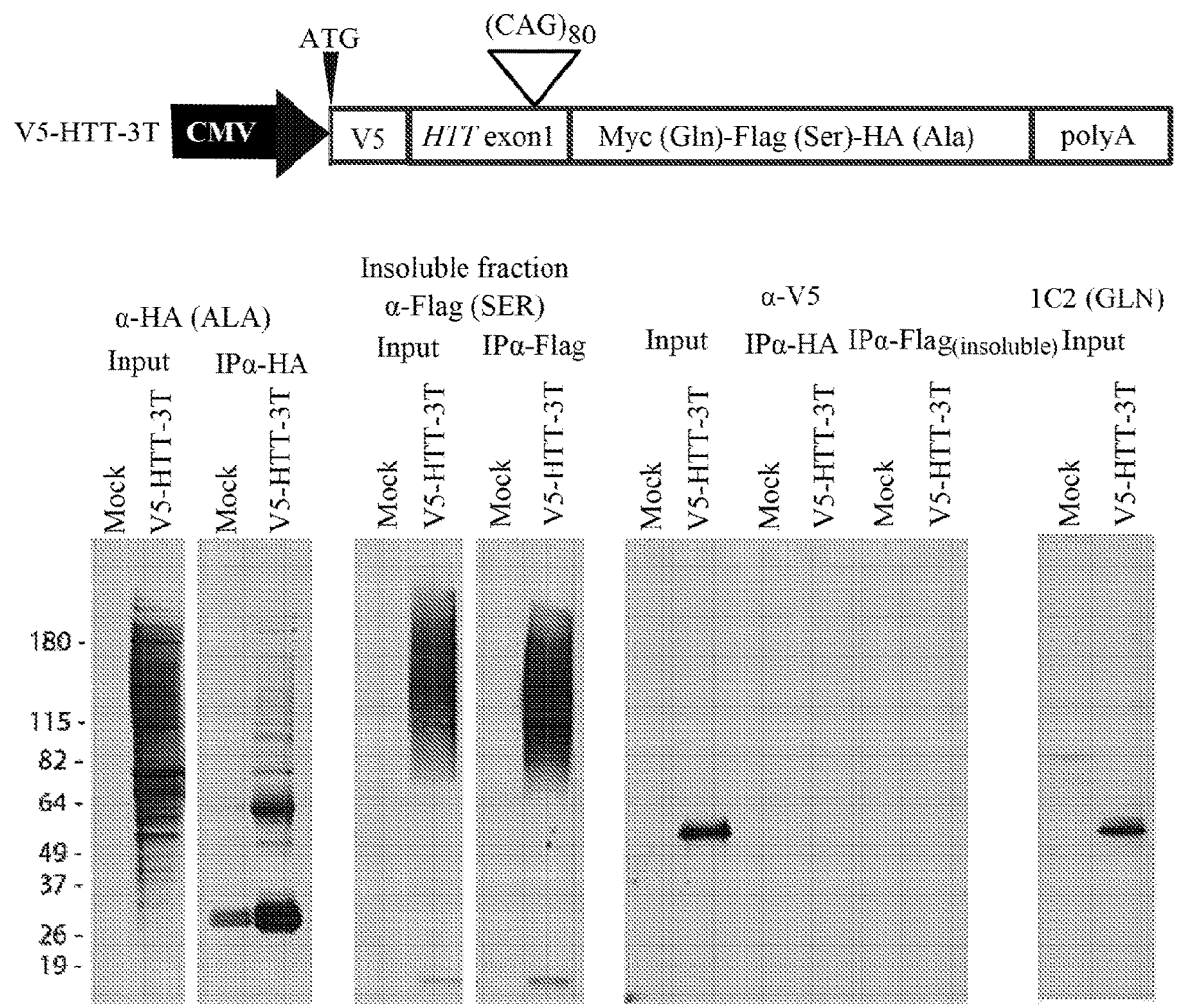
Figure 8A:
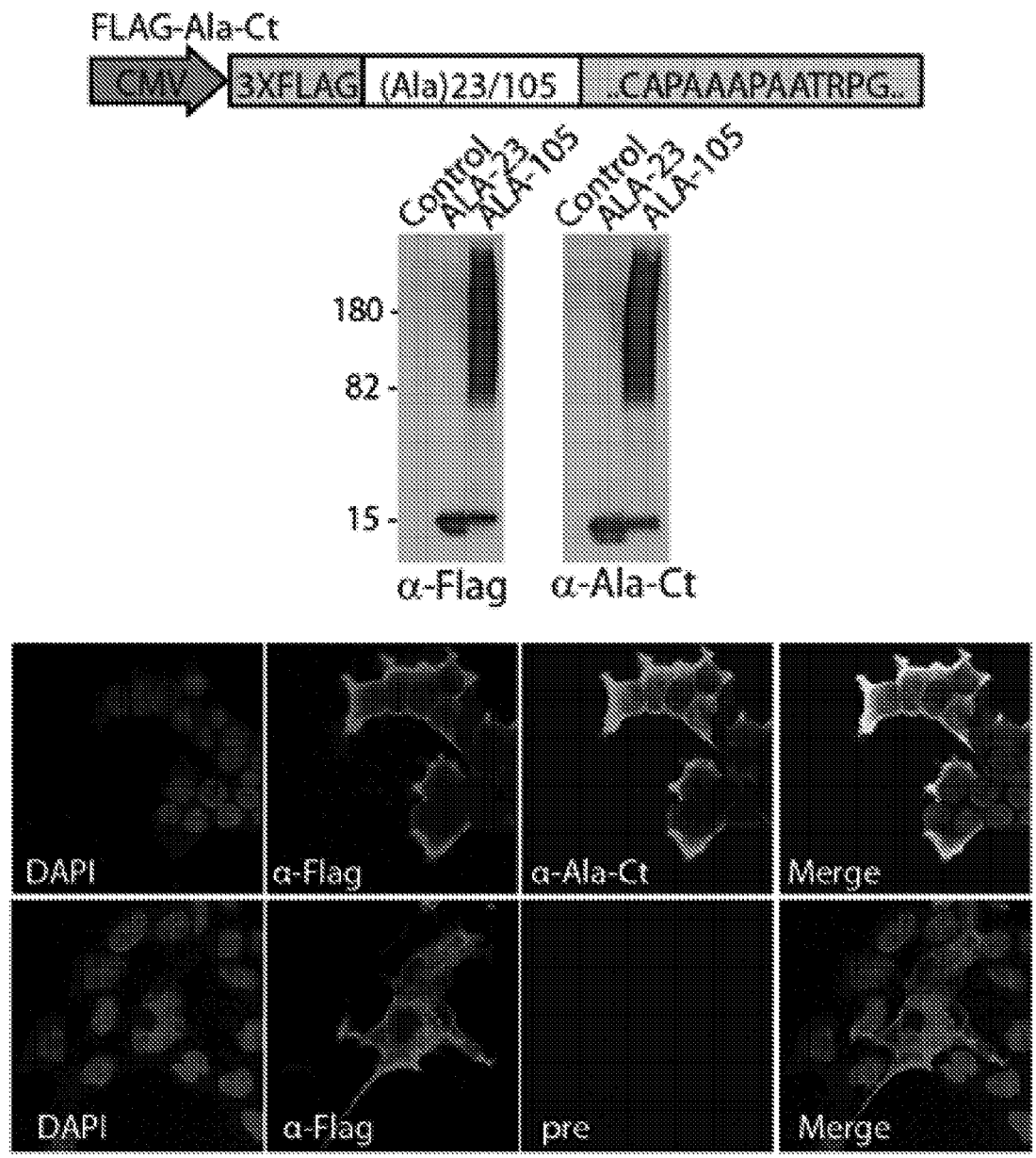

A second series of experiments were performed to test if frame-shifted products, which initiate at the AUG in the glutamine frame, can also produce hybrid polyGln/polyAla and polyGln/polySer proteins. Cells were transfected using a modified HD exon 1 minigene with a 5' V5 tag in the polyGln frame and three C-terminal epitope tags to label proteins translated in each of the three reading frames (FIGS. 8A-8C). Immunoprecipitations using antibodies against the C-terminal tags in the polyAla (α-HA) and polySer (α-Flag) frames followed by immunoblotting using the N-terminal and C-terminal tags shows that the polyAla and polySer proteins do not contain the N-terminal V5 tag in the ATG initiated polyGln frame (FIG. 7B).

Figure 1C:
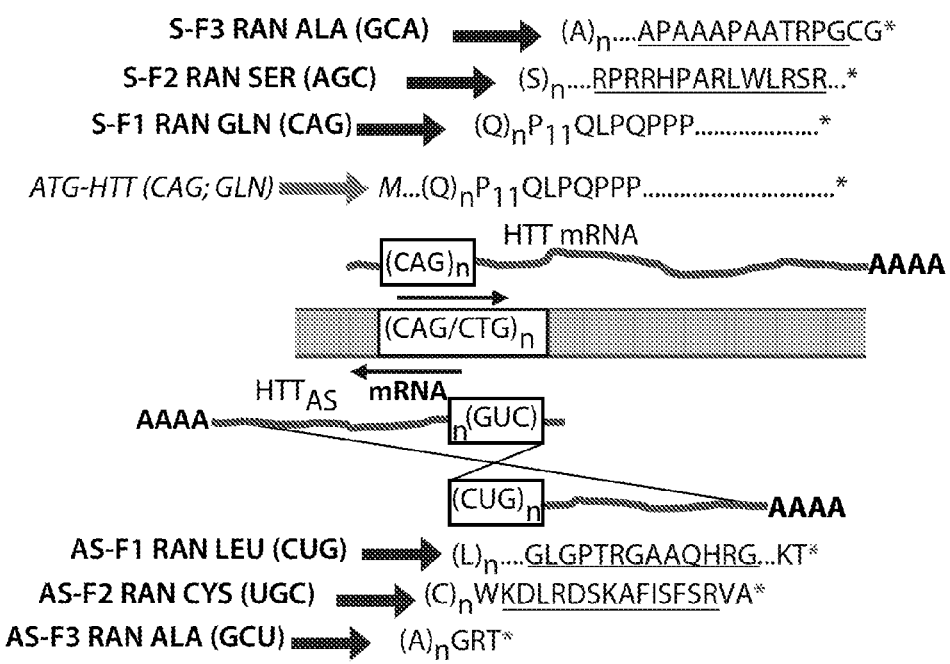
Figure 1D:
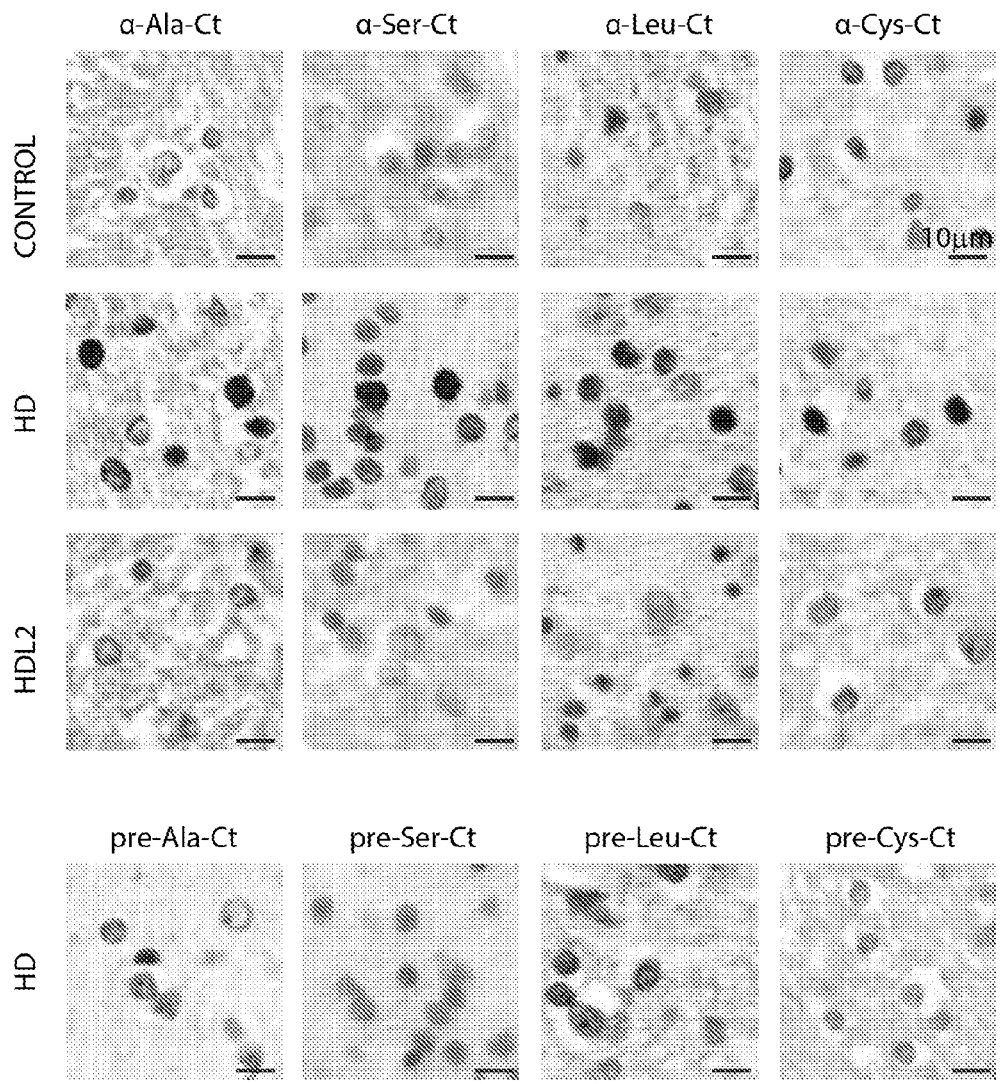
Figure 1E:
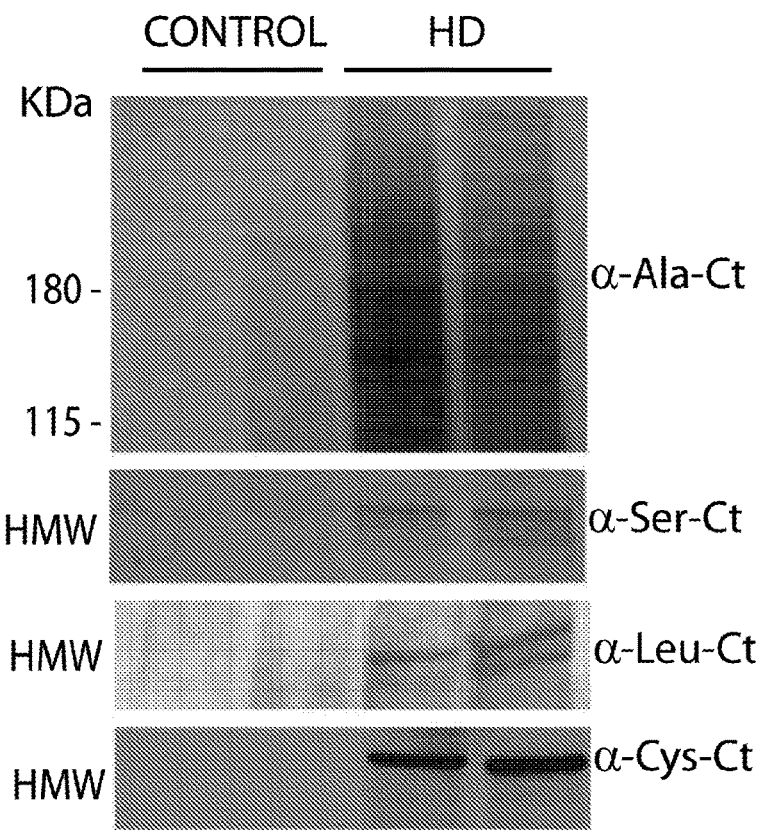

To test if RAN proteins are expressed in vivo, a panel of polyclonal antibodies against the predicted C-terminal regions available for four of the five possible novel RAN proteins were generated (FIG. 1C). The specificities of these antibodies, which recognize the putative polyAla (GCA), polySer (AGC), polyLeu (CUG) and polyCys (UGC) proteins were demonstrated in transfected cells (FIGS. 8A-8D). HD-RAN proteins could be detected by immunohistochemistry (IHC) in the striatum, a prominently affected brain region in HD. Positive staining was found using all four HD-RAN antibodies: α-Ala-Ct, α-Ser-Ct, α-Leu-Ct, α-Cys-Ct (FIG. 1D, Table 1) in HD but not HDL2 or control samples. No similar staining was seen with the corresponding pre-immune control sera for the various antibodies (FIG. 1D). Protein blot analyses of insoluble lysates from frontal cortex provide additional evidence that RAN proteins accumulate in HD but not control brains (FIG. 1E). These results show that in addition to the HTT polyGln expansion protein, the HD CAG·CTG expansion mutation also expresses four novel HD-RAN proteins and that these proteins are expressed from both sense and antisense transcripts.

RAN Proteins Accumulate in Specific Striatal Regions.

Figure 2A:
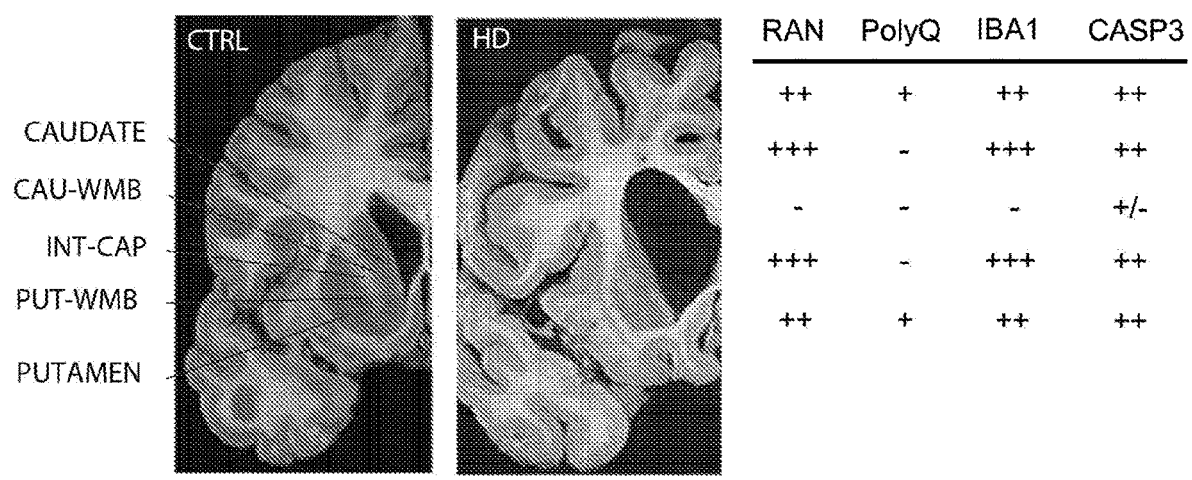
FIGS. 2A-2K show RAN proteins accumulate in specific striatal regions.
Figure 2B:
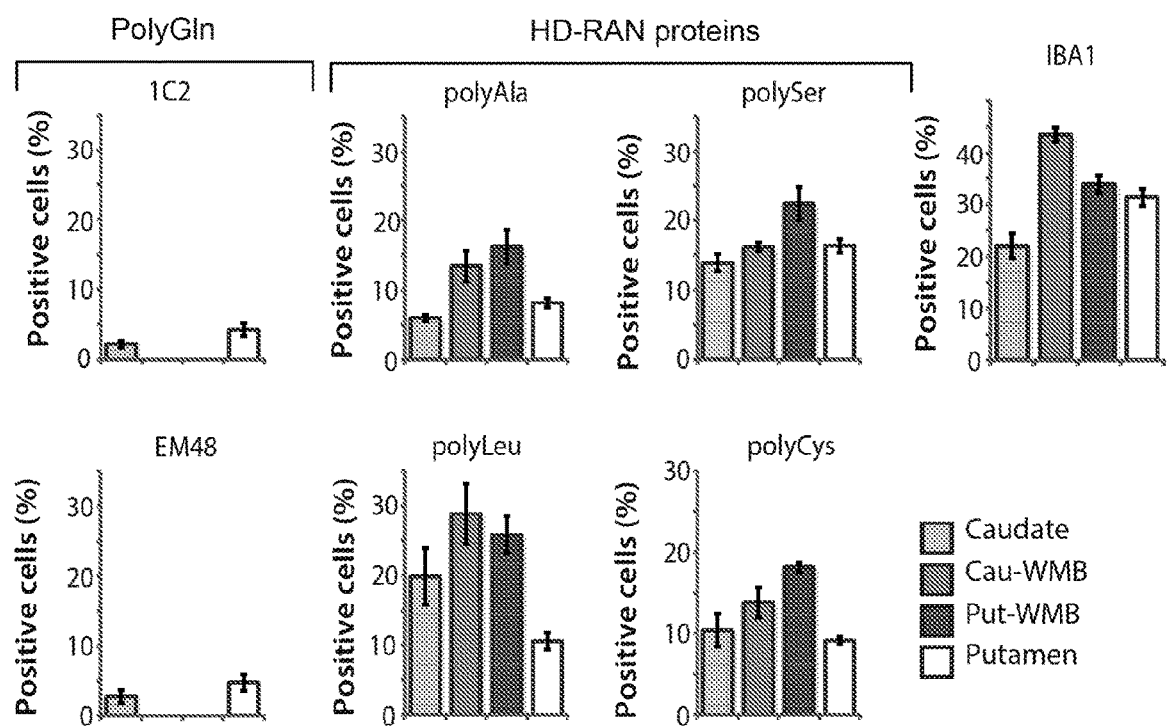
Figure 2C:
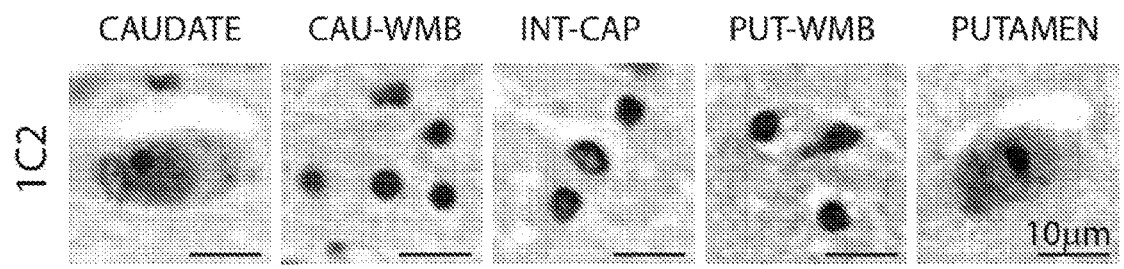
Figure 2D:
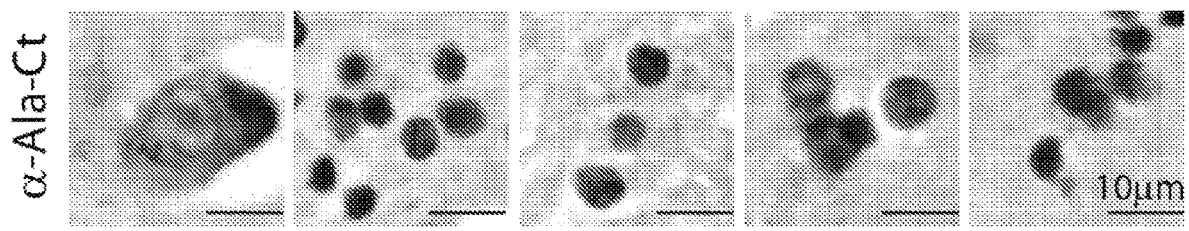
Figure 2E:
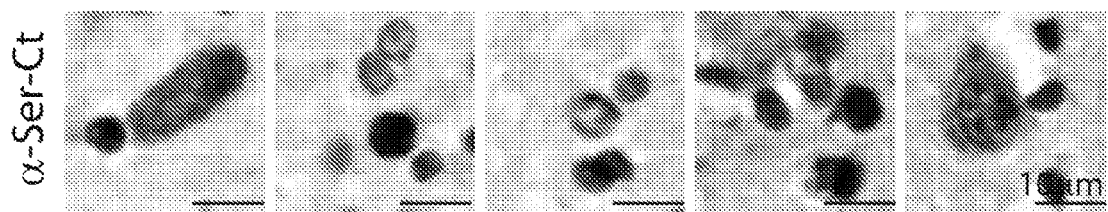
Figure 2F:
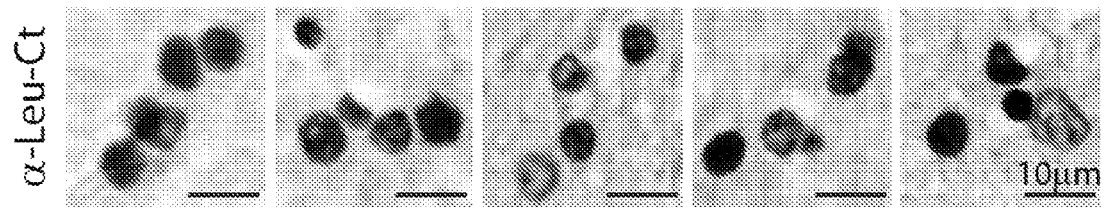
Figure 2G:
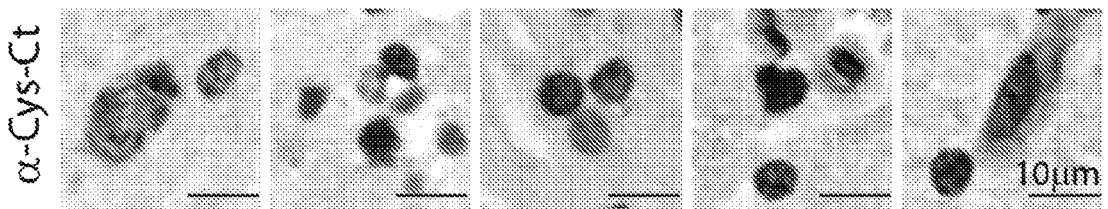
Figure 2H:
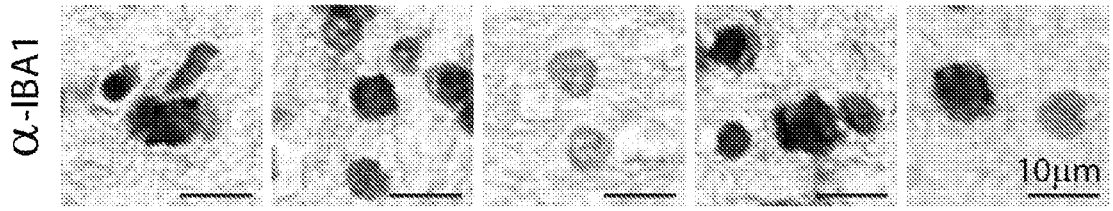
Figure 2I:
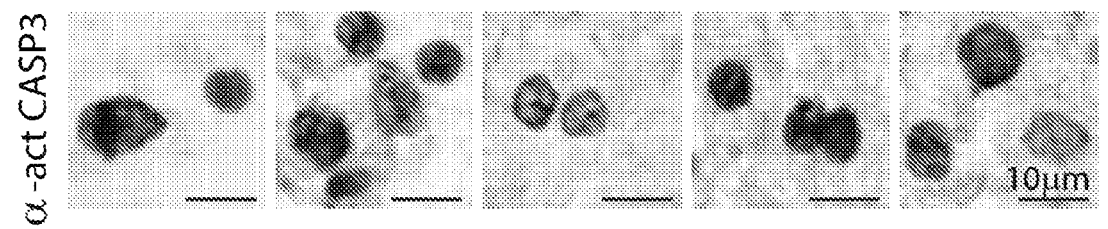
Figure 2J:
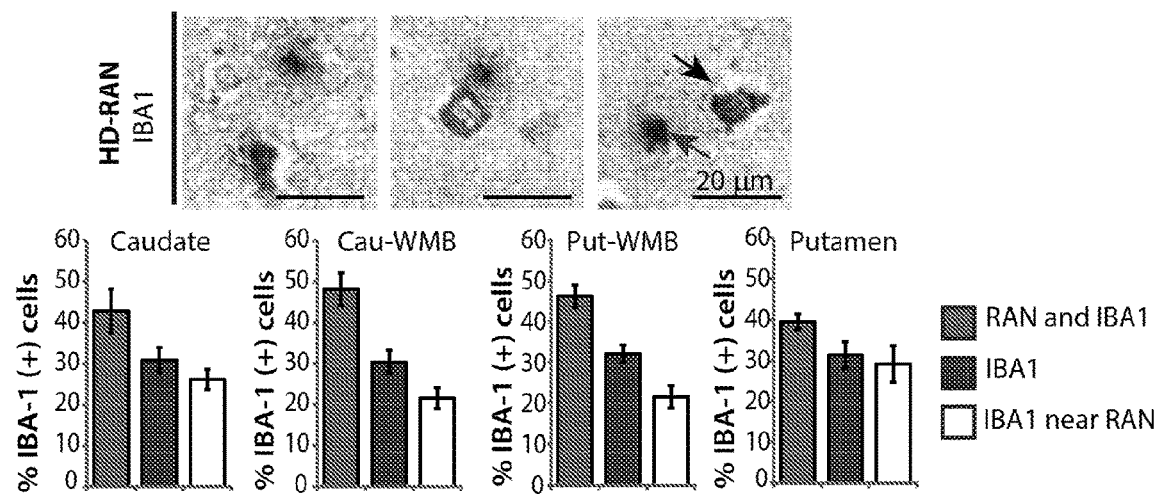
Figure 2K:
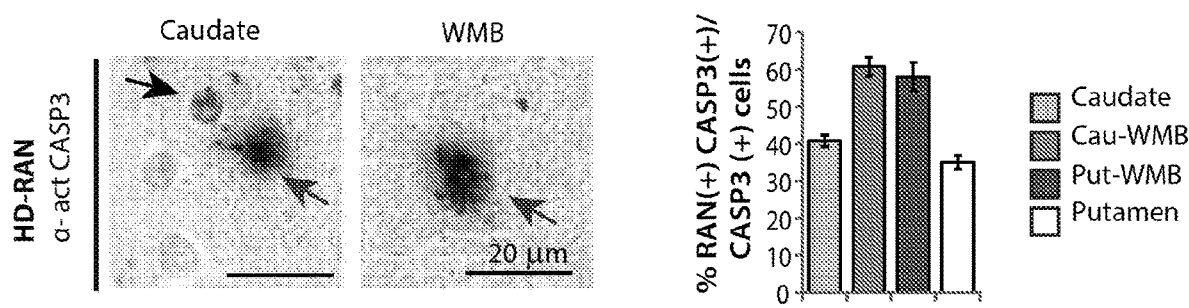
Figure 3A:
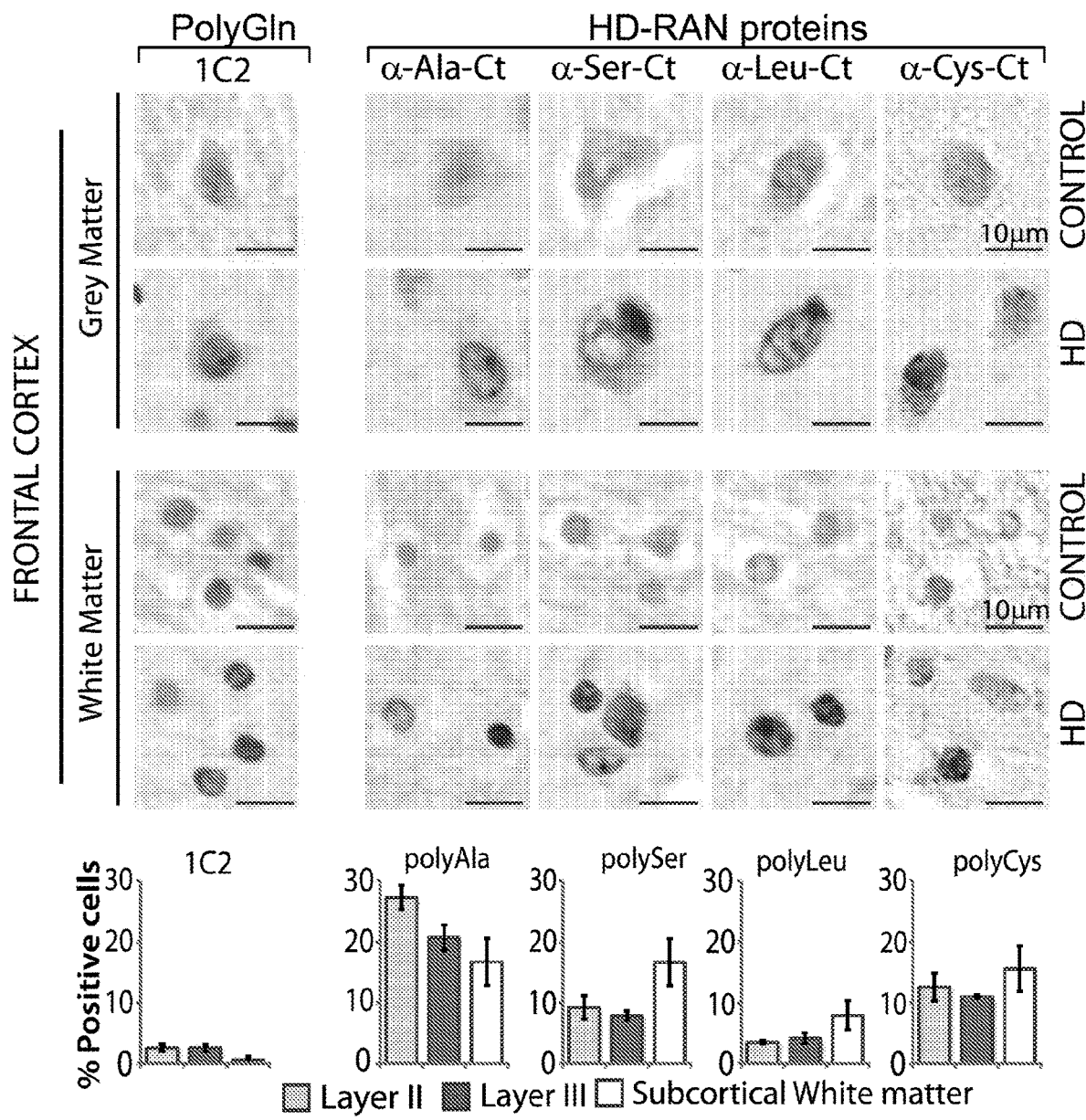
FIGS. 3A-3C show RAN proteins in HD frontal cortex and cerebellum.
Figure 3B:
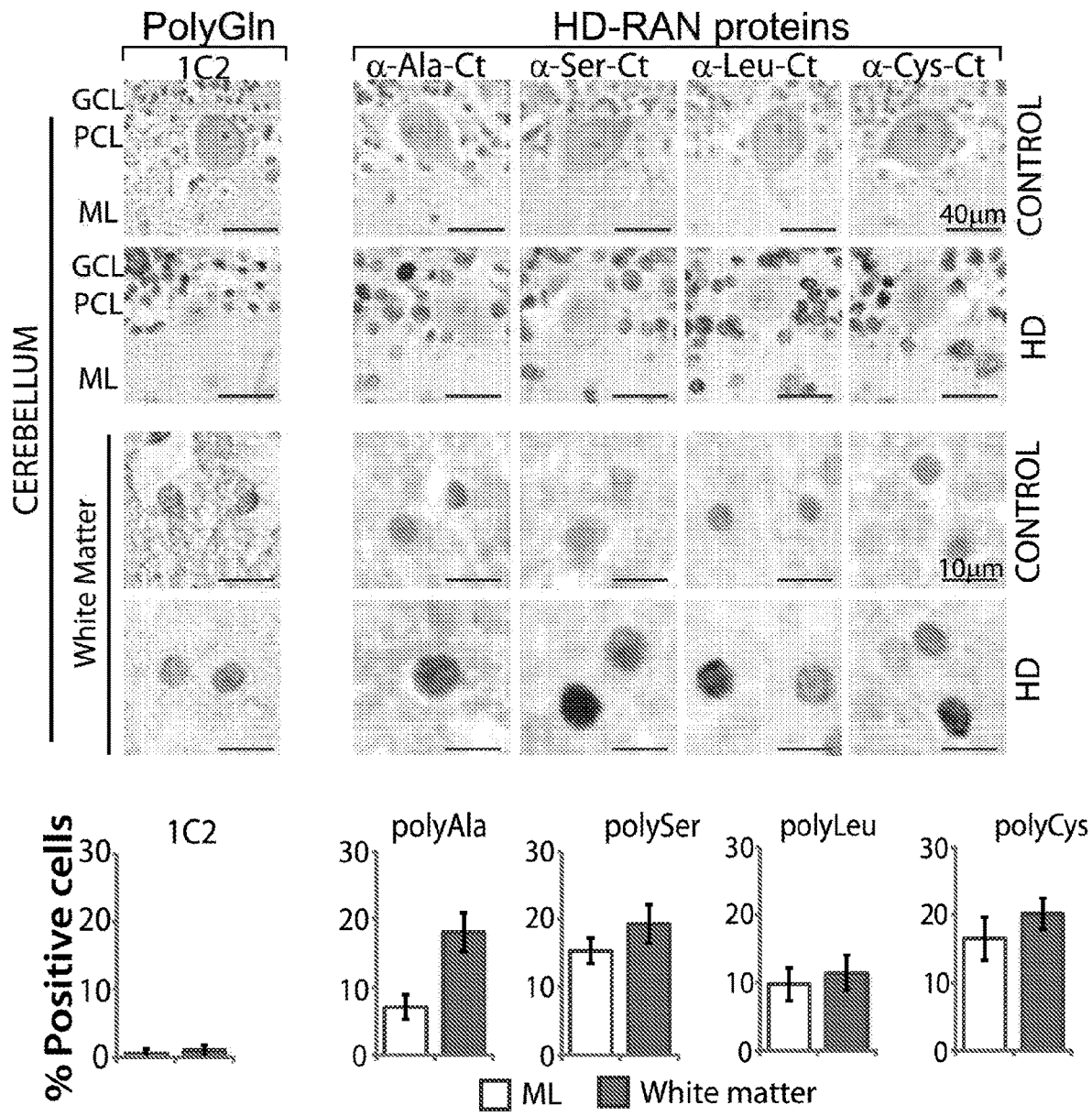
Figure 3C:
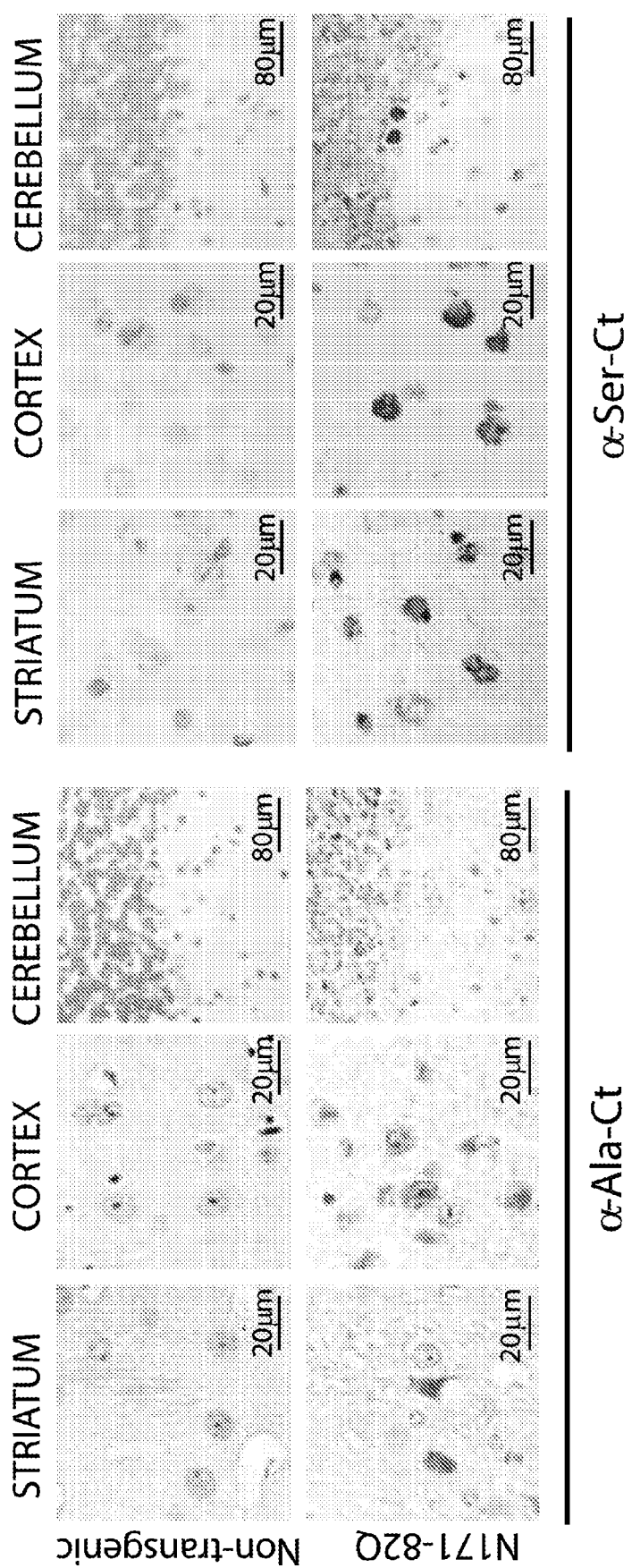

To explore areas of the striatum that are predominantly affected in HD (FIG. 2A), a series of IHC experiments using the HD-RAN protein antibodies were performed. These experiments show strong HD-RAN protein staining in the caudate and putamen of the striatum, two regions severely affected in HD (FIGS. 2B, 2D-2G, 9A-9E, 10A-10E, 11A-11E, and 12A-12E). Both nuclear and cytoplasmic staining was found in neurons and can appear as diffuse staining or as punctate aggregates. Additional staining in these regions is seen in astrocytes and microglia. HD-RAN staining is consistently strong in the white matter bundle regions of the caudate and putamen and most commonly localizes to the nucleus (FIGS. 2B, 2D-2G, 9A-9E, 10A-10E, 11A-11E, and 12A-12E). In contrast, HD-RAN staining is only rarely observed in the internal capsule, a white matter structure containing both ascending and descending axons that separate the caudate nucleus from the putamen, which is relatively preserved in HD. While the pattern of sense and antisense RAN protein staining across the caudate-putamen regions is strikingly similar, the pattern of staining using the 1C2 or EM48 antibodies to detect the expanded HTT polyGln protein was distinct. First, although 1C2/EM48 staining of neurons in the caudate and putamen is present and detects previously reported nuclear aggregates, positive cells are much less frequent (FIGS. 2B, 2C, 13A-13E). A second notable difference, is that polyGln aggregates detected by 1C2 or EM48 are not detected in regions with the most intense RAN-protein staining, the white matter bundles of the caudate and putamen (FIGS. 2B, 2C, 13A-13E).

RAN Proteins Accumulate in Regions with Neuroinflammatory Changes and Apoptosis.

Neuroinflammatory changes including an increase in microglial cells have been reported in HD and correlate with neuronal loss. To test if neuroinflammatory changes are found in areas that are RAN-positive, serial sections of the human autopsy material were stained with the Ibal antibody which recognizes microglia. RAN positive regions of the caudate and putamen were also strongly positive for Ibal, and similar to the HD-RAN staining, the most intense staining was seen in the white matter bundles (FIGS. 2B, 2H, 14A-14E). Because caspase-3 is a prominent marker of cell death in HD, serial sections were to determine if RAN-positive areas were also undergoing caspase-3 mediated cell death. Caspase-3 positive regions also showed staining patterns that are strikingly similar to the HD-RAN proteins in both the caudate and putamen and also within the caudate and putamen white matter bundles, which are strongly positive for HD-RAN proteins, but negative for the polyGln HTT protein (FIGS. 2B, 2I, 15A-15E). These results indicate that HD-RAN proteins contribute to the selective vulnerability of the caudate and putamen, including microglial activation and gliosis, which are some of the earliest changes in disease.

RAN Proteins in HD Frontal Cortex and Cerebellum

Since neurodegenerative changes in HD also occur in additional regions of the brain including the frontal cortex and the cerebellum, these regions were tested for RAN protein staining. Neuropathology in the frontal cortex is well established in HD, with cortical degeneration, neuronal loss in all layers, and increased density of large glial cells. Additionally, variable involvement of the cerebellum has recently been reported in HD (Bates et al., 2014; Rub et al., 2013). Positive staining for the four HD-RAN proteins was found in clustered patches, with the most prominent staining found in cortical layers II and III in HD but not controls. Nuclear staining for HD-Ala, HD-Ser, HD-Leu and HD-Cys was also found in HD cortical white matter (FIGS. 3A, 16A-16D, 17A-17D, 18A-18D, 19A-19D, Table 1).

TABLE 1

Summary of RAN protein staining in HD cases and controls.

| Case | | Age | Sex/Race | Repeat | PMID | Vonsattel Grade | Striatum | Frontal Cortex | Cerebellum |
|---|---|---|---|---|---|---|---|---|---|
| CTRL | 1 | 40 | M/W | | 6 | | – | – | – |
| | 2 | 56 | F/W | | 13 | | – | – | – |
| | 3 | 45 | F/W | | 20 | | – | – | – |
| | 4 | 57 | M/W | | | | – | – | – |
| HD | 1 | 47 | M/W | N/A | 30 | 2 | ++ | ++ | ++ |
| | 2 | 57 | M/W | N/A | 26 | 2 | ++ | + | ++ |
| | 3 | 60 | F/W | N/A | 24 | 3 | +++ | + | + |
| | 4 | 57 | F/W | N/A | 9.5 | 3 | +++ | + | + |
| | 5 | 52 | M/B | 49 | 24 | 3/4 | +++ | ++ | + |
| | 6 | 41 | M/W | 52 | 8 | 4 | +++ | + | + |
| | 7 | 46 | F/W | N/A | 7 | 4 | +++ | + | + |
| JHD | 1 | 8 | F/W | >100* | – | | +++ | ++ | ++++ |
| | 2 | 8 | M/B | ~100* | – | 3 | ++++ | +++ | ++ |
| | 3 | 27 | M/W | 69 | 22 | 4 | +++ | ++ | ++ |
| | 4 | 23 | F/B | 76 | 14 | 4 | ++++ | ++ | + |
| | 5 | 23 | F/W | 64 | 13 | 4 | +++ | ++ | ++ |

TABLE 1-continued

Summary of RAN protein staining in HD cases and controls.

| Case | | Age | Sex/Race | Repeat | PMID | Vonsattel Grade | Striatum | Frontal Cortex | Cerebellum |
|------|---|-----|----------|--------|------|-----------------|----------|----------------|------------|
| HDL2 | 1 | 58 | M/B | 11.5 | | 4 | – | – | – |
| | 2 | 41 | F/B | 3 | | 3 | – | – | – |
| SCA8 | | 80 | F | | | | N/A | N/A | – |

In the cerebellum, HD patients but not controls show RAN-protein staining (FIG. 3B, 16A-16D, 17A-17D, 18A-18D, 19A-19D, Table 1). Staining is found in the molecular and granule cell layers and in areas of Bergmann-glial proliferation surrounding the Purkinje cells. Staining of neurons in both the cortex and cerebellum was nuclear, cytoplasmic or perinuclear and was diffuse or localized to dense aggregates. In contrast, staining in cerebral and cerebellar white matter showed intense nuclear localization. While RAN protein staining in the cortex and cerebellum is easily detected, staining in the striatum was consistently more intense. IHC using the 1C2 antibody to detect expanded polyGln protein also showed nuclear staining in the neuronal layers of the frontal cortex (FIGS. 3A, 20A-20D), but no staining was evident in the white matter regions of the frontal cortex or the cerebellum (FIGS. 3B, 20E-20H).

In summary, RAN proteins accumulate in two additional affected brain regions, the frontal cortex and cerebellum. Additionally, prominent RAN-positive staining was observed in the absence of detectable polyGln staining in white matter regions. This latter observation indicates that RAN proteins play a role in white matter abnormalities previously described in HD, such as gliosis and white matter changes detected by DTI/MRI imaging.

RAN-Protein Accumulation and Aggregation is Length Dependent.

Figure 4A:
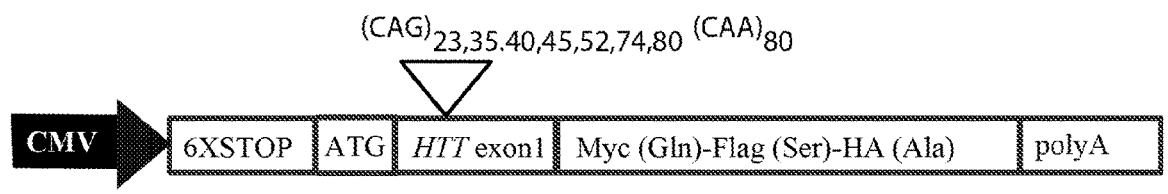
FIGS. 4A-4F show RAN protein accumulation and aggregation is length dependent.
Figure 4B:
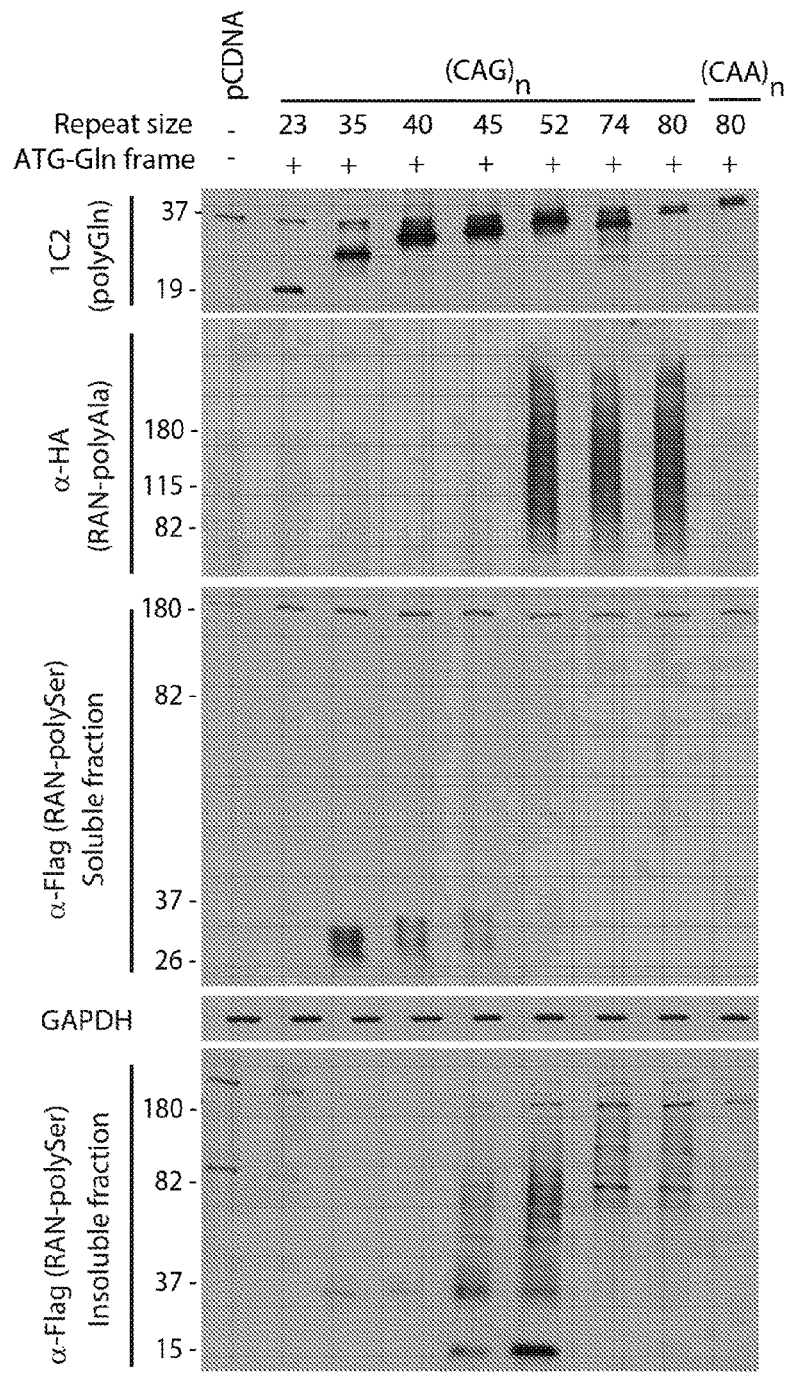
Figure 4C:
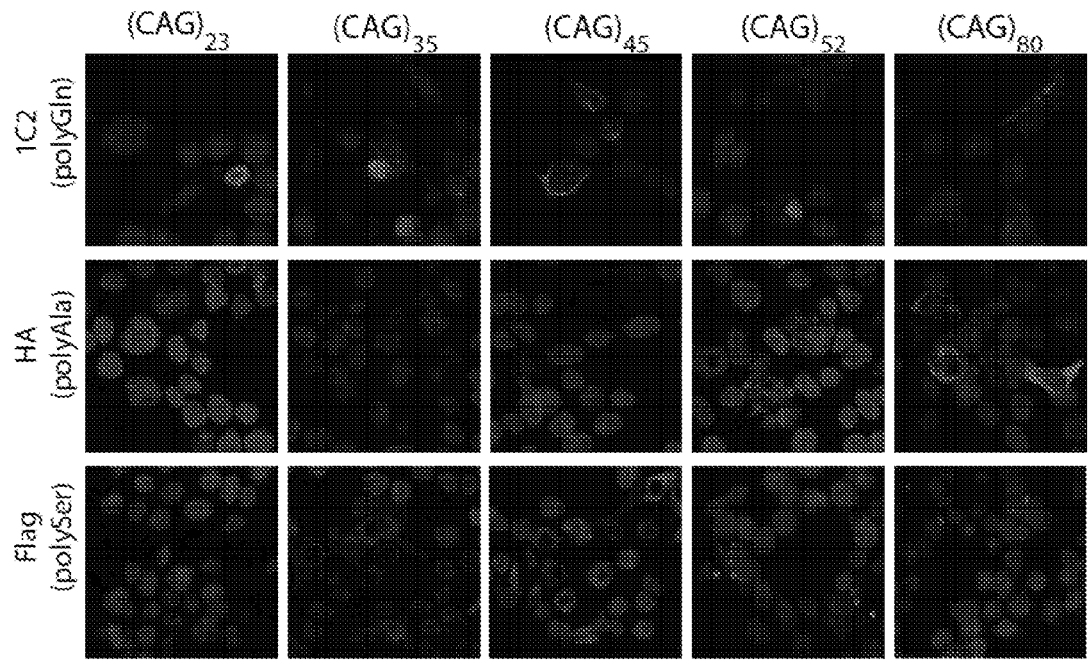
Figure 4D:
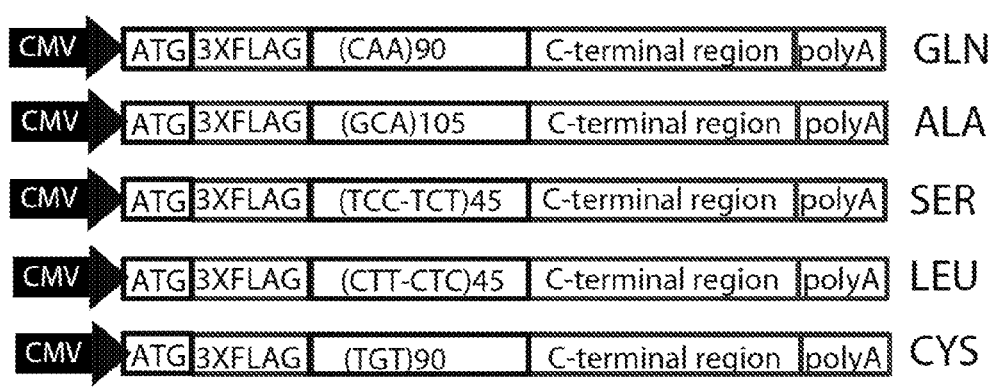
Figure 4E:
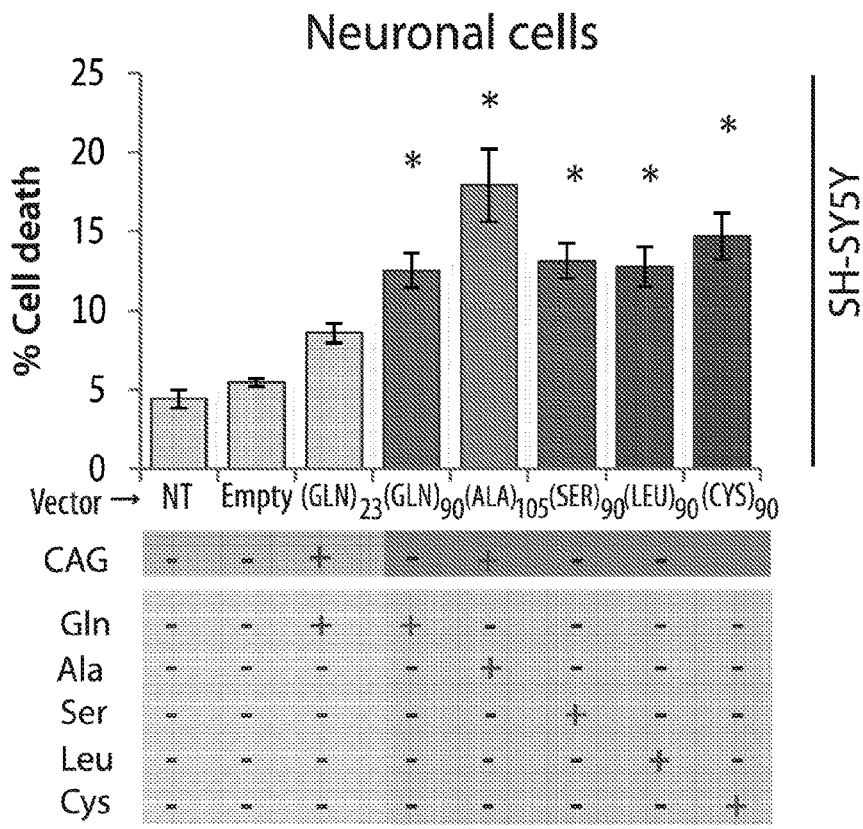
Figure 4F:
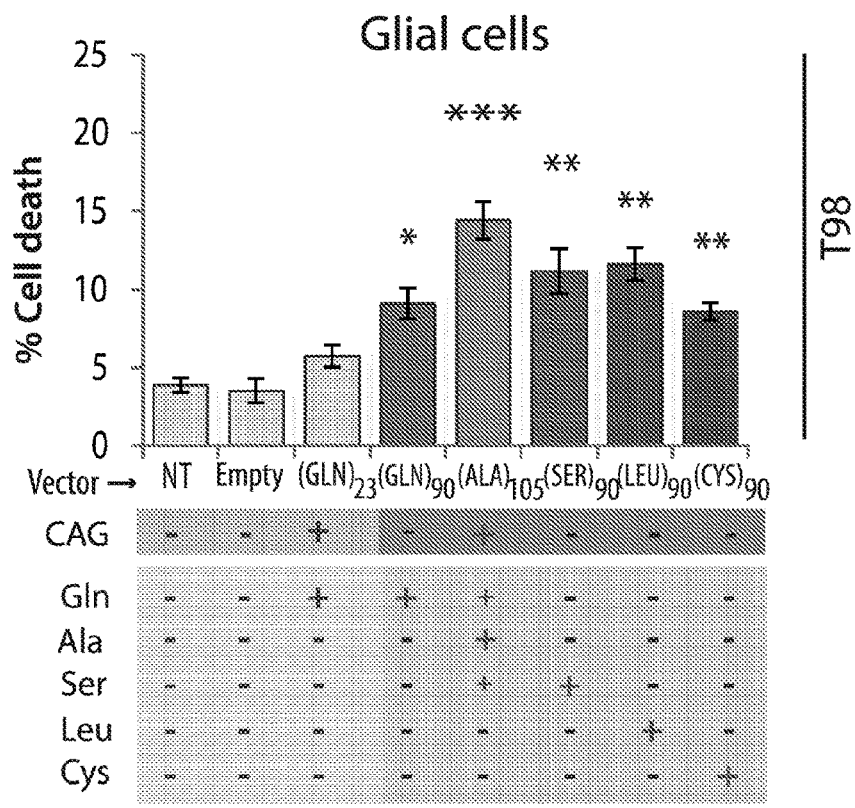
Figure 21A:
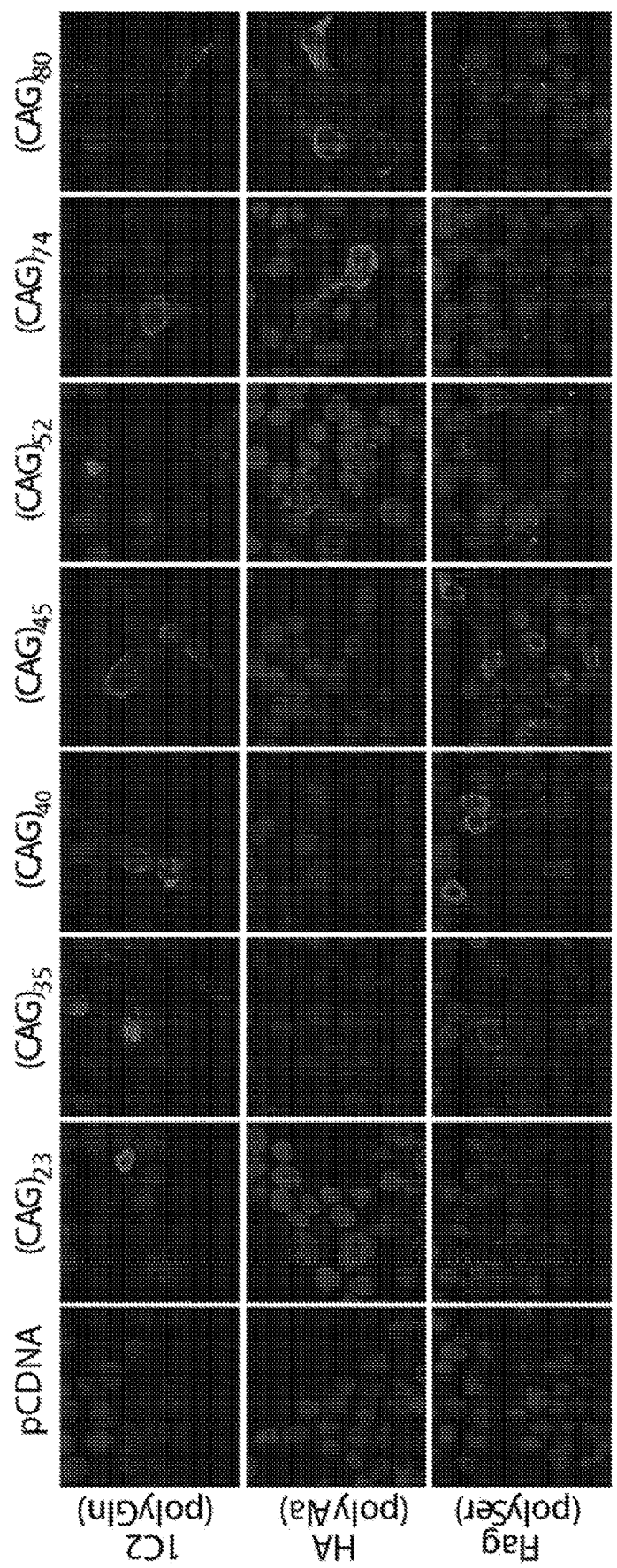
FIGS. 21A-21F show Length-dependent RAN protein accumulation and toxicity.

Longer CAG expansions are associated with earlier onset and increased severity in HD and other polyGln expansion disorders. To investigate the effects of repeat length on HD-RAN proteins a series of HTT-exon-1 minigenes with repeats ranging in length from 23 to 80 CAGs were developed (FIG. 4A). Transient transfections were performed and cell lysates examined for the accumulation of ATG-initiated polyGln and HD-RAN polyAla and polySer proteins. As expected, ATG-initiated polyGln proteins are expressed and accumulate at all repeat lengths (23-80 repeats) (FIGS. 4B, 4C, 21A). In contrast, RAN-protein accumulation and aggregation is length dependent. For example, protein blotting and IF show HD-polyAla RAN proteins accumulate in cells expressing CAG repeats >52 but not at repeats <45. In the polySer frame, RAN protein accumulation is evident at >35 repeats, and as the repeats get longer, RAN-polySer shifts from being in the soluble (35-40 repeats) to the insoluble fraction (45-80 repeats) by protein blot (FIG. 4B). Similarly, in transfected cells, polySer staining changes from a diffuse pattern (35-40 repeats) to a progressively more punctate, almost pin-like staining pattern forming granular cytoplasmic inclusions (45-80 repeats) (FIGS. 4C, 21A). In summary, the selective accumulation of RAN polyAla and punctate polySer proteins in this in vitro system occurs at repeat lengths typically associated with early-onset and juvenile cases of HD.

HD-RAN Proteins Affect Cell Survival In Vitro

The discovery of HD-RAN proteins in caspase-3 positive brain regions strongly suggests that RAN proteins are toxic. To examine the effect of each individual RAN protein independently of RNA-mediated effects, polyGln, polySer, polyLeu and polyCys minigenes were generated using alternative codons to prevent RNA hairpin formation and RAN translation. ATG-initiated polyAla was generated with a GCA expansion. All the minigenes contained the repeat expansion and the complete C-terminal region for each protein.

Figure 21B:
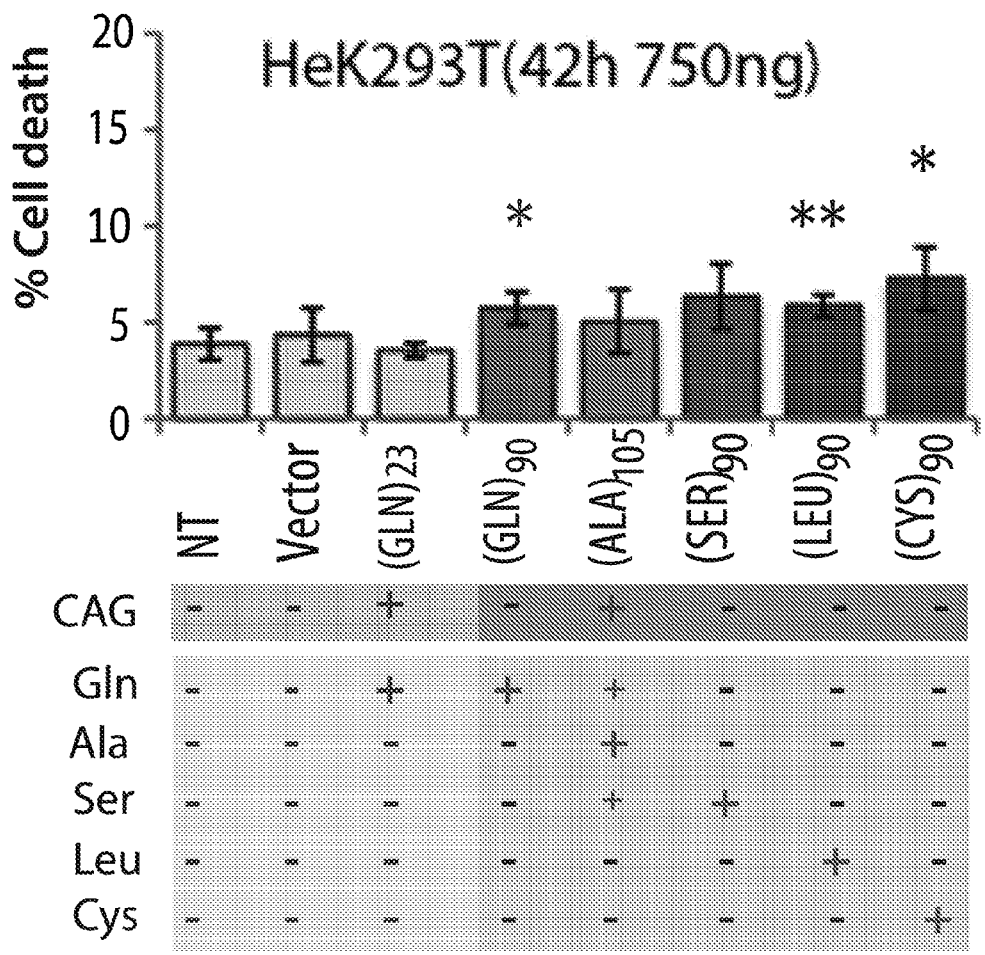
Figure 21C:
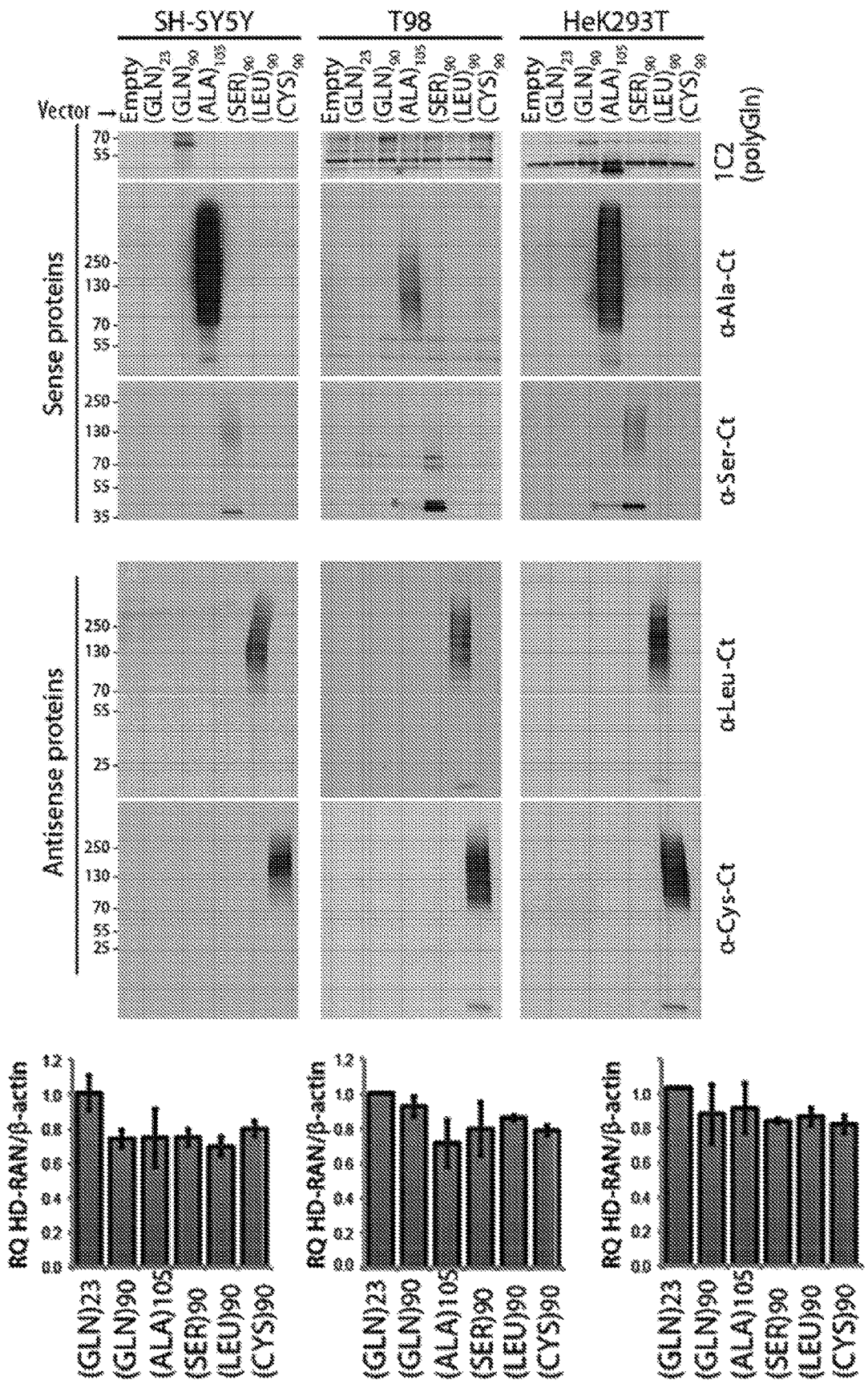
Figure 21D:
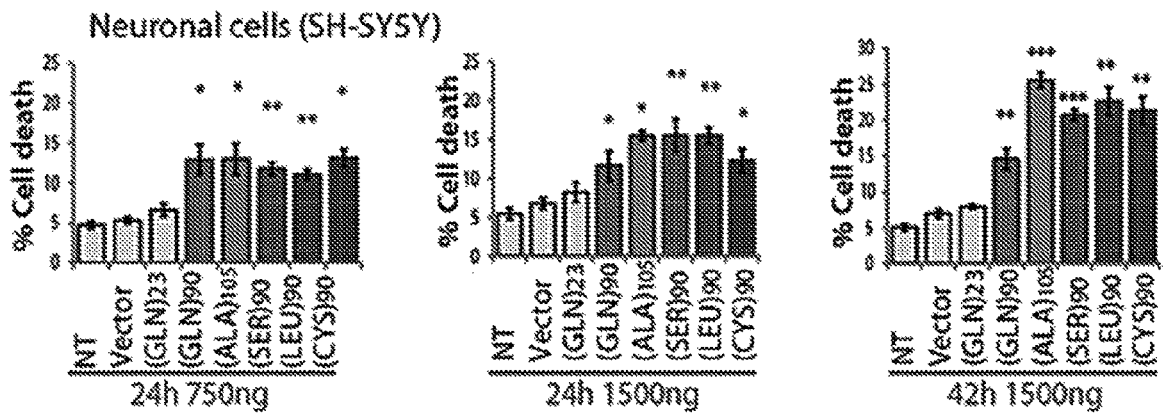
Figure 21E:
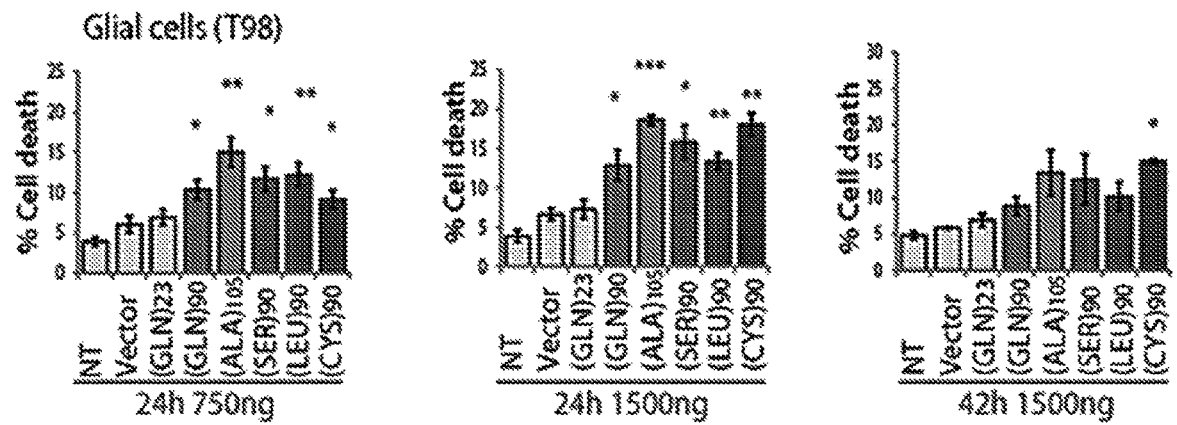
Figure 21F:
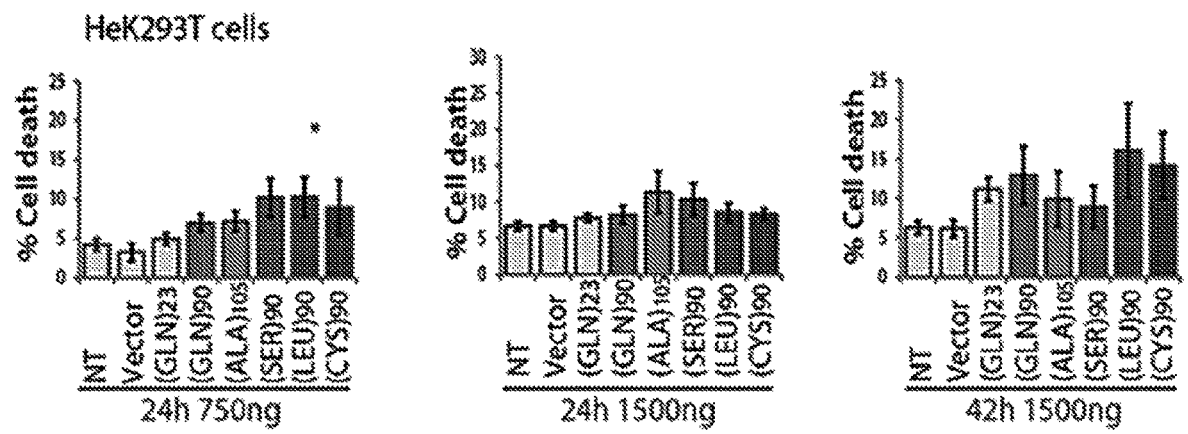

T98 neural cells and SH-SYSY neuronal cells transfected with these constructs showed a significant decrease in cell viability compared to cells expressing a short repeat. HD-RAN proteins are equally or more toxic than polyGln alone. The transfection with the polyAla construct, which expresses high polyAla levels, but also low levels of polyGln and polySer, dramatically decreased cell survival (FIGS. 4D, 4E, 21C-21E). In contrast, toxic effects of these proteins were not found in transfected HEK293T cells at 42 hours post-transfection (FIGS. 21B, 21F) demonstrating that the vulnerability to HD-RAN proteins is cell-type specific. Taken together, these data demonstrate that: 1) The expression of individual HD-RAN proteins using non-hairpin forming alternative codons decreases cell survival; 2) HD-RAN proteins are differentially toxic to individual cell types.

HD-RAN Proteins Accumulate in Severely Affected Juvenile Cerebellar Regions.

Figure 5A:
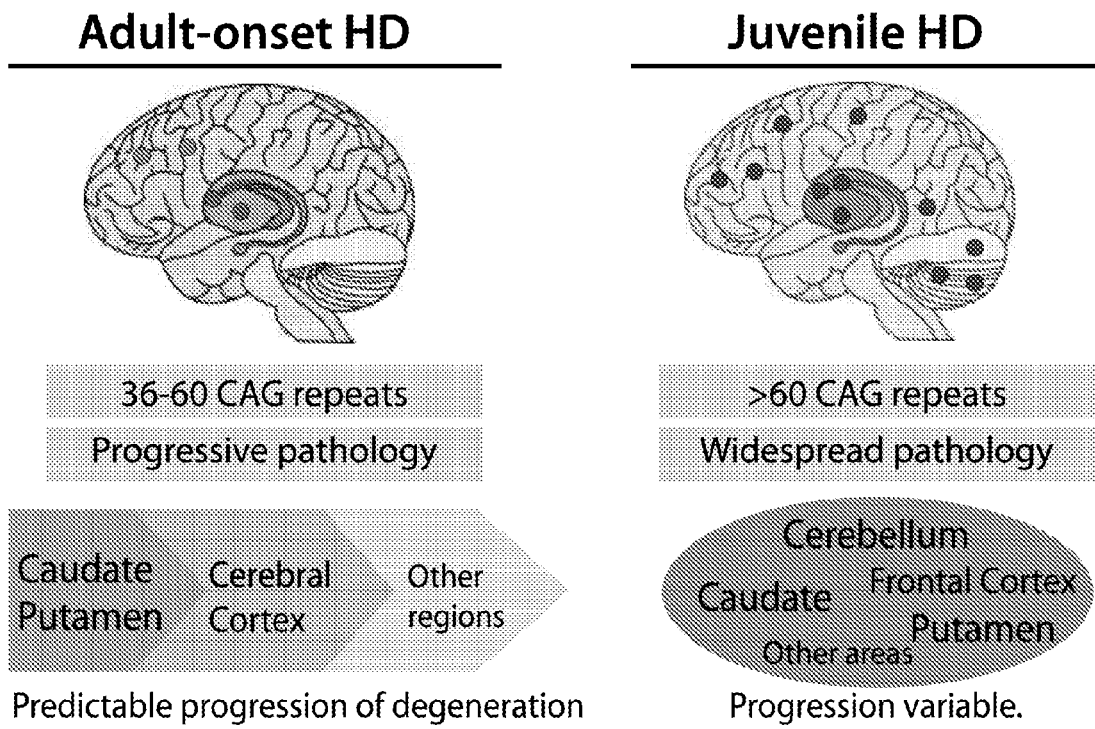
FIGS. 5A-5D show HD-RAN proteins accumulate in severely affected juvenile cerebellar regions.
Figure 5B:
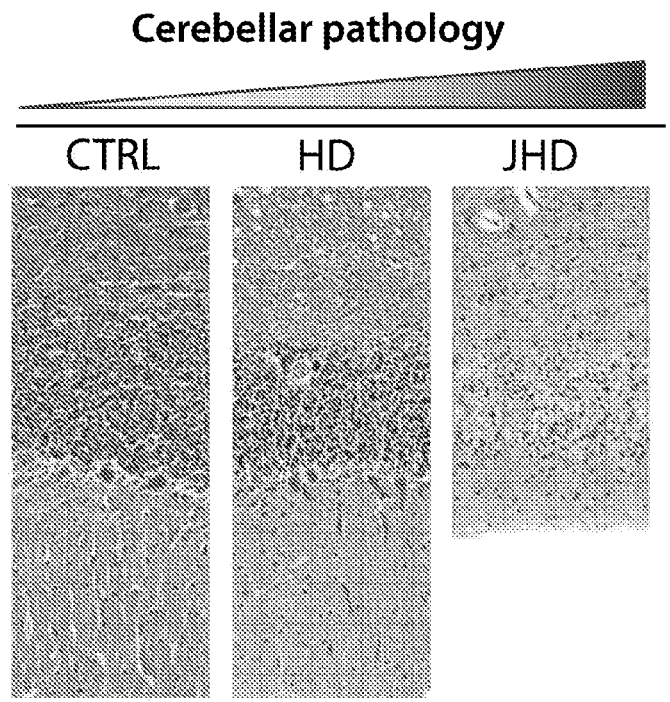

In adult-onset HD there is a predictable disease progression that first, and most severely, affects the caudate/putamen followed by the frontal cortex and other brain regions. In contrast, disease progression in juvenile-onset cases shows a more widespread pathology, with some patients showing severe involvement of the caudate and putamen while others show relative sparing of this region but severe atrophy of the cortex or cerebellum (FIG. 5A). Given that RAN protein expression increases with repeat length, whether RAN protein staining is more prominent in juvenile HD cases, and severely affected regions show increased RAN protein accumulation was investigated. Autopsy tissue from five juvenile-onset cases was analyzed. All five cases showed increased frequency and more intense staining for all four RAN proteins in striatum, frontal cortex and cerebellum (Table 1). Two of these cases, which came to autopsy at 8 years of age with repeats greater than 100, showed marked cerebellar atrophy with abundant RAN protein staining in all layers of the cerebellum (FIGS. 5B, 5C, 22A-22T, Tables 1 and 2).

TABLE 2

HD-RAN protein staining and cerebellar atrophy in juvenile 1-1D.

| CASES JHD | Age | Repeat | PMD | COL atrophy | RAN |
|-----------|-----|--------|-----|-------------|------|
| 1 | 8 | >100* | | ++++ | ++++ |
| | 8 | –100* | | ++ | ++ d |
| 2 | 27 | 69 | 22 | + | ++ I |
| 3 | 23 | 76 | 14 | + | + |
| | 23 | 64 | 13 | + | ++ |

Figures 22A, 22B, 22C, 22D:
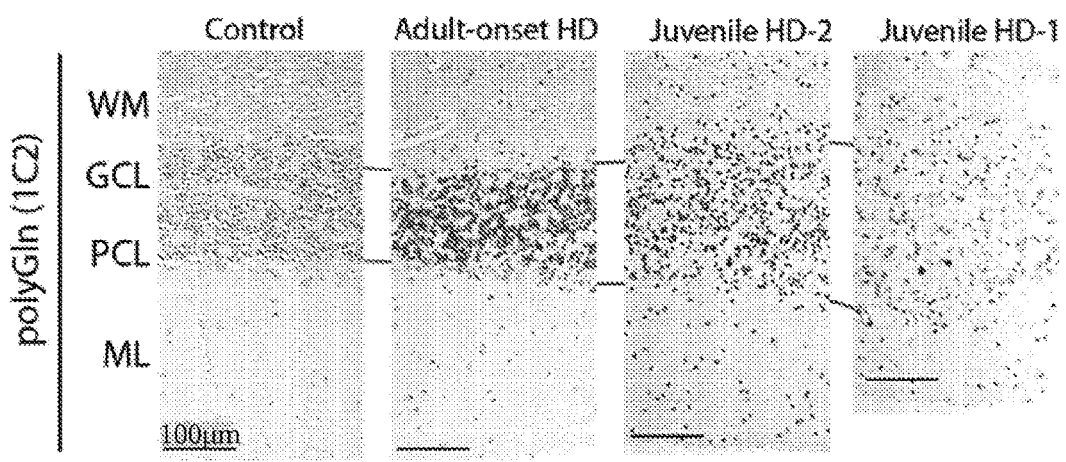
FIGS. 22A-22T show IHC staining showing α-polyGln (FIGS. 22A-22H), α-polySer (FIGS. 22I-22L), α-polyCys (FIGS. 22M-22P) and α-IBA1 (FIGS. 22Q-22T) staining in control, adult-onset and juvenile-onset HD with severe cerebellar atrophy in cerebellar cortex (GCL, PCL, ML) and subcortical white matter (WM).
Figures 22E, 22F, 22G, 22H:
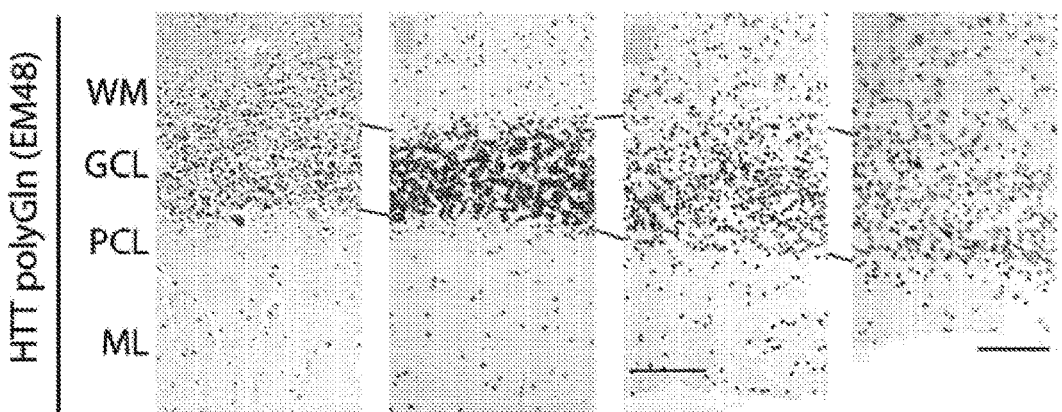
Figures 22I, 22J, 22K, 22L:
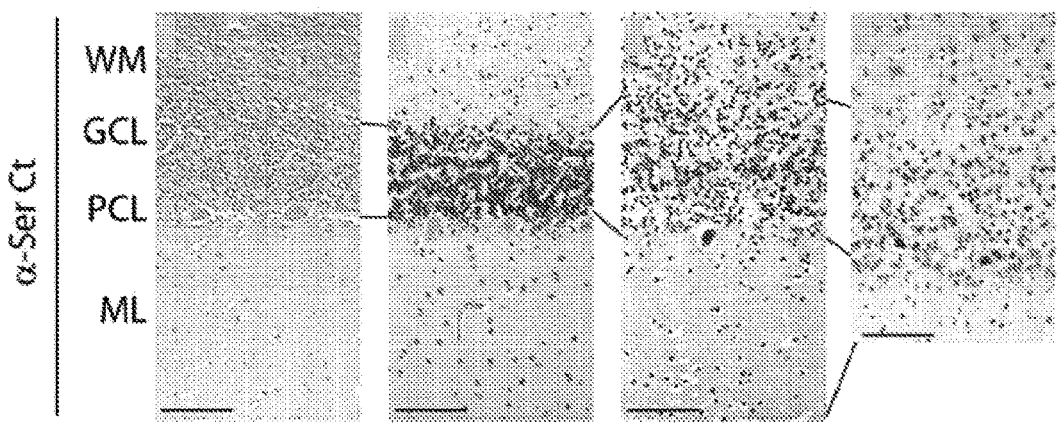
Figures 22M, 22N, 22O, 22P:
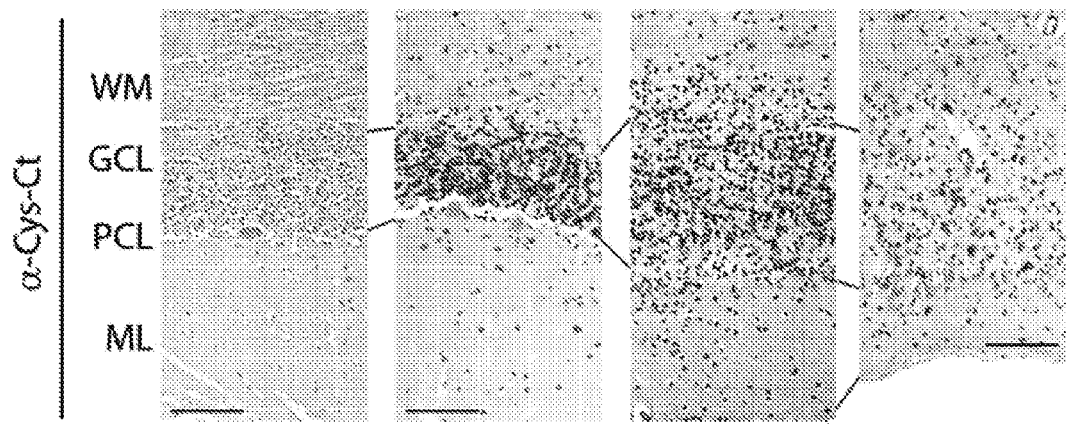
Figures 22Q, 22R, 22S, 22T:
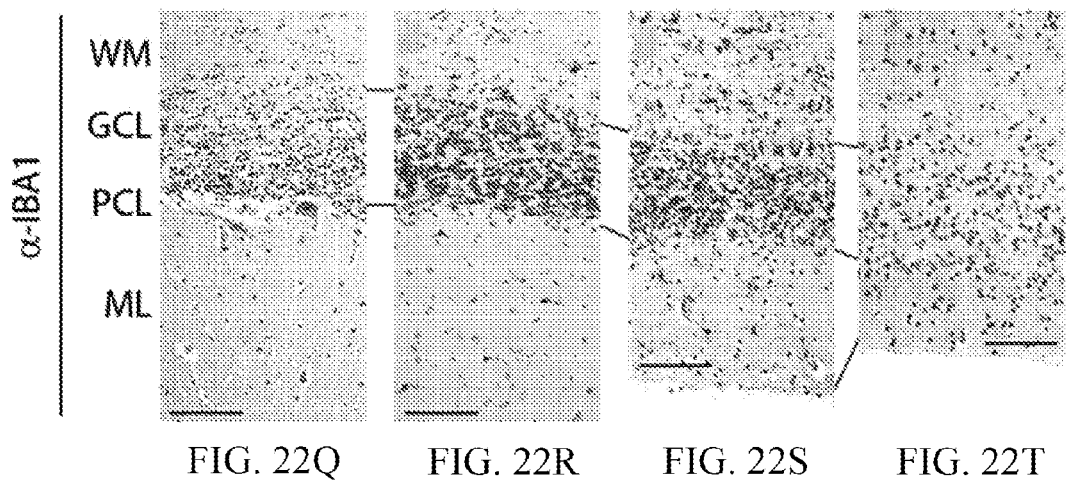
Figures 23A, 23B, 23C:
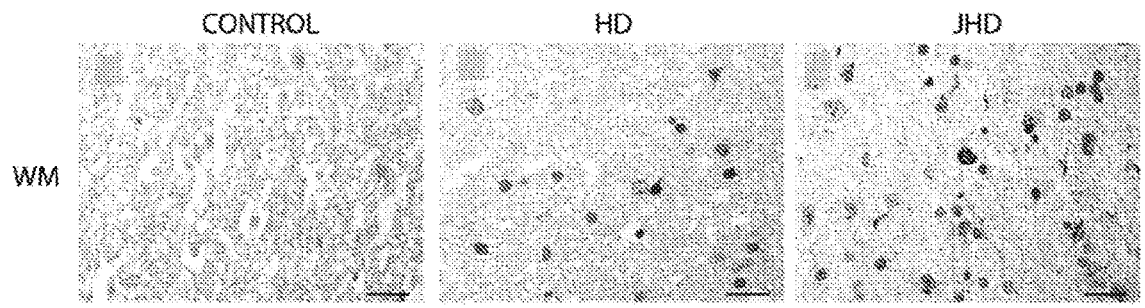
FIGS. 23A-23L show IHC staining in adult- and juvenile-onset HD cerebellar subcortical white matter (FIGS. 23A-23C, 23G-23I) or the dentate nucleus (FIGS. 23D-23F, FIGS. 23J-23L) with α-polySer-Ct or α-polyCys-Ct antibodies as indicated.
Figures 23D, 23E, 23F:
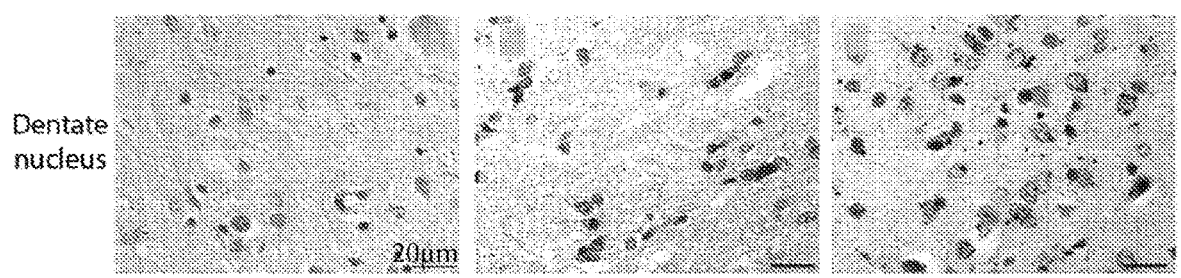
Figures 23G, 23H, 23I:
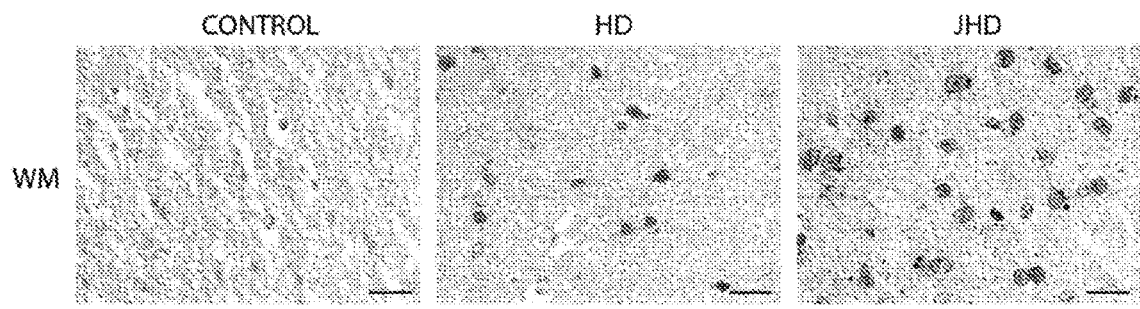
Figures 23J, 23K, 23L:
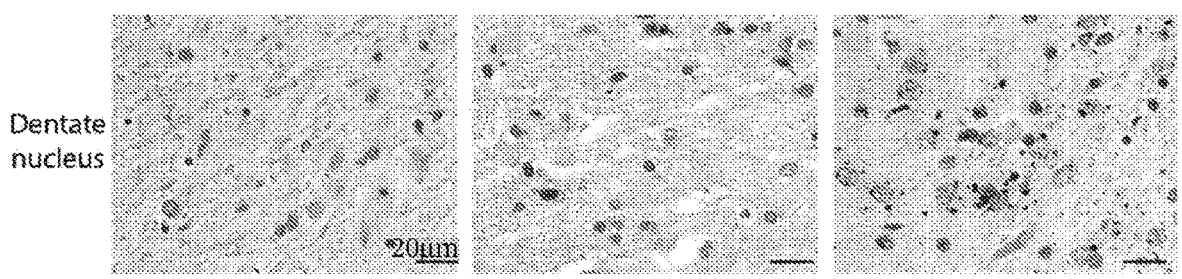

In the most severely affected juvenile HD case (JHD-1), the cerebellum showed more intense RAN polySer and polyCys staining compared to adult HD (Table 1, FIGS. 22A-22T) with JHD showing ubiquitous, densely reactive, often punctate nuclear or perinuclear staining in regions throughout the cerebellum. Positive regions included molecular layer interneurons; Bergmann glia and basket cells surrounding the Purkinje cells, the granular layer and subcortical and deep white matter regions including regions surrounding the dentate nuclei (FIGS. 5C, 22A-22T, 23A-23L). Additionally, RAN protein staining in the white matter surrounding the dentate nucleus was found in regions of gliosis, with prominent α-polyCys staining of astrocytes and microglia-like cells (FIGS. 22A-22T, 23A-23L). A second juvenile case (JHD-2), also with cerebellar atrophy, showed polySer and polyCys positive staining in similar regions as well as in the remaining Purkinje cells (FIGS. 22A-22T). In contrast, polyglutamine staining in the cerebellum was rare in all cases, with no positive staining detected in the adult-onset cases or JHD-2 using the 1C2 or EM48 antibodies (FIGS. 5C, 22A-22T) and few positive cells per 20× field in JHD-1 were detected with 1C2 but not EM48 (FIGS. 22A-22T).

Figure 5C:
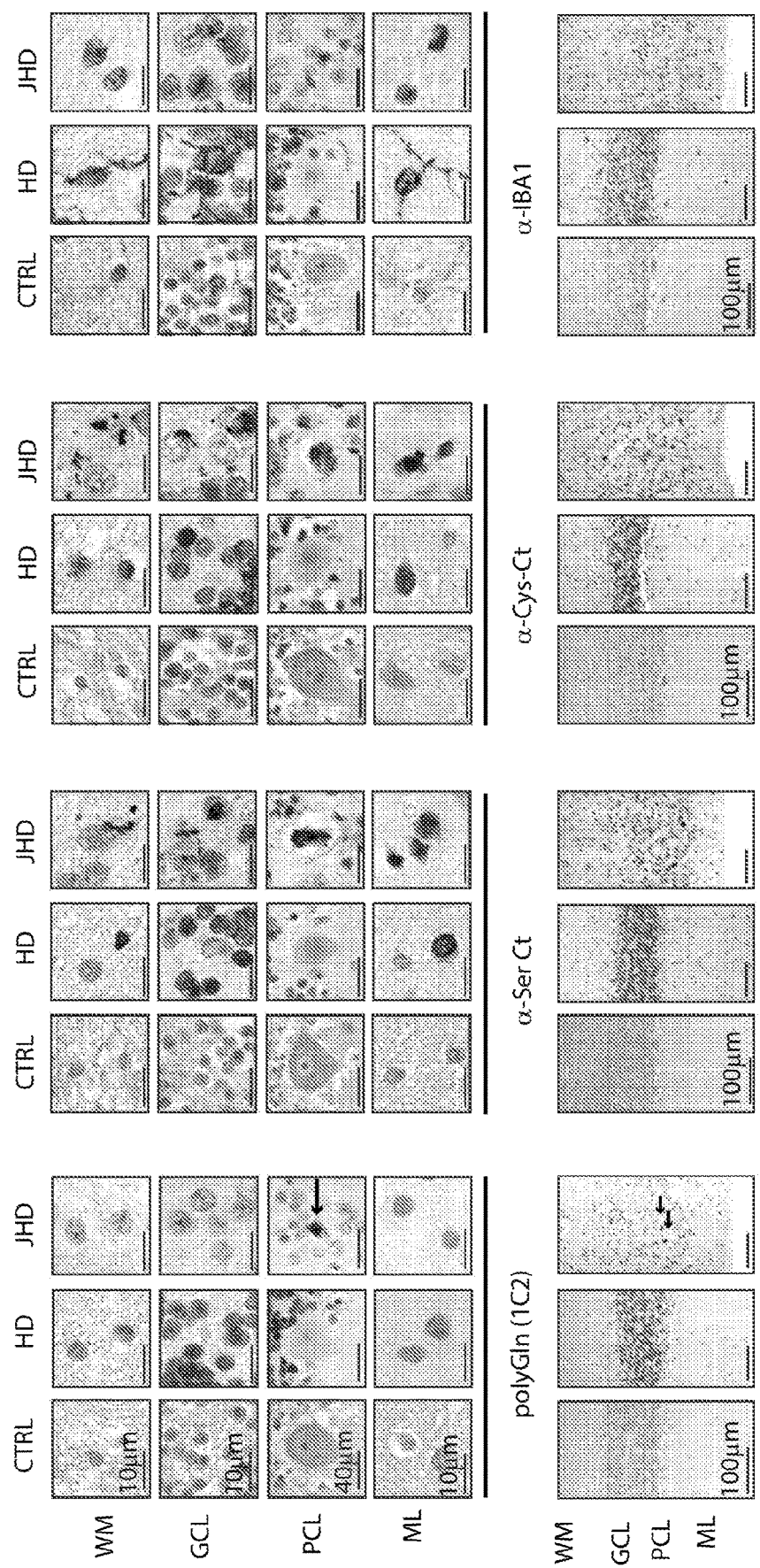
Figure 5D:
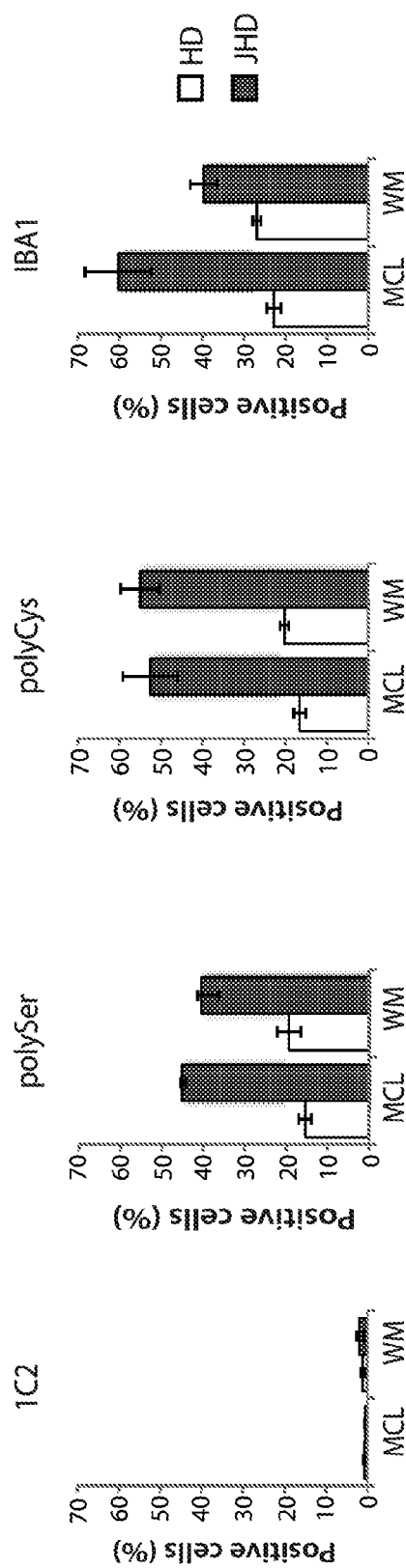

Similar to the results obtained in the adult-onset HD striatum (FIGS. 2A-2K), Iba1 staining of juvenile HD cerebella showed abundant microglial cells in regions strongly positive for HD-RAN polySer and polyCys. Microglial staining mostly displayed a ramified morphology in the adult and less affected juvenile cerebellum. In contrast, Iba1 positive cells were more abundant in the severely affected juvenile cerebellum and displayed active, round amoeboid morphology, with a similar distribution pattern to that observed for α-polySer and α-polyCys staining (FIGS. 5C, 22A-22T). These results show high levels of RAN protein accumulation in severely affected regions with minimal polyGln staining.

Example 2: Detection of RAN Proteins in a Biological Sample

Knock-in HD (KI HD) mice expressing humanized HTT exon 1 were used in this example. These mice express the murine HTT gene (hdh) under the control of its endogenous promoter. A CAG repeat region containing the human Ct flanking regions was inserted to replace the endogenous murine 8xGln repeat region.

Figure 6:
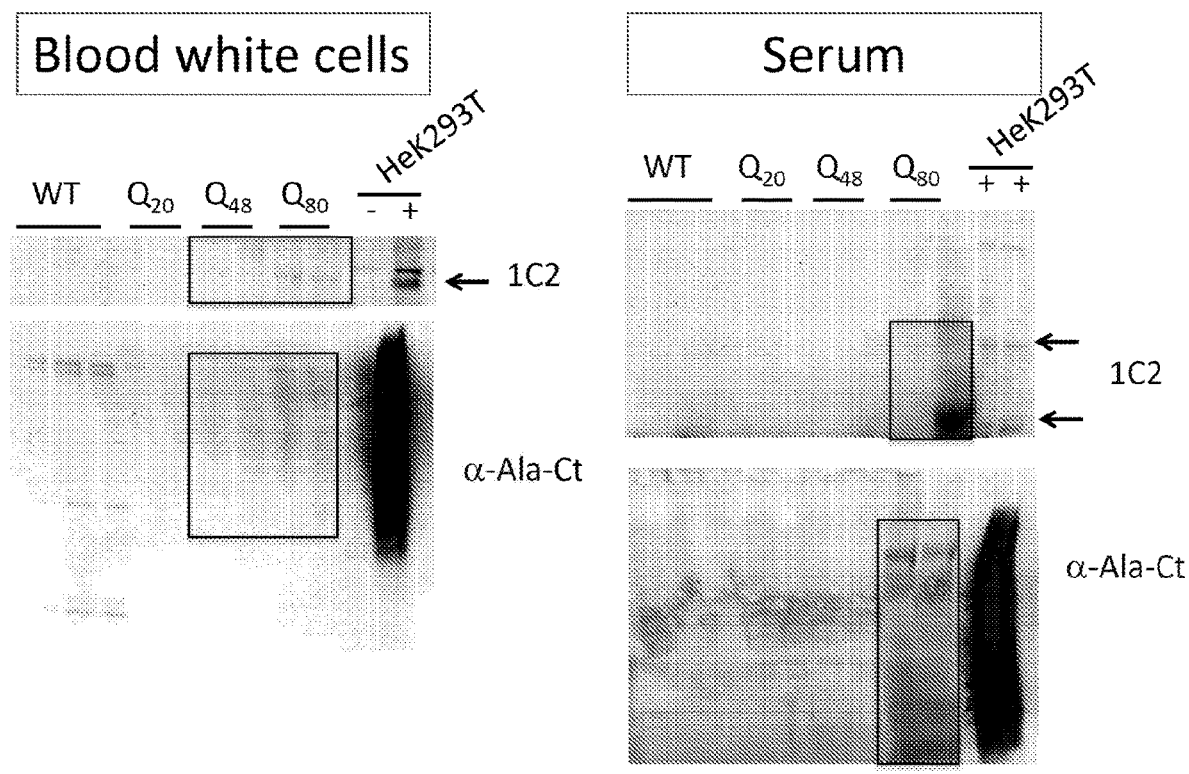
FIG. 6 shows Western blot data measuring levels of polyGln and polyAla from the blood or serum of HD mice containing 20, 48, and 80 CAG repeats. Poly-Ala was detected in both blood and serum of mice containing 48 and 80 CAG repeats.

The levels of polyGln and polyAla were tested from the blood or serum of HD mice containing 20, 48, and 80 CAG repeats (e.g., after performing antigen retrieval). WT mice were included as a negative control and HEK293T cells expressing a triple-tagged Htt-exon1 construct were used as a positive control. Poly-Ala was detected in both blood and serum of mice containing 48 and 80 CAG repeats (FIG. 6).

Example 3: In Vivo Mouse Models of HD RAN Proteins

This example describes HD-RAN protein accumulation increases with age and as the disease progresses. Additionally, it demonstrates that HD RAN proteins can be detected in blood in both animal models and in human patients.

FIGS. 24A-24C show PolySer HD RAN protein accumulation increases with age and disease in a HD mouse model. Briefly, immunohistochemistry was performed on HD transgenic HD transgenic N586-82Q mice. Data show RAN PolySer staining in different brain regions (e.g., striatum, cortex, hippocampus, and cerebellum) at 11 months (FIG. 24A), 10 months (FIG. 24B), and 6 months (FIG. 24C) of age. PolySer accumulation increases with age and no similar signal was detected in wild-type littermates.

Figure 25:
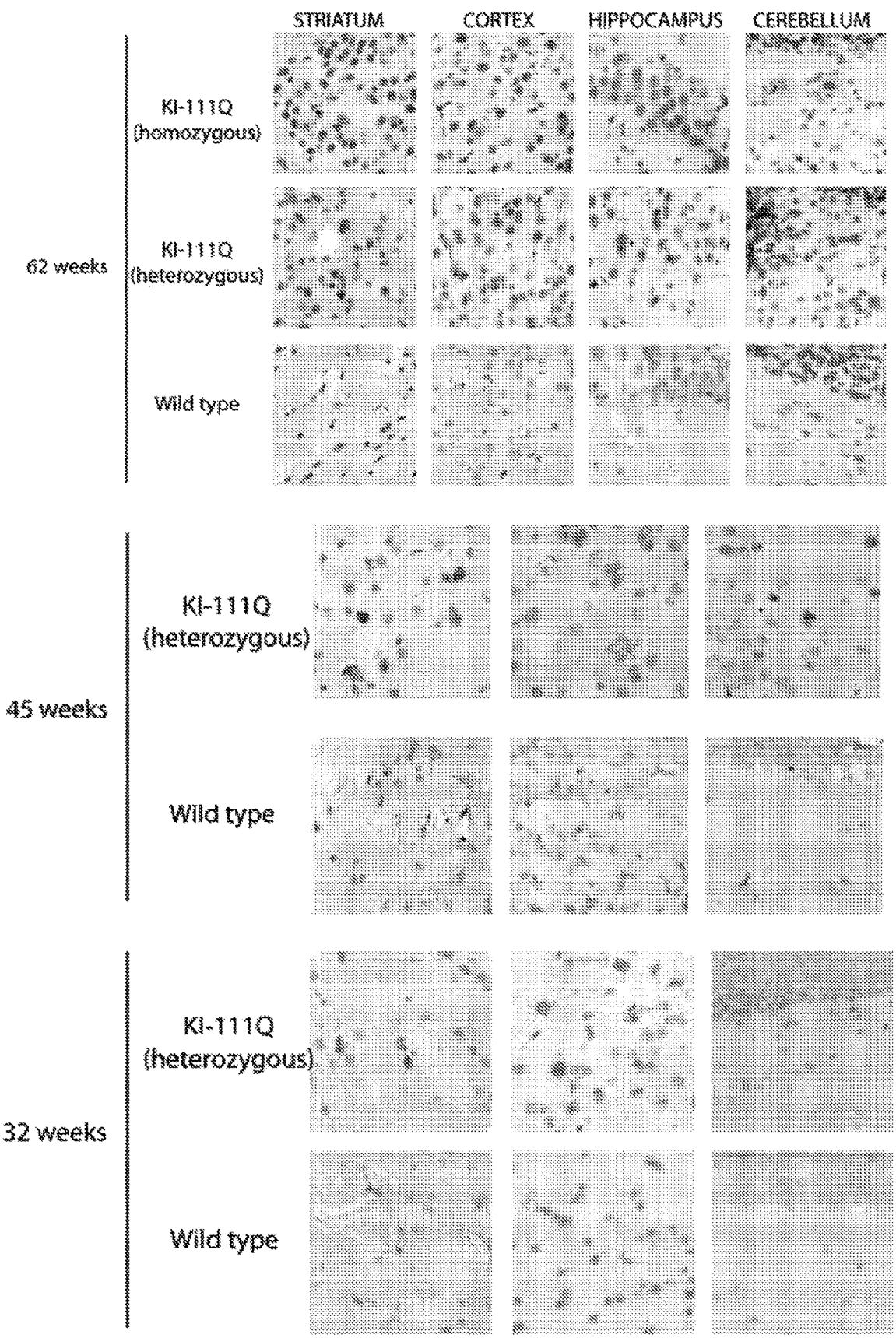
FIG. 25 shows PolySer HD RAN protein accumulation increases with age and disease in HDH KI-111Q mice. Immunohistochemistry of control and knock-in 111Q HD mice at different ages using α-Ser-Ct antibody. Staining was performed in different brain regions and showed age-dependent polySer accumulation in HD mice but not in wild type littermates.

A similar longitudinal study was conducted in hdh 111Q Knock-in mice (Wheeler et al., Hum. Molec. Genet. 2000), which express a chimeric human HTTexon1 within the full-length mouse Htt gene and develop a slower progressive phenotype. In this mouse model the mouse Htt gene with a humanized exon1, is driven using the endogenous mouse promotor. In these animals, HD-PolySer accumulation was detected in the striatum, cortex and hippocampus at 32 weeks, and increased with age (FIGS. 25A-25B).

Figure 26A:
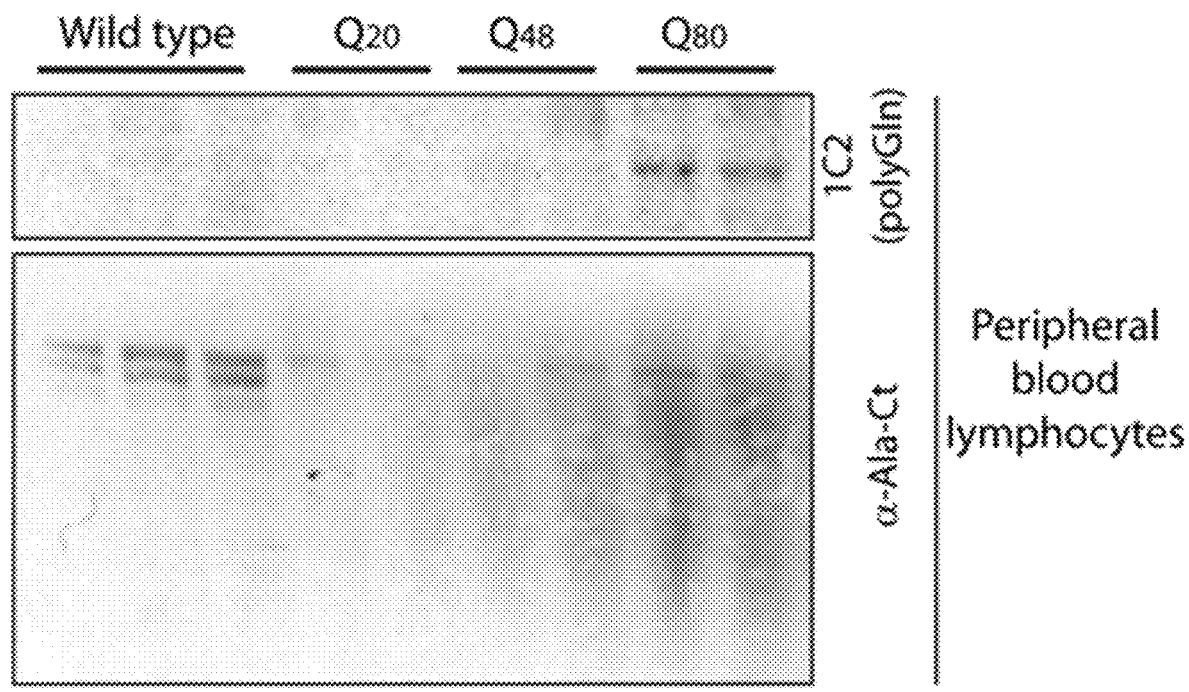
FIGS. 26A-26B show immunoblots showing HD-RAN polyAla protein accumulation is repeat-length dependent. PolyGln and polyAla accumulation increases with repeat length in peripheral blood lymphocytes (FIG. 26A) and serum (FIG. 26B) from HD knock-in mice with 20, 48 and 80 CAG repeats.
Figure 26B:
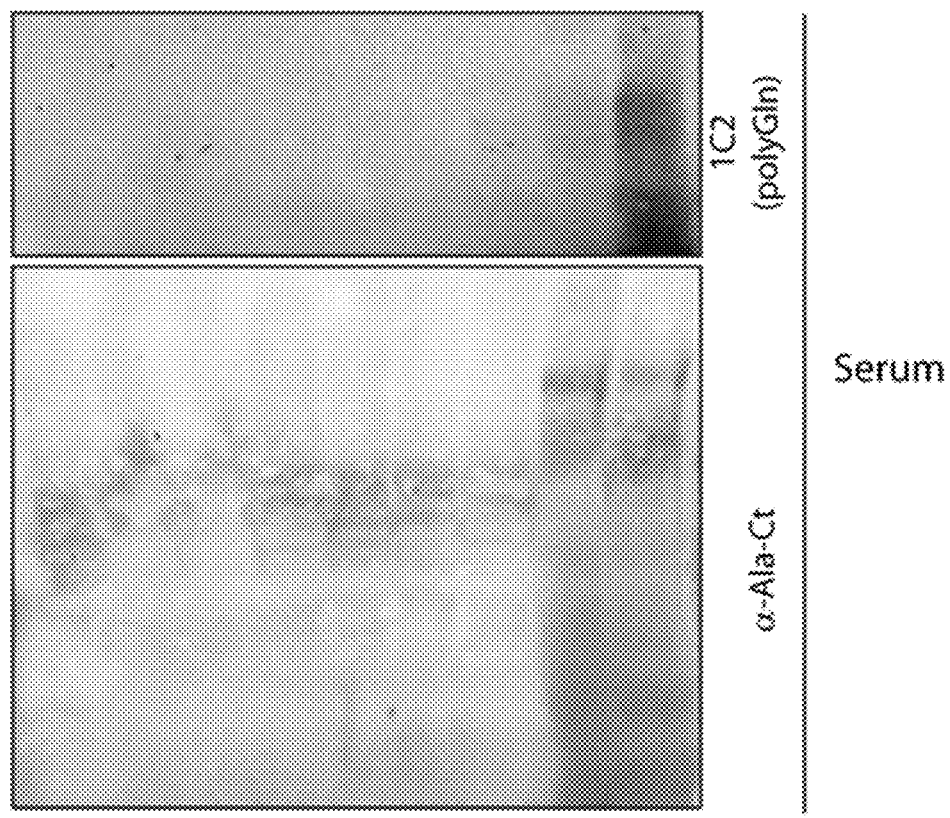

Additionally, polyAla and polyGln proteins were detected in peripheral blood lymphocytes and serum from knock-in mice carrying different repeat lengths. Briefly, blood and serum were obtained from knock-in mice and subjected to immunoblotting using 1C2 and anti-polyAla antibodies. As shown in FIGS. 26A-26B, polyGln and HD RAN-polyAla protein accumulation increases in mice with longer CAG repeat tracts. PolyAla can be detected in the blood of mice carrying 48 CAG and the levels are higher in mice carrying 80 CAG repeats at 62 weeks of age. PolyAla was not detected in control knock-in mice containing 20 CAG repeats. Similarly, both polyGln and HD RAN-polyAla was found in serum from mice with 80 CAG repeats.

Figure 27A:
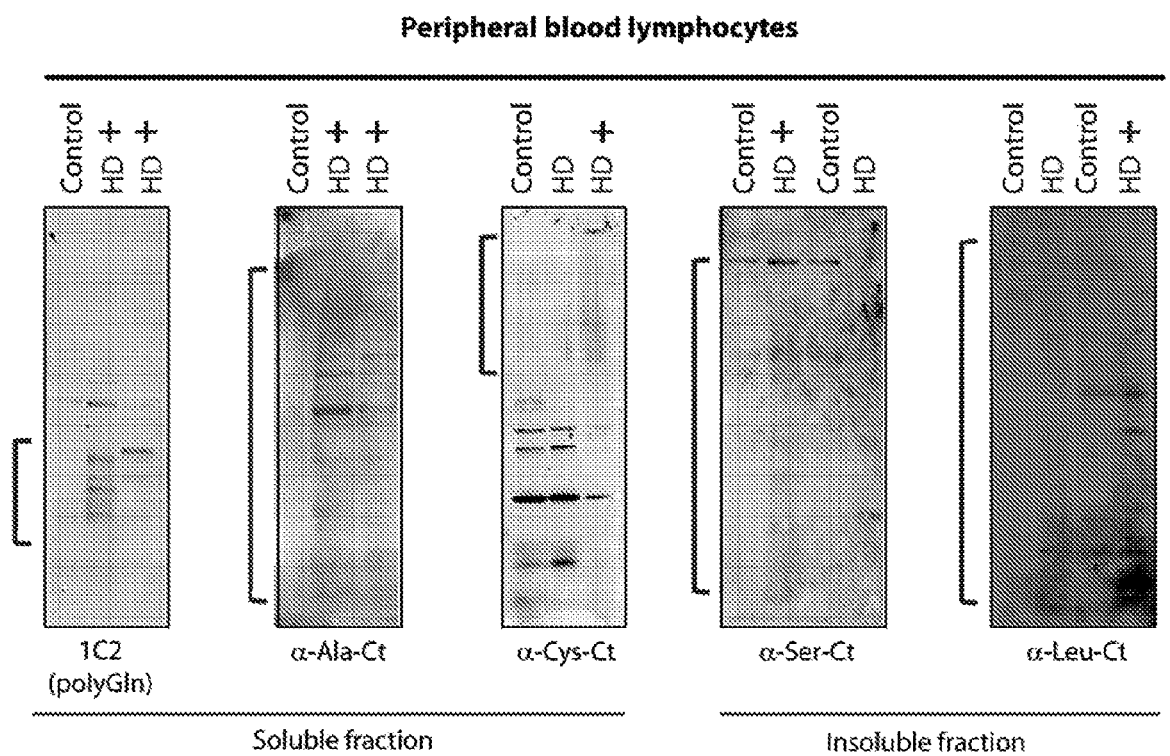
FIGS. 27A-27B show HD-RAN proteins detected in blood from HD patients. Immunoblots showing polyGln and HD-RAN protein accumulation in peripheral blood lymphocytes from HD patients (FIG. 27A) HD-RAN proteins were detected as high-molecular weight smears (see brackets) by immunoblotting in HD (indicated by a "+") but not control samples.
Figure 27B:
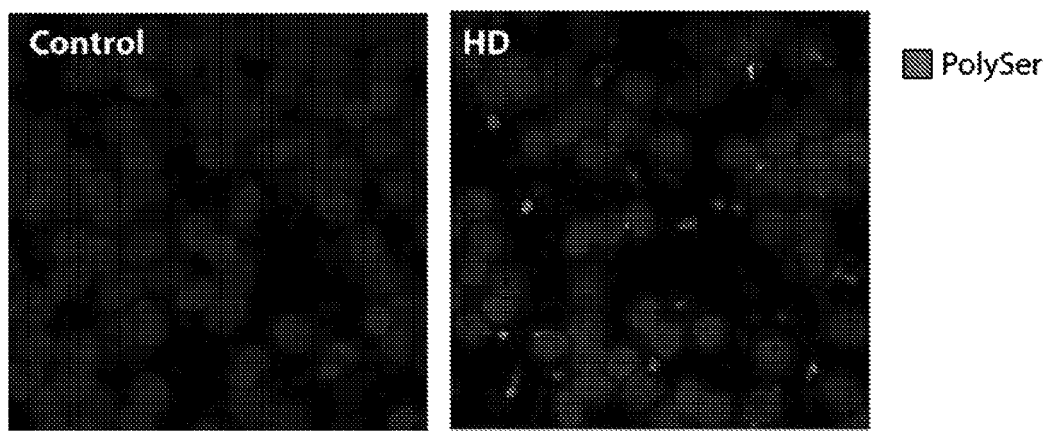

HD-RAN proteins were also detected in the blood from human HD patients. Protein blot and immunofluorescence experiments show HD RAN-polyAla and HD RAN-polySer (sense) and HD RAN-polyLeu and HD RAN-polyCys (antisense) proteins accumulate in peripheral blood lymphocytes from HD patients (FIGS. 27A-27B).

Taken together, these data indicate that HD-RAN protein accumulation increases with repeat length and disease severity. Furthermore, the detection of RAN proteins in both mouse and human blood demonstrates that RAN proteins are useful biomarkers for disease onset and progression. Assays to detect HD-RAN proteins as biomarkers of disease may use one or more molecular assays, including but not limited to methods that use antibodies or aptamers to detect these proteins and ELISA or other molecular detection methods that can be adapted for high-throughput detection of HD-RAN proteins in human tissues, including blood and CSF.

Example 4: Materials and Methods cDNA Constructs
HTTexon1 Triple Tag Vectors

HTTexon1—IRES-GFP expressing vectors differing in CAG repeat length (CAG23, CAG35, CAG45, CAG52, CAG80, CAA80) were used. HTTexon1 variants were excised using BamHI and EcoRI and subcloned into a modified pcDNA 3.1 vector (Life Technologies) containing 6× Stop codon cassette before the cloning site and three triple epitope tags (Flag, HA, myc) at the C-terminal region.
HTT C-Terminal Vectors p3XFlag-HTT-Ct vectors were generated by inserting a triple Flag tag on the pCDNA3.1 vector backbone. EcoRI-CAG23/105-BglII minigenes were subsequently inserted right after the 3XFlag region.

Additionally, DNA sequence located after the CAG repeat in the human HTT gene were amplified by PCR from human genomic DNA using the primers: HTT-Cterm-BglII-Fw1 (5'-GGAAGATCTAACCTCCTCAGCTTCCTCAGC-3') (SEQ ID NO: 15) and HTT-Cterm-BamHI-Rev (5'-CGCGGATCCTGCTGGGTCACTCTGTCTCT-3') (SEQ ID NO: 16). Primers contained overhangs including BglII and BamHI restriction sites. PCR products were inserted into p3xFLAG-CAG digested with the same restriction enzymes to generate constructs expressing ATG-initiated polyGln (CAG) containing the endogenous HTT C-terminal regions (Ct). To generate ATG-initiated polySer-Ct (AGC) or ATG-initiated polyAla-Ct (GCA) constructs, polyGln-Ct vectors were linearized between 3XFlag and CAG expansion regions using XhoI and treated with T4-PNK or mung bean to change the reading frame.

The same approach was followed to generate $HTT_{AS}$ C-terminal vectors. EcoRI-CTG23/105-SalI minigenes were inserted into p3XFLAG vectors. $HTT_{AS}$ C-terminal region was cloned using the primers HTTAS-Cterm-SalI-Fw1 (5'-acgcgtcgacgTGGAAGGACTTGAGGGACTC-3') (SEQ ID NO: 17) and HTTAS-Cterm-BamHI-Rev1 (5'-cgcggatccCCGCTCAGGTTCTGCTTTTA-3') (SEQ ID NO: 18) and inserted into p3XFLAG-CTG vectors to generate ATG-initiated polyLeu (CTG) C-terminal constructs. XhoI digestion and T4-PNK/mung bean treatment was performed to generate ATG-initiated polyCys-Ct (TGC) and ATG-initiated polyAla-Ct (GCT) expressing constructs.

HD-RAN Alternative Codon Vectors

Minigenes for HD polyGln and RAN products were designed, synthesized by ADT Technologies, and inserted into p3XFLAG vectors. The CAG/CTG expansion was substituted by CAA repeats for polyGln, TCTTCC for polySer, CTTCTC for polyLeu and TGT for polyCys to avoid RNA hairpins and prevent RAN translation. Codon substitution was not available for ATG-initiated polyAla constructs, which were generated using AGC repeats.

The integrity of all constructs was confirmed by sequencing.

Production of Polyclonal Antibodies.

Polyclonal antibodies were generated. The α-HD-CAG-ALA & α-HD0Ala(sense)-Ct antisera were raised against synthetic peptide corresponding to the C-terminal regions of the predicted polyAla and polySer frames of HD in the CAG direction: APAAAPAATRPG (SEQ ID NO: 19) and RPR-RHPARLWLRSR (SEQ ID NO: 20) respectively. The α-HD-Cys-Ct & α-HD-Leu-Ct were raised against synthetic peptide corresponding to the C-termini of the predicted polyCys and polyLeu frames of HD in the CTG direction: KDLRDSKAFISFSR (SEQ ID NO: 21) and GLGPTR-GAAQHRG (SEQ ID NO: 22), respectively.

Cell Culture and Transfection

SH-SY5Y (human neuroblastoma), T98 (human glioblastoma), and HEK293T (human embryonic kidney) were maintained under standard conditions of temperature (37° C.), humidity (95%), and carbon dioxide (5%) and grown in Dulbecco's Modified Eagle's Medium (DMEM, Life technologies) supplemented 10% FBS (Fetal Bovine Serum, Corning cellgro), 100 units/ml penicillin and 100 µg/ml Streptomycin (Corning cellgro). Transfection experiments were conducted using Lipofectamine 2000 (Life technologies), according to the manufacturer's instruction and at a 60% cell confluence. Cells were plated 24 hours before transfection.

Human Autopsy Tissue

Control and HD autopsy tissue was collected with informed consent of patients or their relatives and approval of local institutional review boards.

Immunofluorescence

T98 and HEK293T cells were grown on coverslides. At the indicated time after transfection, cells were rinsed with PBS and fixed for 30 min at room temperature with 4% paraformaldehyde in PBS. Cells were then washed in PBS and permeabilized for 30 min in 0.5% Triton-X-100 in PBS. Non-specific binding was blocked by incubation in 10% FBS in PBS for 1 hour. Incubation with the indicated primary antibody dilutions was carried out overnight at 4° C. in PBS containing 1% FBS. After washing three times in PBS 1×, coverslides were incubated with secondary anti-mouse IgG Alexa 488 or IgG Alexa 594 (Molecular Probes) at a dilution of 1:2000 for 1 hour at room temperature. Coverslides were washed and mounted in Vectashield-DAPI (Invitrogen), and cells visualized under a Leica confocal microscope. Images were captured using a digital camera (Leica TCS SP5). Primary antibodies used were anti-polyQ (MAB1574, 1:2000, Millipore), anti-Flag M2 (1:1500, Sigma), anti-HA (1:1500, Covance). α-Ala-Ct, α-Ser-Ct, α-Leu-Ct and α-Cys-Ct were used at 1:1000, 1:500, 1:1500 and 1:500 respectively.

Immunohistochemistry

For the detection of HD-RAN proteins using C-terminal antibodies the following protocol was followed under harsh antigen exposure conditions. Eight-micrometer sections were deparaffinized in xylenes and rehydrated through an alcohol gradient. Subsequent antigen retrieval steps were performed. First, 1 ug/mL proteinase K treatment in 1 mM $CaCl_2$, 50 mM Tris buffer (pH=7.6) for 40 minutes at 37° C. Second, pressure cooked in 10 mM EDTA (pH=6.5) for 15 minutes. Third, 95% formic acid treatment for five minutes. Endogenous peroxidase block was performed in 3% $H_2O_2$ methanol for ten minutes. To block nonspecific binding a non-serum block (Biocare Medical) was applied for 15 minutes.

Primary antisera were applied in 1:10 non-serum block at 4° C. overnight; α-polyAla (1:5000), α-polySer (1:4500), α-polyCys (1:2500), and α-polyLeu (1:6000). Rabbit Linking Reagent (Covance) was applied for 30 minutes at room temperature. Secondary antibodies were Biotin-Avidin/Streptavidin labeled using ABC reagent (Vector laboratories, Inc.) and detection performed by exposure to Vector Red Substrate Kit (Vector Laboratories, Inc.). Slides were finally dehydrated and mounted using Cytoseal 60 (Electron microscopy sciences).

Additional primary antibodies used were: α-Iba1 (Abcam, goat, 1:1000), α-active Caspase-3 (Abcam, rabbit, 1:300), EM48 (Millipore, mouse, 1:75), 1C2 (Millipore, mouse, 1:10000 for staining in striatum and cortex; 1:10000/1:3000/1:1000 for cerebellar staining).

Immunoblotting

Cells in each well of a six-well tissue-culture plate were rinsed with PBS and lysed in 90 µL RIPA buffer for 3 minutes on ice. The cell lysates were collected and centrifuged at 16,000×g for 15 min at 4° C. The protein concentration of the supernatant was determined using the protein assay dye reagent (Bio-Rad). Twenty micrograms of protein were separated in a 4-12% NuPage Bis-Tris gel (Invitrogen) and transferred to a nitrocellulose membrane (Amersham). The membrane was blocked in PBS containing 0.05% Tween-20 detergent (PBS-T) and 5% dry milk powder. Primary antibodies were prepared in 1% milk in PBS-T and incubated overnight at 4° C. After washing with PBS-T, membranes were incubated with secondary antibodies (1:3000 in PBS-T) for 1 hour at room temperature and washed with PBS-T. Detection was performed using Western Lightning Plus-ECL (Perkin Elmer).

Primary antibodies were anti-polyQ (MAB1574, 1:2000, Millipore), anti-Flag M2 (1:3000, Sigma), anti-HA (1:2000, Covance). α-Ala-Ct, α-Ser-Ct, α-Leu Ct and α-Cys Ct were used at 1:2000, 1:750, 1:1500 and 1:750 respectively. Anti-GAPDH (1:5000, ab8245 Abcam) was used as loading control. Secondary antibodies were peroxidase-conjugated anti-mouse and anti-rabbit (1:3000, GE Healthcare). Membranes were blocked in 3% BSA PBS-T for α-polyCys-Ct incubations.

Cell-Viability and Cell-Toxicity Assays

Cell viability was determined 42 hours post-transfection using the 3-(4,5-dimethythiazol-2-yl)-2,5-diphenyl tetrazolium bromide (MTT) assay. MTT was dissolved in PBS, added to cell culture media at a final concentration of 0.5 mg/ml and incubated for 60 minutes at 37° C. Cell medium was removed and the resultant intracellular formazan product solubilized in 100 ul of DMSO. Absorbance was measured at 550 nm. MTT determinations were performed in quintuplicate for each independent experiment.

Cell toxicity was determined using lactate dehydrogenase release from dying cells (Cytotox 96, Promega) following manufacturer's protocol. LDH determinations were performed in five independent experiments each performed in quintuplicates and measured at 490 nm.

Statistical Analysis

Statistical significance was calculated using the two-tailed unpaired t-student's test for single comparisons ($p<0.05$) and the analysis of variance (ANOVA) for the comparison of multiple pair-wise conditions. "n" refers to independent experiments.

RNA Quantification for Cell-Toxicity Assays

Total RNA from transfected cells was isolated using miRNeasy Mini Kit (Qiagen) following the manufacturer's instructions. RNA was retrotranscribed using the SuperScript III RT kit (Invitrogen) and random hexamer primers. HD-RAN alternative codon cDNAs were amplified using iQ™ SYBR® Green Supermix (Biorad) using the primers: 3xFLAG Forward; 5'-ACCTCCTCAGCTTCCTCAGC-3' (SEQ ID NO: 23), sFLAG Reverse: (5'-GCTGGGT-CACTCTGTCTCTG-3') (SEQ ID NO: 24). β-Actin was used as a reference gene and was amplified using the primers: ACTB-3: 5'-CTGGAACGGTGAAGGTGACA-3' (SEQ ID NO: 25); ACTB-4: 5'-GGGAGAGGACTGGGC-CATT-3' (SEQ ID NO: 26). q-RT-PCR results were analyzed using the 2-delta delta Ct method.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

---

The invention claimed is:

1. A method for producing an antibody or fragment thereof, the method comprising: administering to a non-human subject or cell a peptide antigen consisting of the amino acid sequence set forth in SEQ ID NO: 19 to produce an anti-repeat-associated non-ATG (RAN) protein antibody or fragment thereof and isolating the anti-RAN protein antibody or fragment thereof, wherein the isolated anti-RAN antibody or fragment thereof is a humanized antibody or a chimeric antibody.

2. The method of claim 1, wherein the non-human subject is a mouse, a hamster, a rat, a rabbit, or a goat or the cell is a hybridoma cell.

3. The method of claim 1, wherein the isolated anti-RAN antibody or fragment thereof is a polyclonal antibody or a monoclonal antibody.

4. The method of claim 1, further comprising screening the isolated anti-RAN antibody using at least one of enzyme-linked immunosorbent assay (ELISA), surface plasmon resonance analysis, western blot, immunohistochemistry (IHC), or immunofluorescence.

5. A method for producing an antibody or fragment thereof, the method comprising administering to a non-human subject or cell a peptide antigen consisting of the amino acid sequence set forth in SEQ ID NO: 20 to produce an anti-repeat-associated non-ATG (RAN) protein antibody or fragment thereof and isolating the anti-RAN protein antibody or fragment thereof.

6. The method of claim 5, wherein the non-human subject is a mouse, a hamster, a rat, a rabbit, or a goat or the cell is a hybridoma cell.

7. The method of claim 5, wherein the isolated anti-RAN antibody or fragment thereof is a polyclonal antibody or a monoclonal antibody.

8. The method of claim 7, wherein the isolated anti-RAN antibody or fragment thereof is a humanized antibody or a chimeric antibody.

9. The method of claim 5, further comprising screening the isolated anti-RAN antibody using at least one of enzyme-linked immunosorbent assay (ELISA), surface plasmon resonance analysis, western blot, immunohistochemistry (IHC), or immunofluorescence.

10. A method for producing an antibody or fragment thereof, the method comprising administering to a non-human subject or cell a peptide antigen consisting of the amino acid sequence set forth in SEQ ID NO: 21 to produce an anti-repeat-associated non-ATG (RAN) protein antibody or fragment thereof and isolating the anti-RAN protein antibody or fragment thereof.

11. The method of claim 10, wherein the non-human subject is a mouse, a hamster, a rat, a rabbit, or a goat or the cell is a hybridoma cell.

12. The method of claim 10, wherein the isolated anti-RAN antibody or fragment thereof is a polyclonal antibody or a monoclonal antibody.

13. The method of claim 12, wherein the isolated anti-RAN antibody or fragment thereof is a humanized antibody or a chimeric antibody.

14. The method of claim 10, further comprising screening the isolated anti-RAN antibody using at least one of enzyme-linked immunosorbent assay (ELISA), surface plasmon resonance analysis, western blot, immunohistochemistry (IHC), or immunofluorescence.

15. A method for producing an antibody or fragment thereof, the method comprising administering to a non-human subject or cell a peptide antigen consisting of the amino acid sequence set forth in SEQ ID NO: 22 to produce an anti-repeat-associated non-ATG (RAN) protein antibody or fragment thereof and isolating the anti-RAN protein antibody or fragment thereof.

16. The method of claim 15, wherein the non-human subject is a mouse, a hamster, a rat, a rabbit, or a goat or the cell is a hybridoma cell.

17. The method of claim 15, wherein the isolated anti-RAN antibody or fragment thereof is a polyclonal antibody or a monoclonal antibody.

18. The method of claim 17, wherein the isolated anti-RAN antibody or fragment thereof is a humanized antibody or a chimeric antibody.

19. The method of claim 16, further comprising screening the isolated anti-RAN antibody using at least one of enzyme-linked immunosorbent assay (ELISA), surface plasmon resonance analysis, western blot, immunohistochemistry (IHC), or immunofluorescence.

\* \* \* \* \*